(12) United States Patent
O'Connor

(10) Patent No.: US 11,040,094 B2
(45) Date of Patent: Jun. 22, 2021

(54) COMPOSITIONS AND METHODS FOR TREATING IMMUNOLOGICAL DYSFUNCTION

(71) Applicant: Colleen M. O'Connor, Houston, TX (US)

(72) Inventor: Colleen M. O'Connor, Houston, TX (US)

( * ) Notice: Subject to any disclaimer, the term of this patent is extended or adjusted under 35 U.S.C. 154(b) by 290 days.

(21) Appl. No.: 15/200,999

(22) Filed: Jul. 1, 2016

(65) Prior Publication Data

US 2017/0000869 A1   Jan. 5, 2017

Related U.S. Application Data

(60) Provisional application No. 62/187,493, filed on Jul. 1, 2015.

(51) Int. Cl.
| *A61K 39/00*  | (2006.01) |
| *A61K 39/39*  | (2006.01) |
| *A61K 9/00*   | (2006.01) |
| *C07K 14/735* | (2006.01) |
| *C07K 14/74*  | (2006.01) |

(52) U.S. Cl.
CPC ........ *A61K 39/0011* (2013.01); *A61K 9/0019* (2013.01); *A61K 39/0008* (2013.01); *A61K 39/39* (2013.01); *C07K 14/70535* (2013.01); *C07K 14/70539* (2013.01); *A61K 2039/505* (2013.01); *A61K 2039/5156* (2013.01); *A61K 2039/5158* (2013.01); *C07K 2317/622* (2013.01)

(58) Field of Classification Search
None
See application file for complete search history.

(56) References Cited

U.S. PATENT DOCUMENTS

| 4,683,202 | A  |   | 7/1987  | Mullis         |              |
|-----------|----|---|---------|----------------|--------------|
| 4,797,368 | A  |   | 1/1989  | Carter et al.  |              |
| 5,139,941 | A  |   | 8/1992  | Muzyczka et al.|              |
| 5,928,906 | A  |   | 7/1999  | Koster et al.  |              |
| 5,994,136 | A  |   | 11/1999 | Naldini et al. |              |
| 6,013,516 | A  |   | 1/2000  | Verma et al.   |              |
| 2002/0009468 | A1 | * | 1/2002 | Selvaraj  | A61K 39/0005 424/277.1 |
| 2006/0034810 | A1 | * | 2/2006 | Riley     | A61K 39/21 424/93.21 |
| 2012/0321666 | A1 |   | 12/2012 | Cooper et al. |         |

FOREIGN PATENT DOCUMENTS

| WO | WO 1995/000655 A1 | 1/1995 |           |
|----|-------------------|--------|-----------|
| WO | WO 1995/027071 A2 | 10/1995|           |
| WO | WO-2004098529 A2 * | 11/2004 | ......... A61K 39/0011 |

OTHER PUBLICATIONS

McCutcheon et al., 1995, J. Exp. Med. vol. 181: 2085-2095.*
Boegel et al., 2014, OncoImmunology VOl. 3: 1-12.*
Wen et al., 2002, J. Immunol. vol. 168: 4897-4906.*
Nagarajan et al., 2002, Canc. Res. vol. 62: 2869-2874.*
Forget et al., Nov./Dec. 2014, J. Immunother. vol. 37: 448-460.*
Wang eta l., 2012, Clin. Exp. Immunol. vol. 172: 104-112.*
Zhao et al., 2010, Vaccine: 2846-2852.*
Elgueta et al., 2009, Immunol. Rev. vol. 229: 1-31.*
Habib et al., 2003, Allergy Clin Immunol, VOl 112: 1033-45.*
Galian et al., 2012: J. Biol. Chem. vol. 287: 16399-16409.*
Salih et al., 2001, J. Immunol. vol. 167:4059-4066.*
Grinshtein, N., et al., "Neoadjuvant vaccination provides superior protection against tumor relapse following surgery compared with adjuvant vaccination." Cancer Research (2009); 69.9: 3979-3985.
Grinshtein, N., et al., "High-dose chemotherapy augments the efficacy of recombinant adenovirus vaccines and improves the therapeutic outcome." Cancer Gene Therapy (2009); 16.4: 338-350.
Janeway, C.A. et al., Chapter 7, The Development and Survival of Lymphocytes. Immunobiology: The Immune System in Health & Disease, Sixth Edition (2005), 21 pages.
Jarnicki, A.G., et al., "Suppression of antitumor immunity by IL-10 and TGF-β-producing T cells infiltrating the growing tumor: influence of tumor environment on the induction of CD4+ and CD8+ regulatory T cells." The Journal of Immunology (2006); 177.2: 896-904.
Li, Z., et al., "The generation of antibody diversity through somatic hypermutation and class switch recombination." Genes & Development (2004); 18.1: 1-11.
Liu and Schatz, "Balancing AID and DNA repair during somatic hypermutation." Trends in Immunology (2009); 30.4: 173-181.
Michishita, M., et al., "Antitumor effect of bevacizumab in a xenograft model of canine hemangiopericytoma." Journal of Pharmacological Sciences (2013); 121.4: 339-342.
O'Connor, C.M., et al., "Adoptive T-cell therapy improves treatment of canine lymphoma non-Hodgkin lymphoma post chemotherapy." Scientific Reports (2012); 2: 249, 12 pages.
Odegard and Schatz, "Targeting of somatic hypermutation." Nature reviews Immunology (2006); 6.8: 573-583.
Huppa and Davis, "T-cell-antigen recognition and the immunological synapse." Nature Reviews Immunology (2003); 3.12: 973-983.
Thomas and Capecchi, "Site-directed mutagenesis by gene targeting in mouse embryo-derived stem cells." Cell (1987); 51.3: 503-512.
Mansour, S.L. et al., "Disruption of the proto-oncogene int-2 in mouse embryo-derived stem cells: a general strategy for targeting mutations to non-selectable genes." Nature (1988); 336.6197: 348-352.
Joyner, A.L., et al., "Production of a mutation in mouse En-2 gene by homologous recombination in embryonic stem cells." Nature (1989); 338: 153-156.
Freeman, G.J., et al., "Cloning of B7-2: a CTLA-4 counter-receptor that costimulates human T cell proliferation." Science (1993); 262: 909-909.

(Continued)

*Primary Examiner* — Amy E Juedes
(74) *Attorney, Agent, or Firm* — Cooley LLP; Cynthia A. Kozakiewicz; (Chris) Chun L. Yu

(57) ABSTRACT

The present invention is directed to methods of lymphotherapy to treat cancer, infection and autoimmune disease.

23 Claims, 7 Drawing Sheets

Specification includes a Sequence Listing.

(56) References Cited

OTHER PUBLICATIONS

Young, J.W., et al., "The B7/BB1 antigen provides one of several costimulatory signals for the activation of CD4+ T lymphocytes by human blood dendritic cells in vitro." Journal of Clinical Investigation (1992); 90.1: 229.
Nabavi, N., et al., "Signalling through the MHC class II cytoplasmic domain is required for antigen presentation and induces B7 expression." Nature (1992); 360: 266-268.
Hermonat and Muzyczka, "Use of adeno-associated virus as a mammalian DNA cloning vector: transduction of neomycin resistance into mammalian tissue culture cells." Proceedings of the National Academy of Sciences (1984); 81.20: 6466-6470.
Allen, et al., "A comprehensive polymerase chain reaction-oligonucleotide typing system for the HLA class IA locus." Human Immunology (1994); 40.1: 25-32.
Santamaria, P., et al., "HLA Class I Sequence-Based Typing." Human Imm. (1993); 37(1): 39-50.
Hurley, C.K. et al., "The search for HLA-matched donors: a summary of HLA-A*,-B*,-DRB1/3/4/5* alleles and their association with serologically defined HLA-A,-B,-DR antigens." Tissue Antigens (1997); 50.4: 401-418.
Teng and Papavasiliou, "Immunoglobulin somatic hypermutation." Annu. Rev. Genet. (2007); 41: 107-120.
Rabinovich, et al., "Immunosuppressive strategies that are mediated by tumor cells." Annual Review of Immunology (2007); 25: 267-296.
Ruella and Kalos, "Adoptive immunotherapy for cancer." Immunological Reviews (2014); 257.1: 14-38.
Scharf et al., "Effect of bevacizumab on angiogenesis and growth of canine osteosarcoma cells xenografted in athymic mice." American Journal of Veterinary Research (2013); 74.5: 771-778.
Sharma, et al., "γ-Radiation promotes immunological recognition of cancer cells through increased expression of cancer-testis antigens in vitro and in vivo." PLoS One (2011); 6.11: e28217.
Varilla, et al., "Immune alterations and immunotherapy prospects in head and neck cancer." Expert Opinion on Biological Therapy (2013); 13.9: 1241-1256.
Poloso Neil J et al: "Development of therapeutic vaccines by direct modification of cell membranes from surgically removed human tumor tissue with immunostimulatory molecules", Vaccine, vol. 19, No. 15-16, Feb. 28, 2001, pp. 2029-2038.
Budde Lihua E et al: "Combining a CD20 Chimeric Antigen Receptor and an Inducible Caspase 9 Suicide Switch to Improve the Efficacy and Safety of T Cell Adoptive Immunotherapy for Lymphoma", Plos One, vol. 8, No. 12, e82742, Dec. 2013.
O'Connor Colleen M et al: "Adoptive T-cell therapy improves treatment of canine non-Hodgkin lymphoma post chemotherapy", Scientific Reports, vol. 2, Feb. 2012.
Medof M Edward et al: "Cell-surface engineering with GPI-anchored proteins", Faseb Journal, vol. 10, No. 5, 1996, pp. 574-586.
Rebhandl S et al: "AIDing cancer treatment: Reducing AID activity via HSP90 inhibition", European Journal of Immunology, vol. 45, No. 8, 2208-2211, Aug. 1, 2015.
Aquino, A. et al., "Drug-induced increase of carcinoembryonic antigen expression in cancer cells," Pharmacol Res. May 2004; 49(5):383-96.
Bagnat, M. et al., "Lipid rafts function in biosynthetic delivery of proteins to the cell surface in yeast," Proc Natl Acad Sci USA Mar. 28, 2000; 97(7):3254-9.
Gattinoni, L. et al., "Adoptive immunotherapy for cancer: building on success," Nat Rev Immunol. May 2006; 6(5):383-93.

Gattinoni, L. et al., "CTLA-4 dysregulation of self/tumor-reactive CD8$^+$T-cell function is CD4$^+$T-cell dependent," Blood Dec. 1, 2006; 108(12):3818-23. Epub Aug. 1, 2006.
Gros, A. et al., "PD-1 identifies the patient-specific CD8$^+$tumor-reactive repertoire infiltrating human tumors," J Clin Invest. May 2014; 124(5):2246-59. doi: 10.1172/JCI73639. Epub Mar. 25, 2014.
Hinrichs, C. S. et al., "Programming CD8$^+$T cells for effective immunotherapy," Curr Opin Immunol. Jun. 2006; 18(3):363-70. Epub Apr. 17, 2006.
Kaiser, L. R. et al., "Adjuvant therapy for malignant melanoma," Surg Clin North Am. Dec. 1981; 61(6):1249-57.
Kaneno, R. et al., "Chemotherapeutic agents in low noncytotoxic concentrations increase immunogenicity of human colon cancer cells," Cell Oncol. Apr. 2011; 34(2):97-106. doi: 10.1007/s13402-010-0005-5. Epub Jan. 20, 2011.
Karandikar, N. J. et al., "Unusual immunophenotype of CD8$^+$T cells in familial hemophagocytic lymphohistiocytosis," Blood Oct. 1, 2004; 104(7): 2007-9. Epub Jun. 17, 2004.
Klebanoff, C. A. et al., "CD8$^+$T-cell memory in tumor immunology and immunotherapy," Immunol Rev. Jun. 2006; 211:214-24.
Mitchell, L. et al., "Clinical and immunomodulatory effects of toceranib combined with low-dose cyclophosphamide in dogs with cancer," J Vet Intern Med. Mar.-Apr. 2012; 26(2):355-62. doi: 10.1111/j.1939-1676.2011.00883.x. Epub Feb. 4, 2012.
Mitchell, L. et al., "Induction of remission results in spontaneous enhancement of anti-tumor cytotoxic T-lymphocyte activity in dogs with B cell lymphoma," J Vet Immunol Immunopathol. Feb. 15, 2012; 145(3-4):597-603. doi: 10.1016/j.vetimm.2012.01.006. Epub Jan. 14, 2012.
Nefedova, Y. et al., "Inhibition of Notch signaling induces apoptosis of myeloma cells and enhances sensitivity to chemotherapy," Blood Feb. 15, 2008; 111(4):2220-9. Epub 2007.
Nefedova, Y. et al., "Mechanism of all-trans retinoic acid effect on tumor-associated myeloid-derived suppressor cells," Cancer Res. Nov. 15, 2007; 67(22):11021-8. Erratum in: Cancer Res. Jan. 15, 2008; 68(2):626.
O'Connor, C. M. et al., "Developing T cell cancer immunotherapy in the dog with lymphoma," ILAR Journal 2014; 55(1):169-81.
Paulos, C. M. et al., "Microbial translocation augments the function of adoptively transferred self/tumor-specific CD8$^+$T cells via TLR4 signaling," J Clin Invest. Aug. 2007; 117(8):2197-204. Erratum in: J Clin Invest. Oct. 2007; 117(10):3140.
Paulos, C. M. et al., "Toll-like receptors in tumor immunotherapy," Clin Cancer Res. Sep. 15, 2007; 13(18 Pt 1):5280-9.
Panjwani, M. K. et al., "Feasibility and Safety of RNA-transfected CD20-specific Chimeric Antigen Receptor T Cells in Dogs with Spontaneous B Cell Lymphoma," Mol Ther. Sep. 2016; 24(9):1602-14. doi: 10.1038/mt.2016.146. Epub Jul. 12, 2016.
Shi, L. et al., "KLRG1 impairs CD4$^+$T cell responses via p16$^{ink4a}$ and p27$^{kip1}$ pathways: role in hepatitis B vaccine failure in individuals with hepatitis C virus infection," J Immunol. Jan. 15, 2014; 192(2):649-57. doi: 10.4049/jimmunol.1302069. Epub Dec. 13, 2013.
Tongu, M. et al., "Immunogenic chemotherapy with cyclophosphamide and doxorubicin against established murine carcinoma," Cancer Immunol Immunother. May 2010; 59(5):769-77. doi: 10.1007/s00262-009-0797-1. Epub Nov. 26, 2009.
Vose, J. M. et al., "Long-term update of a phase II study of rituximab in combination with CHOP chemotherapy in patients with previously untreated, aggressive non-Hodgkin's lymphoma," Leuk Lymphoma. Nov. 2005; 46(11):1569-73.
Voulgarelis, M. et al., "Myelodysplasia-associated autoimmunity: clinical and pathophysiologic concepts," Eur J Clin Invest. Oct. 2004; 34(10):690-700.

* cited by examiner

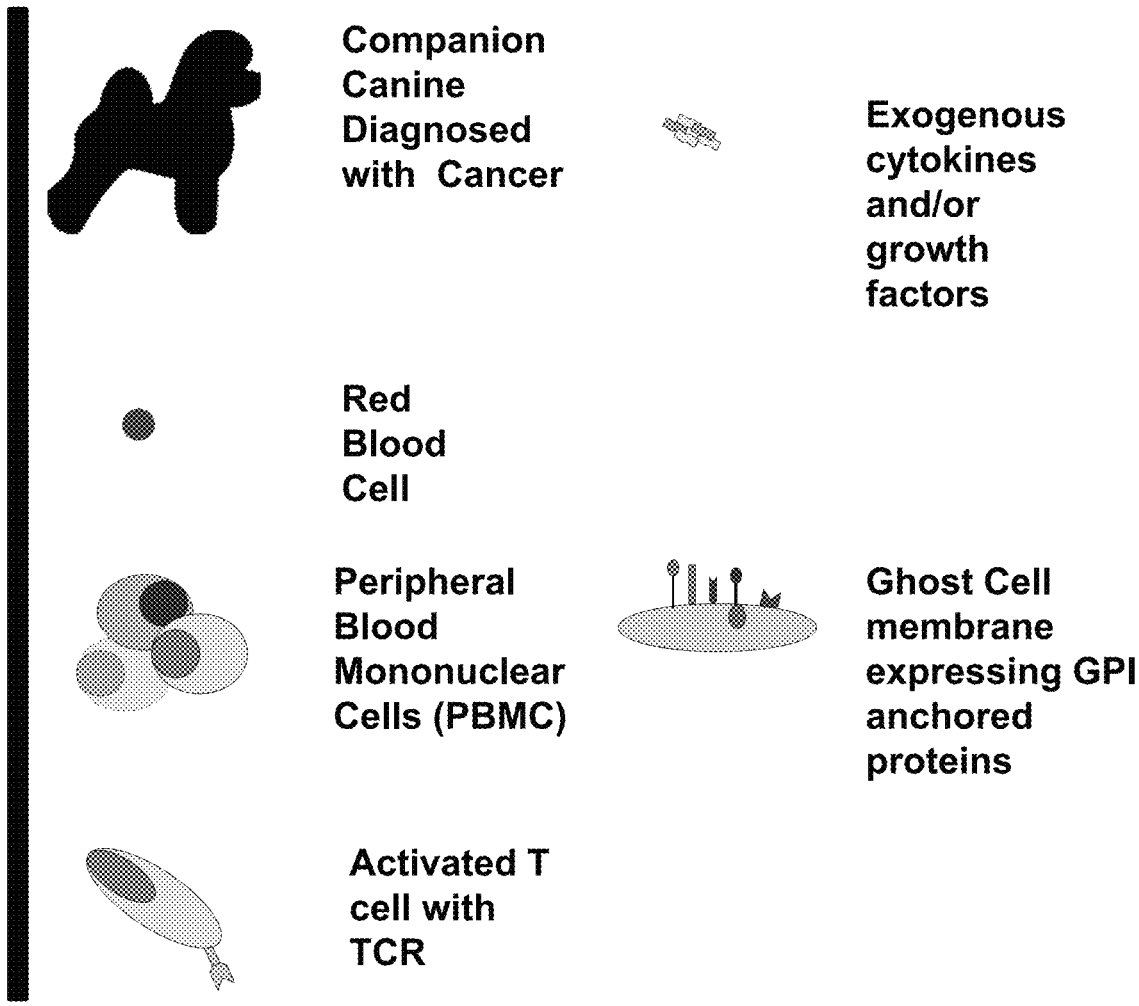
FIG. 4 con't

SEQUENCE LISTING

<160> NUMBER OF SEQ ID NOS: 258

<210> SEQ ID NO 1
<211> LENGTH: 576
<212> TYPE: DNA
<213> ORGANISM: Artificial Sequence
<220> FEATURE:
<223> OTHER INFORMATION: synthetic polynucleotides

<400> SEQUENCE: 1

```
tagtaatcaa ttacggggtc attagttcat agcccatata tggagttccg cgttacataa      60
cttacggtaa atggcccgcc tggctgaccg cccaacgacc cccgcccatt gacgtcaata     120
atgacgtatg ttcccatagt aacgccaata gggactttcc attgacgtca atgggtggag     180
```

-continued

| | | |
|---|---|---|
| tatttacggt aaactgccca cttggcagta catcaagtgt atcatatgcc aagtacgccc | 240 | |
| cctattgacg tcaatgacgg taaatggccc gcctggcatt atgcccagta catgacctta | 300 | |
| tgggactttc ctacttggca gtacatctac gtattagtca tcgctattac catggtgatg | 360 | |
| cggttttggc agtacatcaa tgggcgtgga tagcggtttg actcacgggg atttccaagt | 420 | |
| ctccacccca ttgacgtcaa tgggagtttg ttttggcacc aaaatcaacg ggactttcca | 480 | |
| aaatgtcgta acaactccgc cccattgacg caaatgggcg gtaggcgtgt acggtgggag | 540 | |
| gtctatataa gcagagctgg tttagtgaac cgtcag | 576 | |

<210> SEQ ID NO 2
<211> LENGTH: 13
<212> TYPE: DNA
<213> ORGANISM: Artificial Sequence
<220> FEATURE:
<223> OTHER INFORMATION: synthetic polynucleotide

<400> SEQUENCE: 2
gccgccgcca tgg                                                          13

<210> SEQ ID NO 3
<211> LENGTH: 277
<212> TYPE: PRT
<213> ORGANISM: Homo sapiens

<400> SEQUENCE: 3

Gln Val Asp Thr Thr Lys Ala Val Ile Thr Leu Gln Pro Pro Trp Val
1               5                   10                  15

Ser Val Phe Gln Glu Glu Thr Val Thr Leu His Cys Glu Val Leu His
                20                  25                  30

Leu Pro Gly Ser Ser Ser Thr Gln Trp Phe Leu Asn Gly Thr Ala Thr
            35                  40                  45

Gln Thr Ser Thr Pro Ser Tyr Arg Ile Thr Ser Ala Ser Val Asn Asp
        50                  55                  60

Ser Gly Glu Tyr Arg Cys Gln Arg Gly Leu Ser Gly Arg Ser Asp Pro
65                  70                  75                  80

Ile Gln Leu Glu Ile His Arg Gly Trp Leu Leu Leu Gln Val Ser Ser
                85                  90                  95

Arg Val Phe Thr Glu Gly Glu Pro Leu Ala Leu Arg Cys His Ala Trp
                100                 105                 110

Lys Asp Lys Leu Val Tyr Asn Val Leu Tyr Tyr Arg Asn Gly Lys Ala
            115                 120                 125

Phe Lys Phe Phe His Trp Asn Ser Asn Leu Thr Ile Leu Lys Thr Asn
        130                 135                 140

Ile Ser His Asn Gly Thr Tyr His Cys Ser Gly Met Gly Lys His Arg
145                 150                 155                 160

Tyr Thr Ser Ala Gly Ile Ser Val Thr Val Lys Glu Leu Phe Pro Ala
                165                 170                 175

Pro Val Leu Asn Ala Ser Val Thr Ser Pro Leu Leu Glu Gly Asn Leu
            180                 185                 190

Val Thr Leu Ser Cys Glu Thr Lys Leu Leu Leu Gln Arg Pro Gly Leu
        195                 200                 205

Gln Leu Tyr Phe Ser Phe Tyr Met Gly Ser Lys Thr Leu Arg Gly Arg
    210                 215                 220

Asn Thr Ser Ser Glu Tyr Gln Ile Leu Thr Ala Arg Arg Glu Asp Ser
225                 230                 235                 240

```
Gly Leu Tyr Trp Cys Glu Ala Ala Thr Glu Asp Gly Asn Val Leu Lys
                245                 250                 255

Arg Ser Pro Glu Leu Glu Leu Gln Val Leu Gly Leu Gln Leu Pro Thr
            260                 265                 270

Pro Val Trp Phe His
        275

<210> SEQ ID NO 4
<211> LENGTH: 224
<212> TYPE: PRT
<213> ORGANISM: Homo sapiens

<400> SEQUENCE: 4

Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile His His Lys Lys Pro Thr Gly
                85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
130                 135                 140

Lys Met Ser Val Leu Leu Arg Thr Lys Asn Ser Thr Ile Glu Tyr Asp
145                 150                 155                 160

Gly Val Met Gln Lys Ser Gln Asp Asn Val Thr Glu Leu Tyr Asp Val
                165                 170                 175

Ser Ile Ser Leu Ser Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp His Ile Pro
210                 215                 220

<210> SEQ ID NO 5
<211> LENGTH: 205
<212> TYPE: PRT
<213> ORGANISM: Homo sapiens

<400> SEQUENCE: 5

Ala Cys Pro Trp Ala Val Ser Gly Ala Arg Ala Ser Pro Gly Ser Ala
1               5                   10                  15

Ala Ser Pro Arg Leu Arg Glu Gly Pro Glu Leu Ser Pro Asp Asp Pro
            20                  25                  30

Ala Gly Leu Leu Asp Leu Arg Gln Gly Met Phe Ala Gln Leu Val Ala
        35                  40                  45

Gln Asn Val Leu Leu Ile Asp Gly Pro Leu Ser Trp Tyr Ser Asp Pro
50                  55                  60
```

Gly Leu Ala Gly Val Ser Leu Thr Gly Gly Leu Ser Tyr Lys Glu Asp
65                  70                  75                  80

Thr Lys Glu Leu Val Ala Lys Ala Gly Val Tyr Tyr Val Phe Phe
                85                  90                  95

Gln Leu Glu Leu Arg Arg Val Ala Gly Glu Gly Ser Gly Ser Val
            100                 105                 110

Ser Leu Ala Leu His Leu Gln Pro Leu Arg Ser Ala Ala Gly Ala Ala
            115                 120                 125

Ala Leu Ala Leu Thr Val Asp Leu Pro Pro Ala Ser Glu Ala Arg
    130                 135                 140

Asn Ser Ala Phe Gly Phe Gln Gly Arg Leu Leu His Leu Ser Ala Gly
145                 150                 155                 160

Gln Arg Leu Gly Val His Leu His Thr Glu Ala Arg Ala Arg His Ala
                165                 170                 175

Trp Gln Leu Thr Gln Gly Ala Thr Val Leu Gly Leu Phe Arg Val Thr
                180                 185                 190

Pro Glu Ile Pro Ala Gly Leu Pro Ser Pro Arg Ser Glu
                195                 200                 205

<210> SEQ ID NO 6
<211> LENGTH: 162
<212> TYPE: PRT
<213> ORGANISM: Homo sapiens

<400> SEQUENCE: 6

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
                20                  25                  30

Val Phe Ile Leu Gly Cys Phe Ser Ala Gly Leu Pro Lys Thr Glu Ala
            35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
130                 135                 140

Lys Glu Phe Leu Gln Ser Phe Val His Ile Val Gln Met Phe Ile Asn
145                 150                 155                 160

Thr Ser

<210> SEQ ID NO 7
<211> LENGTH: 31
<212> TYPE: PRT
<213> ORGANISM: Artificial Sequence
<220> FEATURE:
<223> OTHER INFORMATION: synthetic polypeptide

<400> SEQUENCE: 7

Thr Thr Ser Gly Thr Thr Arg Leu Leu Ser Gly His Thr Cys Phe Thr
1               5                   10                  15

Leu Thr Gly Leu Leu Gly Thr Leu Val Thr Met Gly Leu Leu Thr
            20                  25                  30

<210> SEQ ID NO 8
<211> LENGTH: 1500
<212> TYPE: DNA
<213> ORGANISM: Homo sapiens

<400> SEQUENCE: 8
agcgagctcc tcctccttcc cctccccact ctccccgagt ctagggcccc cggggcgtat    60
gacgccggag ccctctgacc gcacctctga ccacaacaaa ccctactcc acccgtcttg   120
tttgtcccac ccttggtgac gcagagcccc agcccagacc ccgcccaaag cactcattta   180
actggtattg cggagccacg aggcttctgc ttactgcaac tcgctccggc cgctgggcgt   240
agctgcgact cggcggagtc ccggcggcgc gtccttgttc taacccggcg cgccatgacc   300
gtcgcgcggc cgagcgtgcc cgcggcgctg cccctcctcg gggagctgcc ccggctgctg   360
ctgctggtgc tgttgtgcct gccggccgtg tggggtgact gtggccttcc cccagatgta   420
cctaatgccc agccagcttt ggaaggccgt acaagttttc ccgaggatac tgtaataacg   480
tacaaatgtg aagaaagctt tgtgaaaatt cctggcgaga aggactcagt gatctgcctt   540
aagggcagtc aatggtcaga tattgaagag ttctgcaatc gtagctgcga ggtgccaaca   600
aggctaaatt ctgcatccct caaacagcct tatatcactc agaattattt tccagtcggt   660
actgttgtgg aatatgagtg ccgtccaggt tacagaagag aaccttctct atcaccaaaa   720
ctaacttgcc ttcagaattt aaaatggtcc acagcagtcg aattttgtaa aagaaatca   780
tgccctaatc cgggagaaat acgaaatggt cagattgatg taccaggtgg catattattt   840
ggtgcaacca tctccttctc atgtaacaca gggtacaaat tatttggctc gacttctagt   900
ttttgtctta tttcaggcag ctctgtccag tggagtgacc cgttgccaga gtgcagagaa   960
atttattgtc cagcaccacc acaaattgac aatggaataa ttcaagggga acgtgaccat  1020
tatggatata gacagtctgt aacgtatgca tgtaataaag gattcaccat gattggagag  1080
cactctattt attgtactgt gaataatgat gaaggagagt ggagtggccc accacctgaa  1140
tgcagaggaa aatctctaac ttccaaggtc ccaccaacag ttcagaaacc taccacagta  1200
aatgttccaa ctacagaagt ctcaccaact tctcagaaaa ccaccacaaa accaccaca   1260
ccaaatgctc aagcaacacg gagtacacct gtttccagga caaccaagca ttttcatgaa  1320
acaaccccaa ataaaggaag tggaaccact tcaggtacta cccgtcttct atctgggcac  1380
acgtgtttca cgttgacagg tttgcttggg acgctagtaa ccatgggctt gctgacttag  1440
ccaaagaaga gttaagaaga aaatacacac aagtatacag actgttccta gtttcttaga  1500

<210> SEQ ID NO 9
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 9

Ala Ala Tyr Ala Ala Ala Ala Ala Leu
1               5

<210> SEQ ID NO 10
<211> LENGTH: 10
<212> TYPE: PRT

```
<213> ORGANISM: Artificial Sequence
<220> FEATURE:
<223> OTHER INFORMATION: synthetic polypeptide

<400> SEQUENCE: 10

Ala Tyr Ala Ala Gln Gly Tyr Lys Val Leu
1               5                   10

<210> SEQ ID NO 11
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 11

Phe Ala Val Pro Asn Leu Gln Ser Leu
1               5

<210> SEQ ID NO 12
<211> LENGTH: 14
<212> TYPE: PRT
<213> ORGANISM: Artificial Sequence
<220> FEATURE:
<223> OTHER INFORMATION: synthetic polypeptide

<400> SEQUENCE: 12

Phe Arg Asn Leu Ala Tyr Gly Arg Thr Cys Val Leu Gly Lys
1               5                   10

<210> SEQ ID NO 13
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 13

Phe Ser Tyr Met Asp Asp Val Val Leu
1               5

<210> SEQ ID NO 14
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 14

Phe Thr Pro Pro His Gly Gly Leu Leu
1               5

<210> SEQ ID NO 15
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 15

Phe Val Tyr Gly Gly Ser Lys Thr Ser Leu
1               5                   10

<210> SEQ ID NO 16
<211> LENGTH: 9
<212> TYPE: PRT
<213> ORGANISM: Artificial Sequence
```

<220> FEATURE:
<223> OTHER INFORMATION: synthetic polypeptide

<400> SEQUENCE: 16

Lys Gln Tyr Leu Asn Leu Tyr Pro Val
1               5

<210> SEQ ID NO 17
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 17

Met Val His Gln Ala Ile Ser Pro Arg
1               5

<210> SEQ ID NO 18
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 18

Pro Tyr Phe Val Arg Ala Gln Gly Leu Ile
1               5                   10

<210> SEQ ID NO 19
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 19

Gln Met Val His Gln Ala Ile Ser Pro Arg
1               5                   10

<210> SEQ ID NO 20
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 20

Val Met Ala Pro Arg Thr Leu Val Leu
1               5

<210> SEQ ID NO 21
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 21

Val Ser Phe Ile Glu Phe Val Gly Trp
1               5

<210> SEQ ID NO 22
<211> LENGTH: 9
<212> TYPE: PRT
<213> ORGANISM: Artificial Sequence
<220> FEATURE:

```
<223> OTHER INFORMATION: synthetic polypeptide

<400> SEQUENCE: 22

Phe Ala Tyr Asp Gly Lys Asp Tyr Ile
1               5

<210> SEQ ID NO 23
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 23

Phe Ala Tyr Asp Gly Lys Asp Tyr Leu
1               5

<210> SEQ ID NO 24
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 24

Phe Ala Met Pro Asn Phe Gln Thr Leu
1               5

<210> SEQ ID NO 25
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 25

Ala Ala Ala Asp Ala Ala Ala Ala Leu
1               5

<210> SEQ ID NO 26
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 26

Gly Ala Val Asp Pro Leu Leu Ala Leu
1               5

<210> SEQ ID NO 27
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 27

Gly Ala Val Asp Pro Leu Leu Lys Leu
1               5

<210> SEQ ID NO 28
<211> LENGTH: 9
<212> TYPE: PRT
<213> ORGANISM: Artificial Sequence
<220> FEATURE:
<223> OTHER INFORMATION: synthetic polypeptide
```

```
<400> SEQUENCE: 28

Gly Ala Val Asp Pro Leu Leu Ser Leu
1               5

<210> SEQ ID NO 29
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 29

Gly Ala Val Asp Pro Leu Leu Val Leu
1               5

<210> SEQ ID NO 30
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 30

Gly Ala Val Asp Pro Leu Leu Tyr Leu
1               5

<210> SEQ ID NO 31
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 31

Gln Ala Ile Ser Pro Arg Thr Leu
1               5

<210> SEQ ID NO 32
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 32

Thr Ala Met Asp Val Val Tyr Ala Leu
1               5

<210> SEQ ID NO 33
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 33

Ala Ala Met Pro Asn Phe Gln Thr Ala
1               5

<210> SEQ ID NO 34
<211> LENGTH: 9
<212> TYPE: PRT
<213> ORGANISM: Artificial Sequence
<220> FEATURE:
<223> OTHER INFORMATION: synthetic polypeptide
```

```
<400> SEQUENCE: 34

Ala Ala Met Pro Asn Phe Gln Thr Leu
1               5

<210> SEQ ID NO 35
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 35

Ala Gln Ala Ile Ser Pro Arg Thr Leu
1               5

<210> SEQ ID NO 36
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 36

Phe Ala Ala Ile Ser Pro Arg Thr Leu
1               5

<210> SEQ ID NO 37
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 37

Phe Ala Ala Pro Asn Phe Gln Thr Ala
1               5

<210> SEQ ID NO 38
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 38

Phe Ala Ala Pro Asn Phe Gln Thr Leu
1               5

<210> SEQ ID NO 39
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 39

Phe Ala Gly Ile Ser Pro Arg Thr Leu
1               5

<210> SEQ ID NO 40
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 40
```

Phe Ala Met Ala Asn Phe Gln Thr Ala
1               5

<210> SEQ ID NO 41
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 41

Phe Ala Met Ala Asn Phe Gln Thr Leu
1               5

<210> SEQ ID NO 42
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 42

Phe Ala Met Pro Ala Phe Gln Thr Ala
1               5

<210> SEQ ID NO 43
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 43

Phe Ala Met Pro Ala Phe Gln Thr Leu
1               5

<210> SEQ ID NO 44
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 44

Phe Ala Met Pro Asn Ala Gln Thr Ala
1               5

<210> SEQ ID NO 45
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 45

Phe Ala Met Pro Asn Ala Gln Thr Leu
1               5

<210> SEQ ID NO 46
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 46

```
Phe Ala Met Pro Asn Phe Ala Thr Ala
1               5

<210> SEQ ID NO 47
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 47

Phe Ala Met Pro Asn Phe Ala Thr Leu
1               5

<210> SEQ ID NO 48
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 48

Phe Ala Met Pro Asn Phe Gln Ala Ala
1               5

<210> SEQ ID NO 49
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 49

Phe Ala Met Pro Asn Phe Gln Ala Leu
1               5

<210> SEQ ID NO 50
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 50

Phe Ala Met Pro Asn Phe Gln Thr Ala
1               5

<210> SEQ ID NO 51
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 51

Phe Ala Met Pro Asn Leu Gln Thr Ala
1               5

<210> SEQ ID NO 52
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 52

Phe Ala Met Pro Asn Leu Gln Thr Leu
```

1               5

<210> SEQ ID NO 53
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 53

Phe Gly Met Pro Asn Phe Gln Thr Ala
1               5

<210> SEQ ID NO 54
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 54

Phe Gly Met Pro Asn Phe Gln Thr Leu
1               5

<210> SEQ ID NO 55
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 55

Phe Gly Met Pro Asn Phe Gln Thr Met
1               5

<210> SEQ ID NO 56
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 56

Phe Gln Ala Ile Ser Pro Arg Thr Leu
1               5

<210> SEQ ID NO 57
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 57

Phe Val Met Pro Asn Phe Gln Thr Ala
1               5

<210> SEQ ID NO 58
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 58

Phe Val Met Pro Asn Phe Gln Thr Leu
1               5

<210> SEQ ID NO 59
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 59

Gly Gln Met Val His Gln Ala Ile
1               5

<210> SEQ ID NO 60
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 60

Gly Gln Met Val His Gln Ala Ile Ser
1               5

<210> SEQ ID NO 61
<211> LENGTH: 12
<212> TYPE: PRT
<213> ORGANISM: Artificial Sequence
<220> FEATURE:
<223> OTHER INFORMATION: synthetic polypeptide

<400> SEQUENCE: 61

Gly Gln Met Val His Gln Ala Ile Ser Pro Arg Thr
1               5                   10

<210> SEQ ID NO 62
<211> LENGTH: 13
<212> TYPE: PRT
<213> ORGANISM: Artificial Sequence
<220> FEATURE:
<223> OTHER INFORMATION: synthetic polypeptide

<400> SEQUENCE: 62

Gly Gln Met Val His Gln Ala Ile Ser Pro Arg Thr Leu
1               5                   10

<210> SEQ ID NO 63
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 63

His Ala Ala Ile Ser Pro Arg Thr Leu
1               5

<210> SEQ ID NO 64
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 64

His Ala Gly Ile Ser Pro Arg Thr Leu
1               5

```
<210> SEQ ID NO 65
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 65

His Ala Met Pro Asn Phe Gln Thr Ala
1               5

<210> SEQ ID NO 66
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 66

His Ala Met Pro Asn Phe Gln Thr Leu
1               5

<210> SEQ ID NO 67
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 67

His Gln Ala Ala Ser Pro Arg Thr Leu
1               5

<210> SEQ ID NO 68
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 68

His Gln Ala Ile Gly Pro Arg Thr Leu
1               5

<210> SEQ ID NO 69
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 69

His Gln Ala Ile Ser Ala Arg Thr Leu
1               5

<210> SEQ ID NO 70
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 70

His Gln Ala Ile Ser Pro Ala Thr Leu
1               5
```

```
<210> SEQ ID NO 71
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 71

His Gln Ala Ile Ser Pro Arg Ala Leu
1               5

<210> SEQ ID NO 72
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 72

His Gln Ala Ile Ser Pro Arg Thr
1               5

<210> SEQ ID NO 73
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 73

His Gln Ala Ile Ser Pro Arg Thr Ala
1               5

<210> SEQ ID NO 74
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 74

His Gln Ala Ile Ser Pro Arg Thr Asp
1               5

<210> SEQ ID NO 75
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 75

His Gln Ala Ile Ser Pro Arg Thr Phe
1               5

<210> SEQ ID NO 76
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 76

His Gln Ala Ile Ser Pro Arg Thr Lys
1               5

<210> SEQ ID NO 77
```

```
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 77

His Gln Ala Ile Ser Pro Arg Thr Leu
1               5

<210> SEQ ID NO 78
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 78

His Gln Ala Ile Ser Pro Arg Thr Met
1               5

<210> SEQ ID NO 79
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 79

His Gln Asp Ile Ser Pro Arg Thr Leu
1               5

<210> SEQ ID NO 80
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 80

His Gln Gly Ile Ser Pro Arg Thr Leu
1               5

<210> SEQ ID NO 81
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 81

His Gln Lys Ile Ser Pro Arg Thr Leu
1               5

<210> SEQ ID NO 82
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 82

His Gln Leu Ile Ser Pro Arg Thr Leu
1               5

<210> SEQ ID NO 83
<211> LENGTH: 9
```

```
<212> TYPE: PRT
<213> ORGANISM: Artificial Sequence
<220> FEATURE:
<223> OTHER INFORMATION: synthetic polypeptide

<400> SEQUENCE: 83

His Gln Pro Ile Ser Pro Arg Thr Leu
1               5

<210> SEQ ID NO 84
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 84

His Gln Ser Ile Ser Pro Arg Thr Leu
1               5

<210> SEQ ID NO 85
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 85

Leu Ala Met Pro Asn Phe Gln Thr Ala
1               5

<210> SEQ ID NO 86
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 86

Leu Ala Met Pro Asn Phe Gln Thr Leu
1               5

<210> SEQ ID NO 87
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 87

Met Val His Gln Ala Ile Ser Pro Arg Thr
1               5                   10

<210> SEQ ID NO 88
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 88

Gln Met Val His Gln Ala Ile Ser
1               5

<210> SEQ ID NO 89
<211> LENGTH: 8
<212> TYPE: PRT
```

<213> ORGANISM: Artificial Sequence
<220> FEATURE:
<223> OTHER INFORMATION: synthetic polypeptide

<400> SEQUENCE: 89

Val His Gln Ala Ile Ser Pro Arg
1               5

<210> SEQ ID NO 90
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 90

Val His Gln Ala Ile Ser Pro Arg Thr
1               5

<210> SEQ ID NO 91
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 91

Val His Gln Ala Ile Ser Pro Arg Thr Leu
1               5                   10

<210> SEQ ID NO 92
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 92

Ala Gln Phe Glu His Thr Ile Leu Leu
1               5

<210> SEQ ID NO 93
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 93

Phe Gln Asn Pro Phe Arg Ser Glu Leu
1               5

<210> SEQ ID NO 94
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 94

Lys Ser Met Glu Thr Lys Val Gln Phe
1               5

<210> SEQ ID NO 95
<211> LENGTH: 10
<212> TYPE: PRT
<213> ORGANISM: Artificial Sequence

```
<220> FEATURE:
<223> OTHER INFORMATION: synthetic polypeptide

<400> SEQUENCE: 95

Arg Leu Tyr Pro Glu Gly Leu Ala Gln Leu
1               5                   10

<210> SEQ ID NO 96
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 96

Tyr Ala Tyr Asp Gly Lys Asp Tyr Ile Ala Leu
1               5                   10

<210> SEQ ID NO 97
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 97

Phe Ser Ser Ala Gly Pro Cys Ala Leu
1               5

<210> SEQ ID NO 98
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 98

Phe Thr Gly Leu Tyr Ser Ser Thr Val
1               5

<210> SEQ ID NO 99
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 99

Phe Thr Gln Cys Gly Tyr Pro Ala Leu
1               5

<210> SEQ ID NO 100
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 100

Phe Thr Ser Ala Ile Cys Ser Val Val
1               5

<210> SEQ ID NO 101
<211> LENGTH: 9
<212> TYPE: PRT
<213> ORGANISM: Artificial Sequence
<220> FEATURE:
```

<223> OTHER INFORMATION: synthetic polypeptide

<400> SEQUENCE: 101

Gly Thr Phe Val Ser Pro Leu Pro Ile
1               5

<210> SEQ ID NO 102
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 102

Lys Ser Val Gln His Leu Glu Ser Leu
1               5

<210> SEQ ID NO 103
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 103

Leu Gln Asp Pro Arg Val Arg Ala Leu
1               5

<210> SEQ ID NO 104
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 104

Leu Ser Leu Asp Val Ser Ala Ala Phe
1               5

<210> SEQ ID NO 105
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 105

Leu Ser Pro Thr Val Trp Leu Ser Val
1               5

<210> SEQ ID NO 106
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 106

Leu Ser Tyr Gln His Phe Arg Lys Leu
1               5

<210> SEQ ID NO 107
<211> LENGTH: 9
<212> TYPE: PRT
<213> ORGANISM: Artificial Sequence
<220> FEATURE:
<223> OTHER INFORMATION: synthetic polypeptide

```
<400> SEQUENCE: 107

Met Ala Ala Arg Leu Cys Cys Gln Leu
1               5

<210> SEQ ID NO 108
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 108

Met Met Trp Phe Trp Gly Pro Ser Leu
1               5

<210> SEQ ID NO 109
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 109

Arg Ala Phe Pro His Cys Leu Ala Phe
1               5

<210> SEQ ID NO 110
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 110

Ser Ala Ala Phe Tyr His Leu Pro Leu
1               5

<210> SEQ ID NO 111
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 111

Val Ser Ile Pro Trp Thr His Lys Val
1               5

<210> SEQ ID NO 112
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 112

Tyr Ala Ala Val Thr Asn Phe Leu Leu
1               5

<210> SEQ ID NO 113
<211> LENGTH: 10
<212> TYPE: PRT
<213> ORGANISM: Artificial Sequence
<220> FEATURE:
<223> OTHER INFORMATION: synthetic polypeptide
```

```
<400> SEQUENCE: 113

Arg Val Ala Pro Glu Glu His Pro Val Leu
1               5                   10

<210> SEQ ID NO 114
<211> LENGTH: 10
<212> TYPE: PRT
<213> ORGANISM: Artificial Sequence
<220> FEATURE:
<223> OTHER INFORMATION: synthetic polypeptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 114

Phe Val Tyr Gly Xaa Ser Lys Thr Ser Leu
1               5                   10

<210> SEQ ID NO 115
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 115

Ala Leu Arg Asp Val Ser Glu Glu Leu
1               5

<210> SEQ ID NO 116
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 116

Phe Leu Ala Glu His Pro Asn Val Thr Leu
1               5                   10

<210> SEQ ID NO 117
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 117

Phe Leu Asp Lys Asn Asp His Ser Leu
1               5

<210> SEQ ID NO 118
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 118

Phe Leu Ser Glu His Pro Asn Val Thr Leu
1               5                   10

<210> SEQ ID NO 119
<211> LENGTH: 10
<212> TYPE: PRT
<213> ORGANISM: Artificial Sequence
```

<220> FEATURE:
<223> OTHER INFORMATION: synthetic polypeptide

<400> SEQUENCE: 119

Leu Leu Tyr Gln Gly Pro His Asn Thr Leu
1               5                   10

<210> SEQ ID NO 120
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 120

Leu Met Ala Glu Met Gly Val His Ser Val
1               5                   10

<210> SEQ ID NO 121
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 121

Arg Met Leu Asp Ser Val Glu Lys Leu
1               5

<210> SEQ ID NO 122
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 122

Arg Val Pro Pro Pro Pro Gln Ser Val
1               5

<210> SEQ ID NO 123
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 123

Tyr Ala Tyr Glu Lys Pro His Val Val
1               5

<210> SEQ ID NO 124
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 124

Tyr Met Tyr Glu Lys Glu Ser Glu Leu
1               5

<210> SEQ ID NO 125
<211> LENGTH: 8
<212> TYPE: PRT
<213> ORGANISM: Artificial Sequence
<220> FEATURE:

```
<223> OTHER INFORMATION: synthetic polypeptide

<400> SEQUENCE: 125

Ile Ser Leu Glu Gly Lys Pro Leu
1               5

<210> SEQ ID NO 126
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 126

Phe Ile Ala Pro Thr Gly His Ser Leu
1               5

<210> SEQ ID NO 127
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 127

Asn Thr Ile Asp Pro Ser His Pro Met
1               5

<210> SEQ ID NO 128
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 128

Phe Ala His Pro Tyr Gln Tyr Glu Leu
1               5

<210> SEQ ID NO 129
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 129

Thr Gly Tyr Ile Lys Thr Glu Leu
1               5

<210> SEQ ID NO 130
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 130

Val Ala Thr Glu Gly Ser Arg Glu Leu
1               5

<210> SEQ ID NO 131
<211> LENGTH: 9
<212> TYPE: PRT
<213> ORGANISM: Artificial Sequence
<220> FEATURE:
<223> OTHER INFORMATION: synthetic polypeptide
```

```
<400> SEQUENCE: 131

Tyr Gly Phe Glu Lys Pro Ser Ala Ile
1               5

<210> SEQ ID NO 132
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 132

Tyr Gly Asn Pro Arg Thr Asn Gly Met
1               5

<210> SEQ ID NO 133
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 133

Phe Thr Asp Glu Glu Ser Arg Val Phe
1               5

<210> SEQ ID NO 134
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 134

Ile Pro Asn Glu Ile Ile His Ala Leu
1               5

<210> SEQ ID NO 135
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 135

Ala Ala Val Asp Ala Gly Met Ala Met
1               5

<210> SEQ ID NO 136
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 136

Phe Ala Tyr Asp Gly Lys Asp Tyr Leu Thr Leu
1               5                   10

<210> SEQ ID NO 137
<211> LENGTH: 10
<212> TYPE: PRT
<213> ORGANISM: Artificial Sequence
<220> FEATURE:
<223> OTHER INFORMATION: synthetic polypeptide
```

```
<400> SEQUENCE: 137

Leu Ala Val His Pro Ser Gly Val Ala Leu
1               5                   10

<210> SEQ ID NO 138
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 138

Ala Ala Ala Ala Ala Ala Ala Ala Leu
1               5

<210> SEQ ID NO 139
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 139

Ala Ala Tyr Asp Ala Ala Ala Ala Ala
1               5

<210> SEQ ID NO 140
<211> LENGTH: 12
<212> TYPE: PRT
<213> ORGANISM: Artificial Sequence
<220> FEATURE:
<223> OTHER INFORMATION: synthetic polypeptide

<400> SEQUENCE: 140

Ala Ala Tyr Asp Ala Ala Ala Ala Ala Ala Ala Leu
1               5                   10

<210> SEQ ID NO 141
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 141

Ala Ala Tyr Asp Ala Ala Ala Ala Ala Ala Leu
1               5                   10

<210> SEQ ID NO 142
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 142

Ala Ala Tyr Asp Ala Ala Ala Ala Ala Leu
1               5                   10

<210> SEQ ID NO 143
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 143
```

```
Ala Ala Tyr Asp Ala Ala Ala Ala Leu
1               5
```

<210> SEQ ID NO 144
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 144

```
Ala Ala Tyr Asp Ala Ala Ala Leu
1               5
```

<210> SEQ ID NO 145
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 145

```
Phe Ala Tyr Asp Gly Lys Asp Tyr Ile Ala Leu
1               5                   10
```

<210> SEQ ID NO 146
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 146

```
Gly Ala Val Asp Pro Leu Lys Ala Leu
1               5
```

<210> SEQ ID NO 147
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 147

```
Ile Ala Ala Gly Ile Phe Asn Asp Leu
1               5
```

<210> SEQ ID NO 148
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 148

```
Ile Ala Ile Asp Pro Ser Lys Lys Leu
1               5
```

<210> SEQ ID NO 149
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 149

```
Ile Ala Ile Ile Pro Ser Lys Ala Leu
1               5

<210> SEQ ID NO 150
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 150

Ile Ala Ile Ile Pro Ser Lys Lys Leu
1               5

<210> SEQ ID NO 151
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 151

Pro Ala Ala Ala Ala Phe Asp Leu
1               5

<210> SEQ ID NO 152
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 152

Thr Ala Met Asp Val Val Tyr Lys Leu
1               5

<210> SEQ ID NO 153
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 153

Val Ala Tyr Glu Ala Pro Ser Leu
1               5

<210> SEQ ID NO 154
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 154

Val Thr Asp Ser Gly Pro Thr Phe Asn Tyr Leu
1               5                   10

<210> SEQ ID NO 155
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 155

Ala Ala Ala Tyr Pro His Thr Ser Leu
```

```
1               5
```

<210> SEQ ID NO 156
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 156

```
Ala Ala Met Lys Ala Leu Gln Ala Leu
1               5
```

<210> SEQ ID NO 157
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 157

```
Ala Ala Val Asp Arg Thr Thr Glu Leu
1               5
```

<210> SEQ ID NO 158
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 158

```
Ala Ala Val Pro Arg Ala Ala Phe Leu
1               5
```

<210> SEQ ID NO 159
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 159

```
Ala Leu Ala Pro Gly Val Arg Ala Val
1               5
```

<210> SEQ ID NO 160
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 160

```
Ala Leu Phe Gln His Ile Thr Ala Leu
1               5
```

<210> SEQ ID NO 161
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 161

```
Ala Leu Asn Pro Val Ala Asn Phe His Leu
1               5                  10
```

```
<210> SEQ ID NO 162
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 162

Ala Val Met Leu His Ser Phe Thr Leu
1               5

<210> SEQ ID NO 163
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 163

Phe Ala Ala Leu His Gly Pro Ala Leu
1               5

<210> SEQ ID NO 164
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 164

Phe Ala Asp Gly His Val Leu Glu Leu
1               5

<210> SEQ ID NO 165
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 165

Phe Ala Asp Pro His Gly Lys Val Phe
1               5

<210> SEQ ID NO 166
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 166

Phe Ala Glu Asp Ser Leu Arg Val Ile
1               5

<210> SEQ ID NO 167
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 167

Phe Ala Glu Gly Phe Val Arg Ala Leu
1               5
```

<210> SEQ ID NO 168
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 168

Phe Ala Glu Gly Gln Gly Arg Ala Leu
1               5

<210> SEQ ID NO 169
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 169

Phe Ala Gly Pro His Ser Thr Leu
1               5

<210> SEQ ID NO 170
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 170

Phe Ala Gly Trp Gly Arg Ala Leu
1               5

<210> SEQ ID NO 171
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 171

Phe Ala Ile Asp Pro His Leu Leu Leu
1               5

<210> SEQ ID NO 172
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 172

Phe Ala Met Ile Pro Ala Lys Glu Ala
1               5

<210> SEQ ID NO 173
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 173

Phe Ala Ser Glu Leu Ser Arg Ser Leu
1               5

<210> SEQ ID NO 174
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 174

Phe Ala Val Ile Ala His Val Gly Met
1               5

<210> SEQ ID NO 175
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 175

Phe Ala Val Ile Ser Arg His Ser Leu
1               5

<210> SEQ ID NO 176
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 176

Phe Ala Tyr Glu Gly Thr Arg Asp Ser Gly Met
1               5                   10

<210> SEQ ID NO 177
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 177

Phe Gly Ile Asp Arg Pro Ala Glu Leu
1               5

<210> SEQ ID NO 178
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 178

Phe Gly Gln Leu Gly Arg Glu Leu
1               5

<210> SEQ ID NO 179
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 179

Phe Ile Glu Asp Ala Val His Val Leu
1               5

<210> SEQ ID NO 180

```
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 180

Phe Leu Ala Asp Asn His His Gln Val
1               5

<210> SEQ ID NO 181
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 181

Phe Leu Asp Glu Lys Thr His Glu Leu
1               5

<210> SEQ ID NO 182
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 182

Phe Asn Asp Pro Asn Ala Lys Glu Met
1               5

<210> SEQ ID NO 183
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 183

Phe Asn Phe Val Gly Lys Ile Leu
1               5

<210> SEQ ID NO 184
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 184

Phe Gln His Val Gly Gln Thr Leu
1               5

<210> SEQ ID NO 185
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 185

Phe Ser His Pro Arg Glu Pro Ala Leu
1               5

<210> SEQ ID NO 186
<211> LENGTH: 8
```

```
<212> TYPE: PRT
<213> ORGANISM: Artificial Sequence
<220> FEATURE:
<223> OTHER INFORMATION: synthetic polypeptide

<400> SEQUENCE: 186

Phe Ser Lys Ile Gly Gly Ile Leu
1               5

<210> SEQ ID NO 187
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 187

Phe Ser Ser Ala Asn Ser Pro Phe Leu
1               5

<210> SEQ ID NO 188
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 188

Phe Thr Val Pro His Thr His Val Phe
1               5

<210> SEQ ID NO 189
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 189

Phe Val Ile Glu Thr Ala Arg Gln Leu
1               5

<210> SEQ ID NO 190
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 190

Phe Val Asn Pro His Val Ser Ser Phe
1               5

<210> SEQ ID NO 191
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 191

Gly Ile His Glu Thr Thr Phe Asn Ser Ile Met
1               5                   10

<210> SEQ ID NO 192
<211> LENGTH: 9
<212> TYPE: PRT
```

```
<213> ORGANISM: Artificial Sequence
<220> FEATURE:
<223> OTHER INFORMATION: synthetic polypeptide

<400> SEQUENCE: 192

Gly Gln Tyr Pro Arg Ala Leu Glu Leu
1               5

<210> SEQ ID NO 193
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 193

His Ala Phe Leu Lys Thr Glu Phe
1               5

<210> SEQ ID NO 194
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 194

His Ala Tyr Leu Ser Lys Asn Ser Leu
1               5

<210> SEQ ID NO 195
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 195

Ile Ala Ala Pro Phe Thr Ser Lys Leu
1               5

<210> SEQ ID NO 196
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 196

Ile Ala Gln Pro Val Arg Ser Phe Leu
1               5

<210> SEQ ID NO 197
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 197

Ile Ala Thr Tyr Arg Thr Leu Leu
1               5

<210> SEQ ID NO 198
<211> LENGTH: 9
<212> TYPE: PRT
<213> ORGANISM: Artificial Sequence
```

```
<220> FEATURE:
<223> OTHER INFORMATION: synthetic polypeptide

<400> SEQUENCE: 198

Ile Leu Gln Pro His Val Ile Ala Leu
1               5

<210> SEQ ID NO 199
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 199

Ile Met Asn Asp Ile Pro Ile Arg Leu
1               5

<210> SEQ ID NO 200
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 200

Ile Gln Asp Asp Met His Leu Val Ile
1               5

<210> SEQ ID NO 201
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 201

Ile Ser Glu Glu Asn Phe Arg Val Met
1               5

<210> SEQ ID NO 202
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 202

Ile Val Ile Asp Pro Lys Asn Pro Leu
1               5

<210> SEQ ID NO 203
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 203

Lys Ala Phe Asp Tyr Pro Ser Arg Phe
1               5

<210> SEQ ID NO 204
<211> LENGTH: 8
<212> TYPE: PRT
<213> ORGANISM: Artificial Sequence
<220> FEATURE:
```

<223> OTHER INFORMATION: synthetic polypeptide

<400> SEQUENCE: 204

Lys Ala His Leu Gly Thr Ala Leu
1               5

<210> SEQ ID NO 205
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 205

Lys Ala Trp Glu Asn Ser Pro Asn Val
1               5

<210> SEQ ID NO 206
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 206

Lys Ile Ala Pro Asn Thr Pro Gln Leu
1               5

<210> SEQ ID NO 207
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 207

Lys Met Trp Glu Asn Arg Gln Asn Leu
1               5

<210> SEQ ID NO 208
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 208

Lys Gln Met Glu Gln Ile Ser Gln Phe Leu
1               5                   10

<210> SEQ ID NO 209
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 209

Lys Val Ala Pro Ala Pro Ala Val Val
1               5

<210> SEQ ID NO 210
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 210

Lys Val Ile Asp Gly Leu Glu Thr Leu
1               5

<210> SEQ ID NO 211
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 211

Lys Val Tyr Glu Arg Ala Val Glu Phe
1               5

<210> SEQ ID NO 212
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 212

Leu Ala Asp Pro Val Phe Arg Thr Leu
1               5

<210> SEQ ID NO 213
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 213

Leu Ala Leu Thr Arg Ser Ser Ser Leu
1               5

<210> SEQ ID NO 214
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 214

Leu Ala Met Arg Pro Leu Ala Ser Leu
1               5

<210> SEQ ID NO 215
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 215

Leu Ala Val Asp Lys Ser Ala Ser Leu
1               5

<210> SEQ ID NO 216
<211> LENGTH: 10
<212> TYPE: PRT
<213> ORGANISM: Artificial Sequence
<220> FEATURE:
<223> OTHER INFORMATION: synthetic polypeptide

```
<400> SEQUENCE: 216

Leu Ala Tyr Pro Ala Arg Pro Ala Gln Leu
1               5                   10

<210> SEQ ID NO 217
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 217

Leu Ile Val Glu Pro Ser Arg Glu Leu
1               5

<210> SEQ ID NO 218
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 218

Met Ala Asp Pro Asn Ile Arg Phe Leu
1               5

<210> SEQ ID NO 219
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 219

Met Val Ile Val Pro Thr Arg Glu Leu
1               5

<210> SEQ ID NO 220
<211> LENGTH: 14
<212> TYPE: PRT
<213> ORGANISM: Artificial Sequence
<220> FEATURE:
<223> OTHER INFORMATION: synthetic polypeptide

<400> SEQUENCE: 220

Asn Gln Tyr Ala Tyr Asp Gly Lys Asp Tyr Ile Ala Leu Asn
1               5                   10

<210> SEQ ID NO 221
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 221

Arg Ala Phe Pro Tyr Gly Asn Val Ala Phe
1               5                   10

<210> SEQ ID NO 222
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 222
```

Arg Leu Phe Glu Ser Ser Gln Tyr Leu
1               5

<210> SEQ ID NO 223
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 223

Arg Leu Tyr Gln Gly Ile Asn Gln Leu
1               5

<210> SEQ ID NO 224
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 224

Arg Val Trp Asp Ala Glu His Pro Gly Leu
1               5                   10

<210> SEQ ID NO 225
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 225

Ser Ala Phe Asp His Phe Ala Ser Val
1               5

<210> SEQ ID NO 226
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 226

Ser Ala Ile Gly Arg Ala Met Glu Leu
1               5

<210> SEQ ID NO 227
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 227

Ser Ala Ile Gly Tyr Ile His Ser Leu
1               5

<210> SEQ ID NO 228
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 228

```
Ser Ala Ile Pro His Pro Leu Ile Met
1               5
```

<210> SEQ ID NO 229
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 229

```
Ser Ala Tyr Glu Arg Ser Met Met
1               5
```

<210> SEQ ID NO 230
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 230

```
Thr Gln Leu Gly Pro Pro Tyr His Ile Leu
1               5                   10
```

<210> SEQ ID NO 231
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 231

```
Val Ala Asp Thr Val Ala Arg Val Leu
1               5
```

<210> SEQ ID NO 232
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 232

```
Val Ala Glu Glu Ser Arg Gln Val Leu
1               5
```

<210> SEQ ID NO 233
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 233

```
Val Ala Met Gly Tyr Ser His Ser Leu
1               5
```

<210> SEQ ID NO 234
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 234

```
Val Ala Tyr Leu Gln Ala His Ala Leu
```

<210> SEQ ID NO 235
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 235

Val Gly Asp Pro Ser Val His Leu Leu
1               5

<210> SEQ ID NO 236
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 236

Val Ile Tyr Pro Ala Arg Ile Ser Leu
1               5

<210> SEQ ID NO 237
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 237

Val Ser Gln Val Gly Lys Glu Leu
1               5

<210> SEQ ID NO 238
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 238

Val Thr Asp Pro Thr Gly Phe Leu Arg Met
1               5                   10

<210> SEQ ID NO 239
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 239

Val Thr Val Arg Pro Gly Leu Ala Met
1               5

<210> SEQ ID NO 240
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 240

Val Val Met Asn Val Val His Gln Leu
1               5

<210> SEQ ID NO 241
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 241

Val Val Met Pro Ile Ala His Glu Phe
1               5

<210> SEQ ID NO 242
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 242

Val Val Val Ala Val Gly Arg Ala Leu
1               5

<210> SEQ ID NO 243
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 243

Tyr Ala Asp Pro Thr Lys Arg Leu Glu Leu
1               5                   10

<210> SEQ ID NO 244
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 244

Tyr Ala Glu Val Gly Arg Val Leu
1               5

<210> SEQ ID NO 245
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 245

Tyr Ala Met Asp Tyr Ser Asn Lys Ala Leu
1               5                   10

<210> SEQ ID NO 246
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 246

Tyr Ala Tyr Asp Gly Lys Asp Tyr Leu Ala Leu
1               5                   10

<210> SEQ ID NO 247
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 247

Tyr Gly Thr Arg Tyr Gly Ala Ser Leu
1               5

<210> SEQ ID NO 248
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 248

Tyr Gly Tyr Gly His Glu Ser Glu Leu
1               5

<210> SEQ ID NO 249
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 249

Tyr Gln Met Glu Lys Asp Ile Ala Met
1               5

<210> SEQ ID NO 250
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 250

Tyr Ser Asp Asp Ile Pro His Ala Leu
1               5

<210> SEQ ID NO 251
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 251

Tyr Ser His Asp Gly Ala Phe Leu
1               5

<210> SEQ ID NO 252
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 252

Tyr Ser Leu Asp His Ile Ser Ser Leu
1               5

```
<210> SEQ ID NO 253
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 253

Tyr Ser Asn Arg Val Val Asp Leu
1               5

<210> SEQ ID NO 254
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 254

Tyr Thr Tyr Thr Ser Lys Ala Leu
1               5

<210> SEQ ID NO 255
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 255

Ala Val Arg Asp Leu Glu Arg Ala Met
1               5

<210> SEQ ID NO 256
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 256

Ala Ala Thr Ala Thr Phe Ala Ala Ala
1               5

<210> SEQ ID NO 257
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 257

Phe Ser Ile Asp Ser Pro Asp Ser Leu
1               5

<210> SEQ ID NO 258
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 258

Val Val Pro Glu Pro Gly Gln Pro Leu
1               5
```

COMPOSITIONS AND METHODS FOR TREATING IMMUNOLOGICAL DYSFUNCTION

CROSS-REFERENCE TO RELATED APPLICATIONS

This application claims the benefit of priority of U.S. Provisional Application No. 62/187,493, filed Jul. 1, 2015, the contents of which are hereby incorporated by reference.

SEQUENCE LISTING

The instant application contains a Sequence Listing which has been submitted in ASCII format via EFS-Web and is hereby incorporated by reference in its entirety. Said ASCII copy, created on Aug. 10, 2016, is named COOC-001_001US_Seq_Listing and is 60 KB in size.

FIELD OF THE INVENTION

The present invention relates to immunotherapy. In particular the invention provides methods of activating and expanding immune cell populations ex vivo and the use of the cells to treat immunological dysfunctions such as cancer, infection and autoimmune disorders.

BACKGROUND OF THE INVENTION

The immune system is designed to eradicate a large number of pathogens, as well as tumors, with minimal immunopathology. When the immune system becomes defective, however, numerous disease states result. Immunotherapy is a treatment modality that seeks to harness the power of the human immune system to treat disease.

One immunotherapy method is a type of cell therapy called adoptive immunotherapy. Adoptive immunotherapy is a cell therapy that involves the removal of immune cells from a subject, the ex-vivo processing (i.e., activation, purification and/or expansion of the cells) and the subsequent infusion of the resulting cells back into the same or different subject. Adoptive immunotherapy, which involves the transfer of autologous antigen-specific T cells generated ex vivo, is a promising strategy to treat cancer.

There is a need for cancer immunotherapy that provides protective and therapeutic immunity to a wide variety of tumor types. Current, adoptive immunotherapy treatments have infrequent and sporadic efficacy. Thus, there is a need to identify and solve these problems in order to increase the efficacy of adoptive immunotherapy protocols.

SUMMARY OF THE INVENTION

In various aspects the invention provides a ghost cell trainer (GHT) with a plasma membrane having a plurality of major histocompatibility complex (MHC) molecules; and a plurality of a protein of interest. The protein is glycosylphosphatidylinositol (GPI) anchored on the cell surface.

The invention also provides a ghost cell (GHC), having the following characteristics, is substantially free of all intracellular components and a plasma membrane having a plurality of MHC molecules and a plurality of a protein of interest. The protein is GPI anchored on the cell surface.

In a further aspect the invention provides a method of producing a ghost cell (GHC) by lysing the GHT according to the invention to form a cell that is substantially free of all intracellular components.

In yet another aspect the invention provides a method of producing a GHC by transfecting a cell expressing an MHC molecule with one or more plasmids containing a gene encoding a protein of interest and a GPI signaling anchor such that the protein of interest is expressed and GPI anchored to the cell surface; and lysing the cells of to form a cell that is substantially free of all intracellular components.

In another aspect the invention provides methods of producing a GHC by transfecting a cell with a plasmid encoding an MHC protein and a GPI signaling anchor; one or more plasmids comprising a gene encoding a protein of interest and a GPI signaling anchor such that the MHC molecule and the protein of interest are expressed and GPI anchored to the cell surface. The cell is then lysed as to form a cell that is substantially free of all intracellular components.

The GPI anchored protein of interest and/or the MHC molecules is within a lipid raft.

MHC molecules include for example HLA-Cw*3 and/or HLA-Cw*5.

The protein of interest is one or more co-stimulatory molecules or cytokines such as CD80, CD86, CD137, IL-15, CD28, IL-21, IL-2, IFN-gamma, IL-10, IL-12, TGF-beta, CD40L, IL-4, or CD64. In some aspects the co-stimulatory molecule is CD64 and the CD64 is loaded with an antibody such as an antibody that is specific for NK2GD or CD3.

Lysing is accomplished for example by pH, temperature, chemical, physical, hypotonic or hypertonic means.

Also provided is the GHT or the GHC or population thereof produced by the methods of the invention.

In yet another aspect the invention provides methods of expanding an oligoclonal immune cell population by co-culturing the GHC according to the invention with a population of immune cells. Also provided are methods of expanding an oligoclonal NK-cell population by co-culturing the GHC according to the invention wherein the GHC expresses CD64 loaded with an anti-NK2GD antibody with a NK-cell.

The immune cell is for example a T-cell, an NK-cell or a B-cell. Optimally, the ratio of GHC to immune cells is about 1:2 to 1:4. Optionally, IL-21, IL-15 IL-2, IL-4, IL-10, IL-12 or any combination thereof is added to the culture.

Also included in the invention is an expanded oligoclonal immune cell population produced by the method of the invention.

In other aspects the invention provides methods of treating cancer, infection or an autoimmue disease in a subject in need thereof by intravenously or intratumorally administering a first dose of the expanded immune cell population according to the invention. The cancer is a hematologic cancer such as leukemia or lymphoma or a solid cancer. The leukemia is Acute myeloid leukemia (AML), Chronic myeloid leukemia (CML), Acute lymphocytic leukemia (ALL), or Chronic lymphocytic leukemia (CLL). The lymphoma is B-cell lymphoma.

The solid cancer is for example, osteosarcoma, hemangiosarcoma, transitional cell carcinoma, melanoma, glioblastoma, neuroblastoma, mammary carcinoma, or a sarcoma or carcinoma of the gastrointestinal system.

Optionally, a second dose of the cell population is administered 7 days after the first dose.

In some aspects, a third dose of the cell population is administered 7 days after the second dose.

The subject has received a HSCT, high dose Cytoxan therapy, chemotherapy or radiation therapy prior to the administration of the cell population.

In some embodiments of the invention, the cancer is osteosarcoma and the cells are administered at a dose of $5 \times 10^8$ cells/m$^2$ 24-72 hours post targeted or whole body radiation.

In other embodiments of the hematologic cancer is lymphoma and the cells are administered at a dose of $5 \times 10^8$ cells/m$^2$.

In further embodiments, the hematologic cancer is acute myeloid leukemia and the cell population is administered every 7 to 10 days for a total of no more than 8 doses. Preferably the does is $2 \times 10^8$ cells/m$^2$ to $5 \times 10^8$ cells/m$^2$.

In other embodiments the cancer is hemangiosarcoma and the cells are administered at a dose of $5 \times 10^8$ cells/m$^2$.

In yet a further aspect of the invention provides methods of treating an immunological dysfunction in a subject in need thereof comprising administering at least one dose of the expanded immune cell population of the invention. Immunological dysfunctions include for example cancer, GVHD, chronic viral infection or an autoimmune disorder.

The subject is in an active cycle of the autoimmune disorder.

The cells are administered at a dose of $1 \times 10^7$ cells/m$^2$ to $5 \times 10^9$ cells/m$^2$.

The subject is a companion animal or a human. The companion animal is for example a canine, a feline or an equine. The expanded immune cells are autologous or allogeneic to the subject.

In further aspects, the invention provides a method of producing a tumor antigen specific T-cell population by co-culturing a population of T-cells that has been transfected with a plasmid containing a nucleic acid encoding activation-induced deaminase (AID) with the GHC according to the invention, and a tumor or a tumor cell line.

The plasmid further comprises a promoter, a signaling peptide, a start codon, a stop codon, a kozak sequence and/or a detectable label. The promoter is a cell specific or inducible promoter. The detectable label is for example a fluorescent protein. Preferably, the plasmid is produced by DNA printing or through a bacterial process.

The tumor and the T-cells are autologous or allogenic. The T-cells are primary cells or immortalized cells. The T-cells are human, canine, feline murine or equine.

Optionally, the T-cell population expresses a mutated T-cell receptor (TCR) or a mutated chimeric antigen receptor (CAR). Optionally, the method further includes sequencing the TCR or CAR. The invention also includes the mutated TCR or CAR sequences of identified by the method of the invention as well a T-cell, NK-cell or B-cell population engineered to express the mutated TCR or CAR sequences. Cells expressing the mutated TCR or CAR sequences can be expanded by co-culturing with a GHC according to the methods of the invention. These expanded cell population can be used to treat cancer, infection or an autoimmune disorder by administering to a subject the population of expanded cells.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and encompassed by the following detailed description and claims.

DETAILED DESCRIPTION OF THE INVENTION

Figure 1:
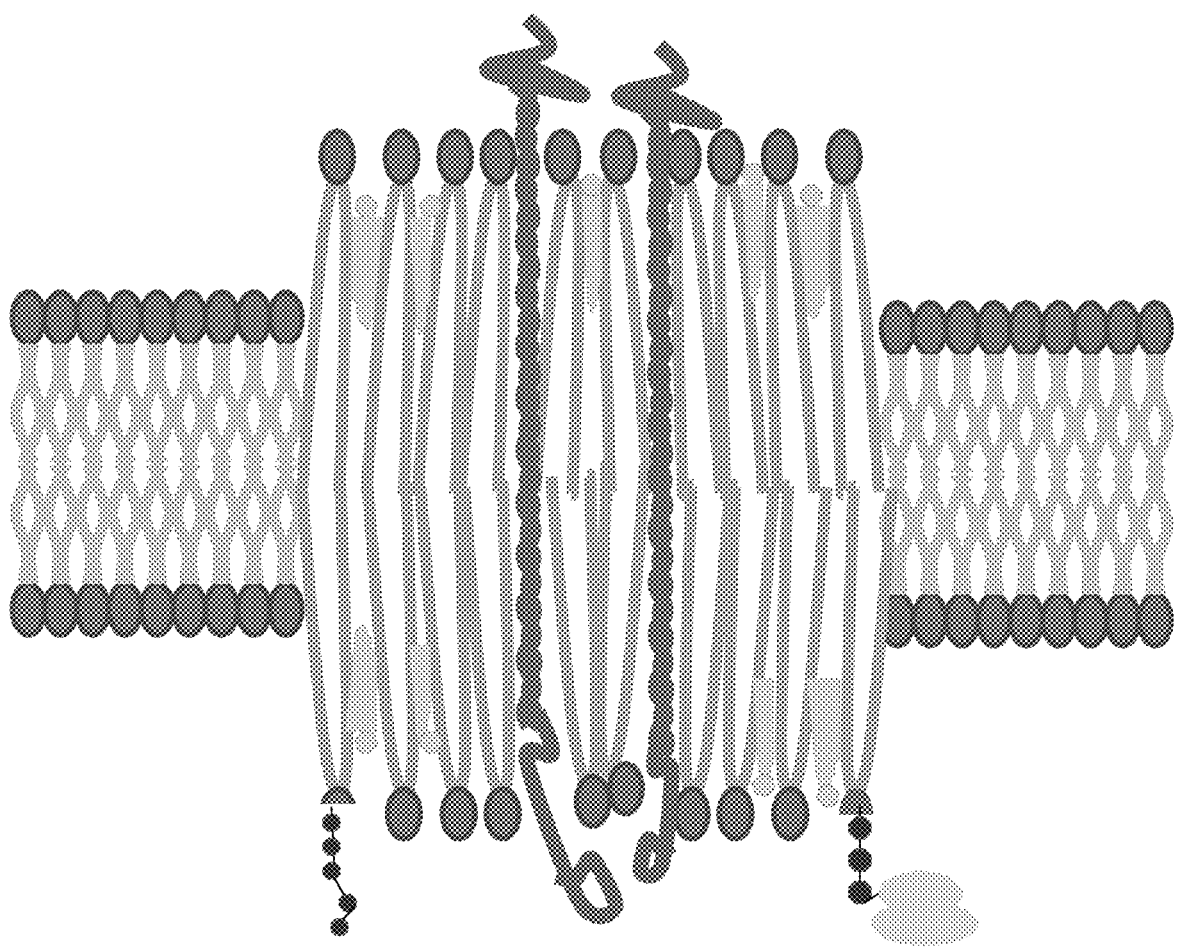
FIG. 1 shows lipid rafts of ghost cells.

The present invention relates to methods and compositions for inducing a systemic immune response against a tumor or pathogen. In particular, the present invention provides methods of immune cell activation (e.g. T-cells, B-cells, or NK-cells) for use in immunotherapy to treat cancers, infection and autoimmune disorders in humans, sport animals and companion animals. Activation of the immune cells by the methods of the invention results in cell expansion.

Biological therapies, such as NK or T-cell therapies, can target disease by employing mechanisms independent of chemo-radio-therapies. There is an unmet need to provide companion canines, other companion animals and humans, with lymphotherapies that can be used in combination with standard of care therapies or alone. The present invention provides targeted, T-cell receptor (TCR) oligoclonal T-cell, Natural Killer (NK) cell, and other immune cells lymphotherapy that can be utilized against malignancies, infection and autoimmune diseases. As a means to accelerate broader use of targeted lymphotherapy for mammalian, e.g. human use, the present invention provides following: (i) the "ghost cells" to numerically expand CAR-TCR-specific T cells, NK cells and B-cells for clinical use, (ii) the method of cellular (T and NK) HLA-Cw*3 and 5 expansion on ghost cells, (iii) TCR sequences and tumor targets generated from expansion method and patient response, (iv) dosing and conditioning treatment schedules lymphotherapy for treatment of disease, (v) biomarker and immunoscore useful in screening and diagnosing, and (vi) genetically modified cellular therapy using TCRs and chimeric antigen receptors (CAR).

The primary obstacles faced by cellular based immunotherapies are overcoming both peripheral and central tolerance issues as the tumor evolves through immunoediting pressures to become unrecognizable and avoidable immunologically and develops the ability to suppress an antitumor/pro-inflammatory response. The progression or development of malignancies, autoimmune diseases and infection (e.g, chronic viral infection can produce immunological dysfunction by alterations in cytokine production (both locally and systemically), inhibition of dendritic cell (DC) maturation thereby producing antigen presentation defects, T-cell dysfunctions characterized by ratio imbalances, signaling issues, gene modulation, immune synaptic malformations, and self-antigen presentation. Tumors can produce strong immunosuppressive cytokines, such as IL-10 and TGF-B.

The tumor micro-envirnoment (TME) is a complex milieu of tumor cells, endothelial cells, stromal cells, tumor associated macrophages (TAM), fibroblasts, myeloid derived suppressor cells (MDSC), NK cells, Tregs, CTLs, and monocytes. All of which are influenced directly or indirectly by the tumor. Chemo- and radio-therapies have also been shown to increase the expression of neo-antigens by residual tumor. Other pre-conditioning regimens alter $TH_1/TH_2$ profiles, reduce the numbers of MDSCs, Tregs, and TAMS, activate DC, cause tumor necrotic death for neo-antigen release, aymphotherapy will reverse the immunological dysfunction associated with malignancies and autoimmune diseases alike.

In order to accelerate broader use of targeted lymphotherapy, the present invention provides a method of producing "ghost cells" to numerically expand oligoclonal TCR-specific T cells, B-cells and NK cells. Lymphotherapy will reverse the immunological dysfunction associated with malignancies, infection and autoimmune diseases alike.

Ghost Cells

As used herein the term "ghost cells" is meant to include an immortalized cell line that has been rendered spherostomatocytic and contains little or no intracellular components, but retain plasma cell membrane and lipid raft integrity. The term "ghost cell" results from the preparation method to render the cell empty and non-viable.

Ghost cells according to the invention have on their plasma membrane a plurality of MHC molecules, e.g., MHC class I or MHC class II and a plurality of a protein of interest that is glycosylphosphatidylinositol (GPI) anchored in the plasma membrane. The use of GPI anchors is in direct contrast to the current methods that utilize transmembrane domains to anchor proteins in plasma membrane. Anchoring via a transmembrane domain results in variable expression throughout the plasma membrane. In contrast, the present inventor has discovered that GPI anchoring ensures that all transfected genes are expressed on the cell surface in close proximity inside lipid rafts. This conformation yields superior immune cell expansion. Preferably the ghost cells contain $10^5$ to $10^{10}$, more preferably $10^6$ to $9\times10^9$ lipid rafts containing the protein of interest.

Ghost cells are prepared by genetically modifying a cell to express a protein of interest. The protein of interest is anchored to lipid rafts via a glycosylphosphatidylinositol anchor (GPI) that is added to the protein during ER post-translational modification. Preferably the cell expresses endogenous MEW molecules. Alternatively the cell is genetically modified to express MEW molecules. For example the cell expresses or has been genetically modified to express HLA-Cw*3 and/or HLA-Cw*5. One skilled in the art will readily recognize the appropriate MHC molecule required to treat a particular disease or disorder.

The genetically modified cells, prior to treatment to become ghost cells are referred to herein as "ghost cell trainers".

The cell that is genetically modified to produce the ghost cell trainer is preferably a cell of human, canine, equine, murine or feline origin. The cell is a primary cell culture or an immortalized cell line. For example, the cell is an adherent or suspended mammalian cell line. Exemplary cells lines suitable for the production of ghost cells trainers include for example, immortalized cells lines such as K562, 722.21 or Jurkat.

Standard flow cytometry techniques are used to determine ghost cell trainer surface expression of lipid rafts, proteins, co-stimulatory, etc in each cell line before lysis. At least 70%, 75%, 80%, 85%, 90%, 95% or more of the ghost cell trainers in the population must express the protein of interest in lipid rafts. Ghost cell trainer expression of molecules, lipid rafts, etc must be greater than 90% to continue with cryopreservation and creation of ghost cells. To determine the expression in lipid rafts, as well as, surface placement and relative quantification, standard techniques of antibody patching and immunofluorescence microscopy is utilized. This allows the visualization and quantification of lipid raft components on the ghost cell trainer surface at various time points during cell culture. Ghost cell trainers are cultured using standard techniques known in the art for the particular cell being utilized. Suitable culture conditions for ghost cell trainers are for example 39° C., 5% $CO_2$, 95% humidified atmosphere; complete media (RPMI/DMEM media), 10-20% fetal calf serum, 5-15% glutamax. Culture media is changed 1 to 5 times per week to maintain cells at $10^6$ cells/mL; in either flasks, bags, or closed system bioreactors. Evaluation of ghost cell trainer phenotype aids in the optimization of ghost cell expansion, banking, cryopreservation, and thawing for use.

To prepare ghost cells, ghost cell trainers are treated with a specific hypotonic lytic procedure that extract all intracellular components, but allows plasma membrane, GPI anchored proteins, and lipid rafts to remain intact. Hypotonic lytic procedures for the preparation of ghost cells are known in the art. Briefly, the ghost cell trainers are exposed to a hypotonic lytic solution containing cocktails to inhibit protein degradation such as tyrosine, acid and alkaline phosphatases; serine proteases; trypsin, chymotrypsin, plasmin, and amino-peptidases; cysteine proteases; L-isozymes, and serine-threonine protein phosphatases diluted in distilled water with a pH of 7.0. This hypotonic lytic solution will cause the initiation of caspase 3,8 and mitochondrial apoptotic cascade, as well as, create a large hole in the weaker side of the cell membrane allowing the entire intracellular contents to leak out.

The protein of interest is an immunomodulatory molecule such as a co-stimulatory ligand, a co-stimulatory molecule, Fc receptor, or a cytokine.

Fc receptors include for example CD64 or CD32.

Other proteins of interest include importin or GD2.

"Co-stimulatory ligand" refers to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL (CD137), OX40L, inducible costimulatory ligand (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD-3C, CD27, CD28, 4-IBB, OX40, CD30, CD40, CD-40L, PD-1, ICOS, lymphocyte function-associated antigen-1 (LFA-1), CD2, CD7, LTGHT, NKG2C, B7-H3, a ligand that specifically binds with CD83.

A "co-stimulatory molecule" refers to the cognate binding partner on a T-cell that specifically binds with a co-stimulatory ligand, thereby mediating a co-stimulatory response by the cell, such as, but not limited to proliferation. Co-stimulatory molecules include, but are not limited to an MHC class 1 molecule, BTLA and Toll ligand receptor. Examples of costimulatory molecules include CD-3C, CD27, CD28, CD8, 4-1BB (CD137),-1BBL OX40, CD30, CD40, PD-1, ICOS, lymphocyte function-associated antigen-1 (LFA-1), CD2, CD7, LIGHT, NKG2C, B7-H3 and a ligand that specifically binds with CD83 and the like. In another particular embodiment, said signal transducing domain is a TNFR-associated Factor 2 (TRAF2) binding motifs, intracytoplasmic tail of costimulatory TNFR member family. Cytoplasmic tail of costimulatory TNFR family member contains TRAF2 binding motifs consisting of the major conserved motif (P/S/A)X(Q/E)E) or the minor motif (PXQXXD), wherein X is any amino acid. TRAF proteins are recruited to the intracellular tails of many TNFRs in response to receptor trimerization.

By cytokine is meant any substance that is secreted by certain cells of the immune system and have an effect on other cells. Exemplary cytokines include, but are not limited IL-1-like, IL-la, IL-10, IL-1RA, IL-18, Common g chain (CD132), IL-2, IL-4, IL-7, IL-9, IL-13, IL-15, Common b chain (CD131), IL-3, IL-5, GM-CSF, IL-6-like, IL-6, IL-11, G-CSF, IL-12, LIF, OSM, IL-10-like, IL-10, IL-20, IL-21, IL-14, IL-16, IL-17, IFN-α, IFN-γ, CD154, LT-β, TNF-αTNF-β, APRIL, CD70, CD153, CD178, GITRL, LIGHT, TALL-1, TRAIL, TWEAK, TRANCE, TGF-β1, TGF-β2, TGF-β3, Epo, Tpo, Flt-3L, SCF, M-CS, or any combinations thereof.

The protein of interest or MHC molecule may introduced by any methods know in the art. For example, expression vectors that encode the protein of interest or MHC molecule can be introduced as one or more DNA molecules or constructs. Optionally, there may be at least one marker that will allow for selection of cells that contain the construct(s).

The constructs can be prepared in conventional ways, where the genes and regulatory regions may be isolated, as appropriate, ligated, cloned in an appropriate cloning host, analyzed by restriction or sequencing, or other convenient means. Particularly, using PCR, individual fragments including all or portions of a functional unit may be isolated, where one or more mutations may be introduced using "primer repair", ligation, in vitro mutagenesis, etc., as appropriate. The construct(s) once completed and demonstrated to have the appropriate sequences may then be introduced into the cell by any convenient means. The constructs may be integrated and packaged into non-replicating, defective viral genomes like Adenovirus, Adeno-associated virus (AAV), or Herpes simplex virus (HSV) or others, including retroviral vectors or lentiviral vectors, for infection or transduction into cells. The constructs may include viral sequences for transfection, if desired. Alternatively, the construct may be introduced by fusion, electroporation, biolistics, transfection, lipofection, or the like. The cells may be grown and expanded in culture before introduction of the construct(s), followed by the appropriate treatment for introduction of the construct(s) and integration of the construct(s). The cells are then expanded and screened by virtue of a marker present in the construct. Various markers that may be used successfully include hprt, neomycin resistance, thymidine kinase, hygromycin resistance, etc.

In some instances, one may have a target site for homologous recombination, where it is desired that a construct be integrated at a particular locus. For example, one can knock out an endogenous gene and replace it (at the same locus or elsewhere) with the gene encoded for by the construct using materials and methods known in the art for homologous recombination. For homologous recombination, one may use either .OMEGA. or O-vectors. See, for example, Thomas and Capecchi, Cell (1987) 51, 503-512; Mansour, et al., Nature (1988) 336, 348-352; and Joyner, et al., Nature (1989) 338, 153-156.

Vectors containing useful elements such as bacterial or yeast origins of replication, selectable and/or amplifiable markers, promoter/enhancer elements for expression in prokaryotes or eukaryotes, etc. that may be used to prepare stocks of construct DNAs and for carrying out transfections are well known in the art, and many are commercially available.

In addition, other methods known in the art may be used, such as self-inactivating transposase and transposon system, a drug selection equipped DNA printed plasmid, or CRISPR.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1988 and Ausubel et al., 1994, both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes.

Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30 110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

The identity of tissue-specific promoters or elements, as well as assays to characterize their activity, is well known to those of skill in the art.

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals.

In certain embodiments of the invention, the use of internal ribosome entry sites (IRES) elements are used to create multigene, or polycistronic, messages, and these may be used in the invention.

In certain embodiments of the invention, the 2A self cleaving peptides are used to create multigene, or polycistronic, messages, and these may be used in the invention.

Vectors can include a multiple cloning site (MCS), which is a nucleic acid region that contains multiple restriction enzyme sites, any of which can be used in conjunction with standard recombinant technology to digest the vector. "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

Splicing sites, termination signals, origins of replication, and selectable markers may also be employed.

In certain embodiments, a plasmid vector is contemplated for use to transform a host cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, E. coli is often transformed using derivatives of pBR322, a plasmid derived from an E. coli species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEM™ 11 may be utilized in making a recombinant phage vector which can be used to transform host cells, such as, for example, E. coli LE392.

Further useful plasmid vectors include pIN vectors (Inouye et al., 1985); and pGEX vectors, for use in generating glutathione S transferase (GST) soluble fusion proteins for later purification and separation or cleavage. Other suitable fusion proteins are those with galactosidase, ubiquitin, and the like.

Bacterial host cells, for example, E. coli, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 h, the cells are collected by centrifugation and washed to remove residual media.

The ability of certain viruses to infect cells or enter cells via receptor mediated endocytosis, and to integrate into host cell genome and express viral genes stably and efficiently have made them attractive candidates for the transfer of foreign nucleic acids into cells (e.g., mammalian cells). Components of the present invention may be a viral vector that encodes one or peptides of interest. Non-limiting examples of virus vectors that may be used to deliver a nucleic acid of the present invention are described below.

A particular method for delivery of the nucleic acid involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell specific construct that has been cloned therein. Knowledge of the genetic organization or adenovirus, a 36 kb, linear, double stranded DNA virus, allows substitution of large pieces of adenoviral DNA with foreign sequences up to 7 kb (Grunhaus and Horwitz, 1992).

The nucleic acid may be introduced into the cell using adenovirus assisted transfection. Increased transfection efficiencies have been reported in cell systems using adenovirus coupled systems (Kelleher and Vos, 1994; Cotten et al., 1992; Curiel, 1994). Adeno associated virus (AAV) is an attractive vector system for use in the cells of the present invention as it has a high frequency of integration and it can infect nondividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. Nos. 5,139,941 and 4,797,368, each incorporated herein by reference.

Retroviruses are useful as delivery vectors because of their ability to integrate their genes into the host genome, transferring a large amount of foreign genetic material, infecting a broad spectrum of species and cell types and of being packaged in special cell lines (Miller, 1992).

In order to construct a retroviral vector, a nucleic acid (e.g., one encoding the desired sequence) is inserted into the viral genome in the place of certain viral sequences to produce a virus that is replication defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and t at is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

Other viral vectors may be employed as vaccine constructs in the present invention. Vectors derived from viruses such as vaccinia virus (Ridgeway, 1988; Baichwal and Sugden, 1986; Coupar et al., 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et al., 1988; Horwich et al., 1990).

A nucleic acid to be delivered may be housed within an infective virus that has been engineered to express a specific binding ligand. The virus particle will thus bind specifically to the cognate receptors of the target cell and deliver the contents to the cell. A novel approach designed to allow specific targeting of retrovirus vectors was developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

Suitable methods for nucleic acid delivery for transfection or transformation of cells are known to one of ordinary skill in the art. Such methods include, but are not limited to, direct delivery of DNA, RNA or mRNA such as by ex vivo transfection, by injection, and so forth. Through the application of techniques known in the art, cells may be stably or transiently transformed.

Methods of Immune Cell Expansion

Immune cells are activated in ex vivo by first isolating immune cells from a subject sample. The sample is for example blood, bone marrow, or a tissue sample. For example, immune cells are isolated from peripheral blood mononuclear cells (PBMCs), bone marrow, or the spleen. Immune cells include B-cells, T cells, including a helper T cell (Th), a cytotoxic T cell (also known as TC, Cytotoxic T Lymphocyte, CTL, T-Killer cell, cytolytic T cell, CD8+ T-cells or killer T cell) a regulatory T cell (Treg), a T follicular regulatory cell (TFR), NK cells and NKT cells.

Immune cells are isolated by any methods known in the art. For example, immune cells are isolated by ficoll density centrifugation, flow cytometry, magnetic cell isolation and cell separation (MACS), RosetteSep, or antibody panning. One or more isolation techniques may be utilized in order to provide an immune cell population with sufficient purity, viability, and yield.

The purity of the isolated immune cells is at least about 70%, 80%, 85%, 90%, 91%, 92%, 93%, 94%, 95%, or more. The isolated immune cells are at least about 70%, 75%, 80%, 85%, 90%, 95%, or more viable.

Optionally, after isolation the immune cells can be cryopreserved in in-house freeze media (FM) or commercially derived FM. FM may contain the following solutions: 40-70% Saline (PBS, HBSS, etc), 20-40% canine, feline, human, or equine serum, 1-10% Dimethyl sulfoxide (DMSO) and may be filtered sterilized one to three times. The concentration range of cells in the FM is between $5 \times 10^6$ to $1 \times 10^8$ cells/ml.

Immune cells are activated resulting in expansion by co-cultured with ghost cells. Co-culturing also results in the immune cells having one or more additional characteristics such as increased pro-inflammatory cytokine production, increased CD3zeta expression, increased ZAP70 expression, upregulation of CD3, CD8; increased cell diameter and elongated morphology; increased homing and trafficking molecules like CCR7, increased expression of perforin and cytolytic enzymes like granzyme B.

Ghost cells will be added to the immune cell culture at a ratio ranging from (Ghost Cell:immune cell) 2:1 to 1:3.

This is a novel way of inducing activation. In contrast to the method of the invention, current methods of immune cell activation which utilize cesium irradiation to kill the tumor cell lines are more expensive and have complex regulatory issues, making it difficult for therapeutic applications. In addition, cesium irradiation the tumor cell lines continue to function as highly viable artificial antigen presenting cells in culture for days after irradiation. These artificial antigen presenting cells remain intact and have the capacity to proliferate, move, and secrete immunosuppressive cytokines. In contrast, the activation though ghost cells according to the methods of the invention is superior to previous methods as using ghost cells instead of irradiated tumor cells line, alleviates the immunosuppressive effect of cytokine secretion; tumor cell line clustering to inhibit T-cell mediated lysis; T-cell tolerance to tumor antigens, and possible tumor proliferation and viability. In addition the methods of the invention wimprove synaptic formation and strength to increase immune cell expansion.

In some embodiments, the immune cells are activated in in RPMI, 1-100% 100× glutamax, 1-100% FBS) at a concentration of 1.5 to $2 \times 10^6$ cells/ml.

In some embodiments, the cells are co-cultured in a cell culture medium containing a cytokine. The cytokine is, for example, IL-1-like, IL-1α, IL-1β, IL-1RA, IL-18, Common g chain (CD132), IL-2, IL-4, IL-7, IL-9, IL-13, IL-15, Common b chain (CD131), IL-3, IL-5, GM-CSF, IL-6-like, IL-6, IL-11, G-CSF, IL-12, LIF, OSM, IL-10-like, IL-10, IL-20, IL-21, IL-14, IL-16, IL-17, IFN-α, IFN-β, IFN-γ, CD154, LT-β, TNF-αTNF-β, 4-1BBL, APRIL, CD70, CD153, CD178, GITRL, LIGHT, OX40L, TALL-1, TRAIL, TWEAK, TRANCE, TGF-β1, TGF-β2, TGF-β3, Epo, Tpo, Flt-3L, SCF, M-CSF, αCD40, or any combinations thereof. Toll-like receptor agonist may also be used. Preferably the cytokine is IL-2, and/or IL-21.

The cytokine is added to the cultures 2 to 3 times per week at a concentration of and, respectively, 10 to 100 U/mL or IL-2) and/or 25 to 75 ug/mL of IL-21. In some embodiments IL-2 is not added for the first 7 to 10 days of culture.

Immune cells will be re-stimulated with ghost cells every 4 to 8 days until a clinically sufficient number of cells has been reached for each subject. The clinically significant numbers is based on body surface area (BSA) calculated from the weight of the subject.

Immune cells will be re-stimulated with ghost cells every 4 to 8 days until a clinically sufficient number of cells has been reached for each subject. The clinically significant numbers is based on body surface area (BSA) calculated from the weight of the subject.

The expanded oligoclonal immune cells may be cryopreserved in in-house freeze media (FM) or commercially derived FM prior to infusion into a subject. FM may contain the following solutions: 40-70% Saline (PBS, HBSS, etc), 20-40% canine, feline, human, or equine serum, 1-10% Dimethyl sulfoxide (DMSO) and may be filtered sterilized one to three times. The concentration range of cells in the FM is between $5 \times 10^6$ to $1 \times 10^8$ cells/ml.

Therapeutic Methods

The reagents according to the invention can be used for treating cancer, infection or other immunological disorders such as graft vs host disease or autoimmune disorders in a subject in need thereof. In another embodiment, reagents according to the invention can be used in the manufacture of a medicament for treatment of a cancer, infection or other immunological disorders such as graft vs host disease or autoimmune disorders in a subject in need thereof. The present invention relies on methods for treating subjects in need thereof by administering to the subject a composition containing the oligoclonal immune cells expanded by the methods of the invention The subject is a mammal. Mammals include, but are not limited to, humans, farm animals, sport animals (e.g., horses), and companion animals (e.g., dog or cats).

Treatment can be ameliorating, curative or prophylactic. It may be either part of an autologous immunotherapy or part of an allogenic immunotherapy treatment. By autologous, it is meant that cells, cell line or population of cells used for treating patients are originating from said subject or from a Leucocyte Antigen (LA) compatible donor. By allogeneic is meant that the cells or population of cells used for treating subjects are not originating from the subject but from a matching (i.e., hostocompatiable) donor.

Treatment is efficacious if the treatment leads to clinical benefit such as, a decrease in size, prevalence, or metastatic potential of the tumor in the subject. When treatment is applied prophylactically, "efficacious" means that the treatment retards or prevents tumors from forming or prevents or alleviates a symptom of clinical symptom of the tumor. Efficaciousness is determined in association with any known method for diagnosing or treating the particular tumor type.

Cells and methods of producing them that can be used with the disclosed methods are described herein. Treatment can be used to treat patients diagnosed with cancer, autoimmune disorders or Graft versus Host Disease (GvHD). Cancers that may be treated include tumors that are not vascularized, or not yet substantially vascularized, as well as vascularized tumors. The cancers may comprise nonsolid tumors such as hematological tumors, for example, leukemias and lymphomas. The leukemia is acute myeloid leukemia (AML), chronic myeloid leukemia (CML), acute lymphocytic leukemia (ALL) or chronic lymphocytic leukemic (CLL). Alternatively, the tumor is a solid tumor. Solid tumors include, but are not limited to, carcinoma; such as transitional cell carcinoma, mammary carcinoma, or carcinoma of the gastrointestinal system; sarcoma such as osteosarcoma, hemangiosarcoma or sarcoma of the gastrointestinal system; blastoma such as neuroblastoma or glioblastoma; or melanoma.

Treatment may be in combination with one or more therapies against cancer selected from the group of antibodies therapy, chemotherapy, cytokines therapy, dendritic cell therapy, stem cell therapy, gene therapy, hormone therapy, laser light therapy and radiation therapy prior to or after treatment according to the methods of the invention.

For example the subject has received HSCT, targeted or whole body irradiation or high dose Cytoxan therapy, prior to the administration of the cell population. For example, cells are administered 7-14 days post high dose Cytoxan therapy. For example, cells are administered 24-72 hours post targeted or whole body radiation.

Therapeutic Administration

The invention includes administering to a subject therapeutic composition comprising the expanded oligoclonal immune cells produced by the methods of the invention.

Effective doses vary, as recognized by those skilled in the art, depending on route of administration, excipient usage, and coadministration with other therapeutic treatments including use of other anti-proliferative agents or therapeutic agents for treating, preventing or alleviating a symptom of cancer, infection or other immunological disorders such as graft vs host disease or autoimmune disorders. A therapeutic regimen is carried out by identifying a mammal, e.g., a suffering from a cancer, infection or other immunological disorders such as graft vs host disease or autoimmune disorders using standard methods.

Compositions containing the appropriate expanded oligoclonal immune cells are administered to an individual in a regimen determined as appropriate by a person skilled in the art. For example, the composition may be given multiple times at an appropriate interval and dosage.

The cells may be administered as desired. Depending upon the response desired, the manner of administration, the life of the cells, the number of cells present, various protocols may be employed. Depending upon the nature of the cells, the cells may be introduced into a host organism, e.g. a mammal, in a wide variety of ways. The cells may be introduced at the site of the tumor, in specific embodiments, although in alternative embodiments the cells hone to the cancer or are modified to hone to the cancer. The number of cells that are employed will depend upon a number of circumstances, the purpose for the introduction, the lifetime of the cells, the protocol to be used, for example, the number of administrations, the ability of the cells to multiply, the stability of the recombinant construct, and the like. The cells may be applied as a dispersion, generally being injected at or near the site of interest. The cells may be in a physiologically-acceptable medium.

In some embodiments, the cells are encapsulated to inhibit immune recognition and placed at the site of the tumor.

The administration of the cells or population of cells according to the present invention may be carried out in any convenient manner, including injection, transfusion, implantation or transplantation. The compositions described herein may be administered to a patient subcutaneously, intradermaly, intratumorally, intranodally, intramedullary, intramuscularly, by intravenous or intralymphatic injection, or intraperitoneally. In one embodiment, the cell compositions of the present invention are preferably administered by intravenous injection. Additionally, compositions are administered by implanting (either directly into an organ or subcutaneously) a solid or resorbable matrix which slowly releases the composition into adjacent and surrounding tissues of the subject.

The administration of the cells or population of cells can consist of the administration of $10^4$-$10^9$ cells per kg body weight, preferably $10^5$ to $10^6$ cells/kg body weight including all integer values of cell numbers within those ranges. An appropriate does is for example 25-300 ml, 25-200 ml, 25-100 ml of a composition containing approximately $10^5$-$10^{10}$ cell/m$^2$, preferably about $1\times10^7$ to $5\times10^9$ cell/m$^2$, preferably the dose is $5\times10^8$ cell/m$^2$.

The cells or population of cells can be administrated in one or more doses. In another embodiment, said effective amount of cells are administrated as a single dose. In another embodiment, said effective amount of cells are administrated as more than one dose over a period time. Doses may be administered once, or more than once. In some embodiments, it is preferred that the therapeutic composition is administered once every 7 to 10 days, The predetermined duration of time may be 1 week, 2 weeks, 3 weeks, 4 weeks, 5 weeks, 6 weeks, 7 weeks, 2 months, 3 months, 4 months, 5 months, 6 months, 7 months, 8 months, 9 months, 10 months, 11 months, or up to 1 year.

Timing of administration is within the judgment of managing physician or veterinarian and depends on the clinical condition of the subject. While individual needs vary, determination of optimal ranges of effective amounts of a given cell type for a particular disease or conditions within the skill of the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

The composition of expanded oligoclonal immune cells prior to administration to the subject must have sufficient viability. The viability of the fused cells at the time of administration is at least 50%, at least 60%, at least 70%, at least 80% or greater.

Prior to administration, the population of expanded oligoclonal immune cells are free of components used during the production, e.g., cell culture components and substantially free of mycoplasm, endotoxin, and microbial contamination. Preferably, the population of fused cells has less than 10, 5, 3, 2, or 1 CFU/swab. Most preferably the population of expanded oligoclonal immune cells has 0 CFU/swab. For example, the results of the sterility testing is "negative" or "no growth". The endotoxin level in the population of tumor cells is less than 20 EU/mL, less than 10 EU/mL or less than 5 EU/mL. The result of the myoplasm testing is "negative".

For non-food animal use all final cell products must conform to the requirements imposed by the USDA under 9CFR Part103.3.

For human use, all final cell product must conform with rigid requirements imposed by the Federal Drug Administration (FDA). The FDA requires that all final cell products must minimize "extraneous" proteins known to be capable of producing allergenic effects in human subjects as well as minimize contamination risks. Moreover, the FDA expects a minimum cell viability of 70%, and any process should consistently exceed this minimum requirement.

In some embodiments, it is preferred that the therapeutic compounds described herein are administered in combination with another therapeutic agent, such as a chemotherapeutic agent, radiation therapy, or an anti-mitotic agent. In some aspects, the anti-mitotic agent is administered prior to administration of the present therapeutic compound, in order to induce additional chromosomal instability to increase the efficacy of the present invention to targeting cancer cells. Examples of anti-mitotic agents include taxanes (i.e., paclitaxel, docetaxel), and vinca alkaloids (i.e., vinblastine, vincristine, vindesine, vinorelbine).

Identification of T-Cell Receptor Sequences

In another object of the invention T-cell receptor (TCR) sequence of the expanded T-cells of the invention are identified. Alternatively, the native TCR sequences are mutated and the TCR tumor antigen pairings are identified. Methods of mutating TCR sequences are known in the art and include SHM or AID.

Native TCR sequences or mutated TCR sequence are used to create a chimeric antigen receptor cell. (CAR), that are then used to treat diseases and disorders as described in the method above.

The CAR according to the invention generally comprises at least one transmembrane polypeptide comprising at least one extracellular ligand-binding domain and; one transmembrane polypeptide comprising at least one intracellular signaling domain; such that the polypeptides assemble together to form a Chimeric Antigen Receptor.

The term "extracellular ligand-binding domain" as used herein is defined as an polypeptide that is capable of binding a ligand. Preferably, the domain will be capable of interacting with a cell surface molecule. For example, the extracellular ligand-binding domain may be chosen to recognize a ligand that acts as a cell surface marker on target cells associated with a particular disease state. Most preferably, the extracellular domain is the variable region of a T-cell receptor.

In particular, the extracellular ligand-binding domain comprises the variable region of a T-cell receptor specific for a tumor associated antigen or a self antigen. Preferably, the T-cell receptor, the tumor associated antigen or self antigen has been identified from a T-cell obtained from a subject. For example, the T-cell receptor is identified from a tumor infiltrating lymphocyte, a lymphocyte from an autoimmune site or a lymphocyte from a graft tissue.

In a preferred embodiment said transmembrane domain further comprises a stalk region between said extracellular ligand-binding domain and said transmembrane domain. The term "stalk region" used herein generally means any oligo- or polypeptide that functions to link the transmembrane domain to the extracellular ligand-binding domain. In particular, stalk regions are used to provide more flexibility and accessibility for the extracellular ligand-binding domain. A stalk region may comprise up to 300 amino acids, preferably 10 to 100 amino acids more preferably 25 to 50 amino acids and most preferably 3 to 15 amino acids. Stalk region may be derived from all or part of naturally occurring molecules, such as from all or part of the extracellular region of CD8, CD4 or CD28, or from all or part of an antibody constant region. Alternatively the stalk region may be a synthetic sequence that corresponds to a naturally occurring stalk sequence, or may be an entirely synthetic stalk sequence. In a preferred embodiment said stalk region is a part of human CD8 alpha chain.

The signal transducing domain or intracellular signaling domain of the CAR of the invention is responsible for intracellular signaling following the binding of extracellular ligand binding domain to the target resulting in the activation of the immune cell and immune response. In other words, the signal transducing domain is responsible for the activation of at least one of the normal effector functions of the immune cell in which the CAR is expressed. For example, the effector function of a T cell can be a cytolytic activity or helper activity including the secretion of cytokines. Thus, the term "signal transducing domain" refers to the portion of a protein which transduces the effector signal function signal and directs the cell to perform a specialized function.

Signal transduction domain comprises two distinct classes of cytoplasmic signaling sequence, those that initiate antigen-dependent primary activation, and those that act in an antigen-independent manner to provide a secondary or co-stimulatory signal. Primary cytoplasmic signaling sequence can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Examples of ITAM used in the invention can include as non limiting examples those derived from TCR zeta, FcR gamma, FcR beta, FcR epsilon, CD3 gamma, CD3 delta, CD3 epsilon, CD5, CD22, CD79a, CD79b and CD66d. In a preferred embodiment, the signaling transducing domain of the CAR can comprise the CD3 zeta signaling domain, or the intracytoplasmic domain of the Fc epsilon RI beta or gamma chains. In another preferred embodiment, the signaling is provided by CD3 zeta together with co-stimulation provided by CD28 and a tumor necrosis factor receptor (TNFr), such as 4-1BB or OX40), for example.

In particular embodiment the intracellular signaling domain of the CAR of the present invention comprises a co-stimulatory signal molecule. In some embodiments the intracellular signaling domain contains 2, 3, 4 or more co-stimulatory molecules in tandem. A co-stimulatory molecule is a cell surface molecule other than an antigen receptor or their ligands that is required for an efficient immune response.

The distinguishing features of appropriate transmembrane polypeptides comprise the ability to be expressed at the surface of an immune cell, in particular lymphocyte cells or Natural killer (NK) cells, and to interact together for directing cellular response of immune cell against a predefined target cell. The different transmembrane polypeptides of the CAR of the present invention comprising an extracellular ligand-biding domain and/or a signal transducing domain interact together to take part in signal transduction following the binding with a target ligand and induce an immune response. The transmembrane domain can be derived either from a natural or from a synthetic source. The transmembrane domain can be derived from any membrane-bound or transmembrane protein.

The term "a part of" used herein refers to any subset of the molecule, that is a shorter peptide. Alternatively, amino acid sequence functional variants of the polypeptide can be prepared by mutations in the DNA which encodes the polypeptide. Such variants or functional variants include, for example, deletions from, or insertions or substitutions of, residues within the amino acid sequence. Any combination of deletion, insertion, and substitution may also be made to arrive at the final construct, provided that the final construct possesses the desired activity, especially to exhibit a specific anti-target cellular immune activity. The functionality of the CAR of the invention within a host cell is detectable in an assay suitable for demonstrating the signaling potential of said CAR upon binding of a particular target. Such assays are available to the skilled person in the art. For example, this assay allows the detection of a signaling pathway, triggered upon binding of the target, such as an assay involving measurement of the increase of calcium ion release, intracellular tyrosine phosphorylation, inositol phosphate turnover, or interleukin (IL) 2, interferon gamma., GM-CSF, IL-3, IL-4 production thus effected.

Embodiments of the invention include cells that express a CAR (i.e, CARTS). The cell may be of any kind, including an immune cell capable of expressing the CAR for cancer therapy or a cell, such as a bacterial cell, that harbors an expression vector that encodes the CAR. As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a eukaryotic cell that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a vector, has been introduced. Therefore, recombinant cells are distinguishable from naturally occurring cells which do not contain a recombinantly introduced nucleic acid. In embodiments of the invention, a host cell is a T cell, including a helper T cell (Th), a cytotoxic T cell (also known as TC, Cytotoxic T Lymphocyte, CTL, T-Killer cell, cytolytic T cell, CD8+ T-cells or killer T cell) a regulatory T cell (Treg), a T follicular regulatory cell (TFR), NK cells and NKT cells are also encompassed in the invention.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

The cells can be autologous cells, syngeneic cells, allogenic cells and even in some cases, xenogeneic cells.

The invention further includes CARTS that are modified to secrete one or more polypeptides. The polypeptide can be for example an antibody or cytokine.

Armed CARTS have the advantage of simultaneously secreting a polypeptide at the targeted site, e.g. tumor site, graft site or autoimmune site.

Expression vectors that encode the CARs can be introduced as one or more DNA molecules or constructs, where there may be at least one marker that will allow for selection of host cells that contain the construct(s).

The constructs can be prepared in conventional ways, where the genes and regulatory regions may be isolated, as appropriate, ligated, cloned in an appropriate cloning host, analyzed by restriction or sequencing, or other convenient means.

Identification of Immune Cell Epitopes

Another object of the invention is the identification of immune cell, e.g. T-cell epitopes of an antigen, which method allows for simultaneous and rapid examination of a large number of peptide sequences, for their capability of binding to specific MHC molecules.

Specifically, the invention provides method of identifying and/or detecting tumor specific neoantigens that are useful in inducing a tumor specific immune response in a subject.

The molecules which transport and present peptides on the cell surface are referred to as proteins of the major histocompatibility complex (MHC). The MHC proteins present mainly peptides, which are processed from external antigen sources, i.e. outside of the cells, to T-helper (Th) cells. The peptides attach themselves to the molecules of MHC class I by competitive affinity binding within the endoplasmic reticulum, before they are presented on the cell surface. The affinity of an individual peptide is directly linked to its amino acid sequence and the presence of specific binding motifs in defined positions within the amino acid sequence. If the sequence of such a peptide is known, it is possible, for example, to manipulate the immune system against diseased cells using, for example, peptide vaccines. Using computer algorithms, it is possible to predict potential affinity.

The present invention is based, on the identification of certain mutations (e.g., the variants or alleles that are present in cancer or diseased cells). In particular, these mutations are present in the genome of cancer or diseased cells of a subject having cancer or another immunodysfunction but not in normal tissue from the subject.

In particular, the invention provides a method of vaccinating or treating a subject by identifying a plurality of disease specific mutations in the genome of a subject. Mutant peptides and polypetideds having the identified mutations and that binds to a class I HLA protein are selected. Optionally, these peptide and polypetides binds to a class I HLA proteins with a greater affinity than the wild-type peptide and/or are capable of activating anti-tumor CD8 T-cells. These peptides are administered to the subject as a vaccine. Alternatively, the peptides are used to pulse immune cells or CAR cells which are then administered to the subject.

The invention further includes isolated peptides that comprise the disease specific mutations identified by the methods of the invention. These peptides and polypeptides are referred to herein as "neoantigenic peptides" or "neoantigenic polypeptides". The term "peptide" is used interchangeably with "mutant peptide" and "neoantigenic peptide" in the present specification to designate a series of residues, typically L-amino acids, connected one to the other, typically by peptide bonds between the α-amino and carboxyl groups of adjacent amino acids. Similarly, the term "polypeptide" is used interchangeably with "mutant polypeptide" and "neoantigenic polypeptide" in the present specification to designate a series of residues, typically L-amino acids, connected one to the other, typically by peptide bonds between the α-amino and carboxyl groups of adjacent amino acids. The polypeptides or peptides can be a variety of lengths, either in their neutral (uncharged) forms or in forms which are salts, and either free of modifications such as glycosylation, side chain oxidation, or phosphorylation or containing these modifications, subject to the condition that the modification not destroy the biological activity of the polypeptides as herein described.

In certain embodiments the size of the at least one neoantigenic peptide molecule may comprise, but is not limited to, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 60, about 70, about 80, about 90, about 100, about 110, about 120 or greater amino molecule residues, and any range derivable therein. In specific embodiments the neoantigenic peptide molecules are equal to or less than 50 amino acids.

In some embodiments the particular neoantigenic peptides and polypeptides of the invention are: for MEW Class I 13 residues or less in length and usually consist of between about 8 and about 11 residues, particularly 9 or 10 residues; for MHC Class II, 15-24 residues.

The neoantigenic peptides and polypeptides bind an HLA protein. In some aspect the neoantigenic peptides and polypeptides binds an HLA protein with greater affinity than a wild-type peptide. The neoantigenic peptide or polypeptide has an IC50 of at least less than 5000 nM, at least less than 500 nM, at least less than 250 nM, at least less than 200 nM, at least less than 150 nM, at least less than 100 nM, at least less than 50 nM or less.

The neoantigenic peptides and polypeptides do not induce an autoimmune response and/or invoke immunological tolerance when administered to a subject.

The present invention is directed to an immunogenic composition, e.g., a vaccine composition capable of raising a specific T-cell response. The vaccine composition comprises mutant peptides and mutant polypeptides corresponding to disease specific neoantigens identified by the methods described herein.

A person skilled in the art will be able to select preferred peptides, polypeptide or combination of therof by testing, for example, the generation of T-cells in vitro as well as their efficiency and overall presence, the proliferation, affinity and expansion of certain T-cells for certain peptides, and the functionality of the T-cells, e.g. by analyzing the IFN-γ production or tumor killing by T-cells. Usually, the most efficient peptides are then combined as a vaccine.

Definitions

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

As used herein, the T lymphocyte can be any T lymphocyte, such as a cultured T lymphocyte, e.g., a primary T lymphocyte, or a T lymphocyte from a cultured T cell line, e.g., Jurkat, SupT1, etc., or a T lymphocyte obtained from a mammal. If obtained from a mammal, the T lymphocyte can be obtained from numerous sources, including but not limited to blood, bone marrow, lymph node, the thymus, or other tissues or fluids. T lymphocytes can also be enriched for or purified. Preferably, the T lymphocyte is a human T lymphocyte. More preferably, the T lymphocyte is a T lymphocyte isolated from a human. The T lymphocyte can be any type of T lymphocyte and can be of any developmental stage, including but not limited to, CD4$^+$/CD8.$^+$ double positive T lymphocytes, CD4$^+$ helper T lymphocytes, e.g., Th$_1$ and Th$_2$ cells, CD8$^+$ T lymphocytes (e.g., cytotoxic T lymphocytes), peripheral blood mononuclear cells (PBMCs), peripheral blood leukocytes (PBLs), tumor infiltrating lymphocytes (TILs), memory T cells, naive T lymphocytes, and the like. Preferably, the T lymphocyte is a TIL or a PBMC.

As used herein, "NK cells" means cytotoxic effector cells with the capacity to lyse tissue culture cells without participation of an antibody and without in vitro or in vivo sensitization. NK cells may also be characterized by the presence of cell surface receptors or proteins that distinguish NK cells from other lymphoid cells, and cells of the erythroid or myeloid lineages, for example, see, Bradshaw et al., Handbook of Cell Signaling (2003).

As used herein, "cells capable of differentiation into NK cells" refers to HSCs that differentiate into NK cells, when Jagged2, Flt3L, IL-7, and SCF are expressed in co-cultured cells or added to the growth media. Optionally, IL-2 may be supplied. Cells capable of differentiation into NK cells may be genetically modified either in vivo or in vitro, for example, reporter constructs may be introduced, or therapeutic gene products may by introduced or alternatively regulated.

The term "immune cells" refers to cells that specifically recognize an antigen present, for example on a neoplastic or tumor cell. For the purposes of this invention, immune effector cells include, but are not limited to, B cells; monocytes; macrophages; NK cells; and T cells such as cytotoxic T lymphocytes (CTLs), for example CTL lines, CTL clones, and CTLs from tumor, inflammatory sites or other infiltrates.

"T-lymphocytes" denotes lymphocytes that are phenotypically CD3+, typically detected using an anti-CD3 monoclonal antibody in combination with a suitable labeling technique. The T-lymphocytes of this invention are also generally positive for CD4, CD8, or both. The term "naïve" immune effector cells refers to immune effector cells that have not encountered antigen and is intended to by synonymous with unprimed and virgin. "Educated" refers to immune effector cells that have interacted with an antigen such that they differentiate into an antigen-specific cell.

The terms "antigen presenting cells" or "APCs" includes both intact, whole cells as well as other molecules which are capable of inducing the presentation of one or more antigens, preferably with class I MHC molecules. Examples of suitable APCs are discussed in detail below and include, but are not limited to, whole cells such as macrophages, dendritic cells, B cells; purified MHC class I molecules complexed to β2-microglobulin; and foster antigen presenting cells.

"Treatment" is an intervention performed with the intention of preventing the development or altering the pathology or symptoms of a disorder. Accordingly, "treatment" refers to both therapeutic treatment and prophylactic or preventative measures. Those in need of treatment include those already with the disorder as well as those in which the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy. As used herein, "ameliorated" or "treatment" refers to a symptom which is approaches a normalized value (for example a value obtained in a healthy patient or individual), e.g., is less than 50% different from a normalized value, preferably is less than about 25% different from a normalized value, more preferably, is less than 10% different from a normalized value, and still more preferably, is not significantly different from a normalized value as determined using routine statistical tests.

Thus, treating may include suppressing, inhibiting, preventing, treating, or a combination thereof. Treating refers inter alia to increasing time to sustained progression, expediting remission, inducing remission, augmenting remission, speeding recovery, increasing efficacy of or decreasing resistance to alternative therapeutics, or a combination thereof "Suppressing" or "inhibiting", refers inter alia to delaying the onset of symptoms, preventing relapse to a disease, decreasing the number or frequency of relapse episodes, increasing latency between symptomatic episodes, reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof. The symptoms are primary, while in another embodiment, symptoms are secondary. "Primary" refers to a symptom that is a direct result of the proliferative disorder, while, secondary refers to a symptom that is derived from or consequent to a primary cause. Symptoms may be any manifestation of a disease or pathological condition.

The "treatment of cancer or tumor cells", refers one or more of the following effects: (1) inhibition of tumor growth, including, (i) slowing down and (ii) complete growth arrest; (2) reduction in the number of tumor cells; (3) maintaining tumor size; (4) reduction in tumor size; (5) inhibition, including (i) reduction, (ii) slowing down or (iii) complete prevention, of tumor cell infiltration into peripheral organs; (6) inhibition, including (i) reduction, (ii) slowing down or (iii) complete prevention, of metastasis; (7) enhancement of anti-tumor immune response, which may result in (i) maintaining tumor size, (ii) reducing tumor size, (iii) slowing the growth of a tumor, (iv) reducing, slowing or preventing invasion and/or (8) relief, to some extent, of the severity or number of one or more symptoms associated with the disorder.

As used herein, "an ameliorated symptom" or "treated symptom" refers to a symptom which approaches a normalized value, e.g., is less than 50% different from a normalized value, preferably is less than about 25% different from a normalized value, more preferably, is less than 10% different from a normalized value, and still more preferably, is not significantly different from a normalized value as determined using routine statistical tests.

The terms "patient" or "individual" are used interchangeably herein, and refers to a mammalian subject to be treated.

By the term "modulate," it is meant that any of the mentioned activities, are, e.g., increased, enhanced, increased, augmented, agonized (acts as an agonist), promoted, decreased, reduced, suppressed blocked, or antagonized (acts as an antagonist). Modulation can increase activity more than 1-fold, 2-fold, 3-fold, 5-fold, 10-fold, 100-fold, etc., over baseline values. Modulation can also decrease its activity below baseline values.

As used herein, the term "administering to a cell" (e.g., an expression vector, nucleic acid, a delivery vehicle, agent, and the like) refers to transducing, transfecting, microinjecting, electroporating, or shooting, the cell with the molecule. In some aspects, molecules are introduced into a target cell by contacting the target cell with a delivery cell (e.g., by cell fusion or by lysing the delivery cell when it is in proximity to the target cell).

Thus, the term "cytokine" refers to any of the numerous factors that exert a variety of effects on cells, for example, inducing growth or proliferation. Non-limiting examples of cytokines include, IL-2, stem cell factor (SCF), IL-3, IL-6, IL-7, IL-12, IL-15, G-CSF, GM-CSF, IL-1α, IL-1β, MIP-1 α, LIF, c-kit ligand, TPO, and flt3 ligand. Cytokines are commercially available from several vendors such as, for example, Genzyme Corp. (Framingham, Mass.), Genentech (South San Francisco, Calif.), Amgen (Thousand Oaks, Calif.) and Immunex (Seattle, Wash.). It is intended, although not always explicitly stated, that molecules having similar biological activity as wild-type or purified cytokines (e.g., recombinantly produced cytokines) are intended to be used within the spirit and scope of the invention and therefore are substitutes for wild-type or purified cytokines.

"Costimulatory molecules" are involved in the interaction between receptor-ligand pairs expressed on the surface of antigen presenting cells and T cells. One exemplary receptor-ligand pair is the B7 co-stimulatory molecules on the surface of DCs and its counter-receptor CD28 or CTLA-4 on T cells. (See Freeman et al. (1993) Science 262:909-911; Young et al. (1992) J. Clin. Invest 90: 229; Nabavi et al. Nature 360:266)). Other important costimulatory molecules include, for example, CD40, CD54, CD80, and CD86.

The term "culturing" refers to the in vitro propagation of cells or organisms on or in media of various kinds, it is understood that the descendants of a cell grown in culture may not be completely identical (i.e., morphologically, genetically, or phenotypically) to the parent cell. By "expanded" is meant any proliferation or division of cells.

An "effective amount" is an amount sufficient to effect beneficial or desired results. An effective amount can be administered in one or more administrations, applications or dosages.

An "isolated" population of cells is "substantially free" of cells and materials with which it is associated in nature.

By "substantially free" or "substantially pure" is meant at least 50% of the population are the desired cell type, preferably at least 70%, more preferably at least 80%, and even more preferably at least 90%.

An "enriched" population of cells is at least 5% of the desired cell type. Preferably, the enriched population contains at least 10%, more preferably at least 20%, and most preferably at least 25% of the desired cell type.

The term "autogeneic", or "autologous", as used herein, indicates the origin of a cell. Thus, a cell being administered to an individual (the "recipient") is autogeneic if the cell was derived from that individual (the "donor") or a genetically identical individual (i.e., an identical twin of the individual). An autogeneic cell can also be a progeny of an autogeneic cell. The term also indicates that cells of different cell types are derived from the same donor or genetically identical donors.

Similarly, the term "allogeneic", as used herein, indicates the origin of a cell. Thus, a cell being administered to an individual (the "recipient") is allogeneic if the cell was derived from an individual not genetically identical to the recipient. In particular, the term relates to non-identity in expressed MEW molecules. An allogeneic cell can also be a progeny of an allogeneic cell. The term also indicates that cells of different cell types are derived from genetically nonidentical donors, or if they are progeny of cells derived from genetically non-identical donors.

A "subject" is a vertebrate, preferably a mammal, more preferably a human. Mammals include, but are not limited to, murines, simians, humans, farm animals, sport animals, and companion animals.

As used herein, "genetic modification" refers to any addition, deletion or disruption to a cell's endogenous nucleotides.

A "viral vector" is defined as a recombinantly produced virus or viral particle that comprises a polynucleotide to be delivered into a host cell, either in vivo, ex vivo or in vitro. Examples of viral vectors include retroviral vectors, adenovirus vectors, adeno-associated virus vectors and the like. In aspects where gene transfer is mediated by a retroviral vector, a vector construct refers to the polynucleotide comprising the retroviral genome or part thereof, and a therapeutic gene.

As used herein, the terms "retroviral mediated gene transfer" or "retroviral transduction" carries the same meaning and refers to the process by which a gene or a nucleic acid sequence is stably transferred into the host cell by virtue of the virus entering the cell and integrating its genome into the host cell genome. The virus can enter the host cell via its normal mechanism of infection or be modified such that it binds to a different host cell surface receptor or ligand to enter the cell.

Retroviruses carry their genetic information in the form of RNA. However, once the virus infects a cell, the RNA is reverse-transcribed into the DNA form that integrates into the genomic DNA of the infected cell. The integrated DNA form is called a provirus.

In aspects where gene transfer is mediated by a DNA viral vector, such as a adenovirus (Ad) or adeno-associated virus (AAV), a vector construct refers to the polynucleotide comprising the viral genome or part thereof, and a therapeutic gene. Adenoviruses (Ads) are a relatively well characterized, homogenous group of viruses, including over 50 serotypes. (See, e.g., WO 95/27071). Ads are easy to grow and do not integrate into the host cell genome. Recombinant Ad-derived vectors, particularly those that reduce the potential for recombination and generation of wild-type virus, have also been constructed. (See, WO 95/00655; WO 95/11984). Wild-type AAV has high infectivity and specificity integrating into the host cells genome. (See Hermonat and Muzyczka (1984) PNAS USA 81:6466-6470; Lebkowski et al., (1988) Mol Cell Biol 8:3988-3996).

Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression. Examples of suitable vectors are viruses, such as baculovirus and retrovirus, bacteriophage, cosmid, plasmid, fungal vectors and other recombination vehicles typically used in the art which have been described for expression in a variety of eucaryotie and prokaryotic hosts, and may be used for gene therapy as well as for simple protein expression.

Among these are several non-viral vectors, including DNA/liposome complexes, and targeted viral protein DNA complexes. Liposomes that also comprise a targeting antibody or fragment thereof can be used in the methods of this invention. This invention also provides the targeting complexes for use in the methods disclosed herein.

Polynucleotides are inserted into vector genomes using methods well known in the art. For example, insert and vector DNA can be contacted, under suitable conditions, with a restriction enzyme to create complementary ends on each molecule that can pair with each other and be joined together with a ligase. Alternatively, synthetic nucleic acid linkers can be ligated to the termini of restricted polynucleotide. These synthetic linkers contain nucleic acid sequences that correspond to a particular restriction site in the vector DNA. Additionally, an oligonucleotide containing a termination codon and an appropriate restriction site can be ligated for insertion into a vector containing, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColEI for proper episomal replication; versatile multiple cloning sites; and T7 and SP6 RNA promoters for in vitro transcription of sense and antisense RNA. Other means are well known and available in the art.

As used herein, "expression" refers to the process by which polynucleotides are transcribed into mRNA and translated into peptides, polypeptides, or proteins. If the polynucleotide is derived from genomic DNA, expression may include splicing of the mRNA, if an appropriate eukaryotic host is selected. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (Sambrook et al. (1989), supra). Similarly, a eukaryotic expression vector includes a heterologous or homologous promoter for RNA polymerase II, a downstream polyadenylation signal, the start codon AUG, and a termination codon for detachment of the ribosome. Such vectors can be obtained commercially or assembled by the sequences described in methods well known in the art, for example, the methods described above for constructing vectors in general.

The terms "major histocompatibility complex" or "MHC" refers to a complex of genes encoding cell-surface molecules that are required for antigen presentation to immune effector cells such as T cells. In humans, the WIC complex is also known as the HLA complex. Indogs the WIC complex is also known as the DLA complex. The proteins encoded by the WIC complex are known as "MHC molecules" In humans MHC molecules are classified into class I and class II MHC molecules. Human Class I WIC molecules include membrane heterodimeric proteins made up of an a chain encoded in the MHC associated noncovalently with β2-microglobulin. Human Class I WIC molecules are expressed by nearly all nucleated cells and have been shown to function in antigen presentation to CD8+ T cells. Human Class I molecules include HLA-A, -B, and -C in humans. Human Class II MHC molecules also include membrane heterodimeric proteins consisting of noncovalently associated and J3 chains. Human Class II MHCs are known to function in CD4+ T cells and, in humans, include HLA-DP, -DQ, and DR. In dogs, the MHC molecules are classified into class I, class II and class III molecules. Canine Class I WIC molecules are expressed by nearly all nucleated cells and have been shown to function in antigen presentation to T cells. Canine Class II molecules are expressed on antigen-presenting cells. Canine Class III molecules are not relevant to antigen presentation but can be important in other aspects of the immune system such as complement activation.

The term "MHC restriction" refers to a characteristic of T cells that permits them to recognize antigen only after it is processed and the resulting antigenic peptides are displayed in association with either a class I or class II MHC molecule. Methods of identifying and comparing MHC are well known in the art and are described in Allen M. et al. (1994) Human Imm. 40:25-32; Santamaria P. et al. (1993) Human Imm. 37:39-50; and Hurley C. K. et al. (1997) Tissue Antigens 50:401-415.

The term "sequence motif" refers to a pattern present in a group of 15 molecules (e.g., amino acids or nucleotides). For instance, in one embodiment, the present invention provides for identification of a sequence motif among peptides present in an antigen. In this embodiment, a typical pattern may be identified by characteristic amino acid residues, such as hydrophobic, hydrophilic, basic, acidic, and the like.

The term "peptide" is used in its broadest sense to refer to a compound of two or more subunit amino acids, amino acid analogs, or peptidomimetics. The subunits may be linked by peptide bonds. In another embodiment, the subunit may be linked by other bonds, e.g. ester, ether, etc.

As used herein the term "amino acid" refers to either natural and/or 25 unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is commonly called a polypeptide or a protein.

As used herein, "solid phase support" is used as an example of a "carrier" and is not limited to a specific type of support. Rather a large number of supports are available and are known to one of ordinary skill in the art. Solid phase supports include silica gels, resins, derivatized plastic films, glass beads, cotton, plastic beads, alumina gels. A suitable solid phase support may be selected on the basis of desired end use and suitability for various synthetic protocols. For example, for peptide synthesis, solid phase support may refer to resins such as polystyrene (e.g., PAM-resin obtained from Bachem Inc., Peninsula Laboratories, etc.), POLYHIPE® resin (obtained from Aminotech, Canada), polyamide resin (obtained from Peninsula Laboratories), polystyrene resin grafted with polyethylene glycol (TentaGel®, Rapp Polymere, Tubingen, Germany) or polydimethylacrylamide resin (obtained from MilligenlBiosearch, California). In a preferred embodiment for peptide synthesis, solid phase support refers to polydimethylacrylamide resin.

"Host cell" or "recipient cell" is intended to include any individual cell or cell culture which can be or have been recipients for vectors or the incorporation of exogenous nucleic acid molecules, polynucleotides and/or proteins. It also is intended to include progeny of a single cell, and the progeny may not necessarily be completely identical (in morphology or in genomic or total DNA complement) to the original parent cell due to natural, accidental, or deliberate mutation. The cells may be prokaryotic or eukaryotic, and include but are not limited to bacterial cells, yeast cells, animal cells, and mammalian cells, e.g., murine, rat, simian or human.

An "antibody" is an immunoglobulin molecule capable of binding an antigen. As used herein, the term encompasses not only intact immunoglobulin molecules, but also anti-idiotypic antibodies, mutants, fragments, fusion proteins, humanized proteins and modifications of the immunoglobulin molecule that comprise an antigen recognition site of the required specificity.

An "antibody complex" is the combination of antibody and its binding partner or ligand.

A "native antigen" is a polypeptide, protein or a fragment containing an epitope, which induces an immune response in the subject.

The term "isolated" means separated from constituents, cellular and otherwise, in which the polynucleotide, peptide, polypeptide, protein, antibody, or fragments thereof, are normally associated with in nature. As is apparent to those of skill in the art, a non-naturally occurring polynucleotide, peptide, polypeptide, protein, antibody, or fragments thereof, does not require "isolation" to distinguish it from its naturally occurring counterpart. In addition, a "concentrated", "separated" or "diluted" polynucleotide, peptide, polypeptide, protein, antibody, or fragments thereof, is distinguishable from its naturally occurring counterpart in that the concentration or number of molecules per volume is greater than "concentrated" or less than "separated" than that of its naturally occurring counterpart. A polynucleotide, peptide, polypeptide, protein, antibody, or fragments thereof, which differs from the naturally occurring counterpart in its primary sequence or for example, by its glycosylation pattern, need not be present in its isolated form since it is distinguishable from its naturally occurring counterpart by its primary sequence, or alternatively, by another characteristic such as glycosylation pattern. Although not explicitly stated for each of the inventions disclosed herein, it is to be understood that all of the above embodiments for each of the compositions disclosed below and under the appropriate conditions, are provided by this invention. Thus, a non-naturally occurring polynucleotide is provided as a separate embodiment from the isolated naturally occurring polynucleotide. A protein produced in a bacterial cell is provided as a separate embodiment from the naturally occurring protein isolated from a eukaryotic cell in which it is produced in nature.

A "composition" is intended to mean a combination of active agent and another compound or composition, inert (for example, a detectable agent, carrier, solid support or label) or active, such as an adjuvant.

A "pharmaceutical composition" is intended to include the combination of an active agent with a carrier, inert or active, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin, REMINGTON'S PHARM. SCI, 15th Ed. (Mack Publ. Co., Easton (1975)).

As used herein, the term "inducing an immune response in a subject" is a term well understood in the art and intends that an increase of at least about 2-fold, more preferably at least about 5-fold, more preferably at least about 10-fold, more preferably at least about 100-fold, even more preferably at least about 500-fold, even more preferably at least about 1000-fold or more in an immune response to an antigen (or epitope) can be detected (measured), after introducing the antigen (or epitope) into the subject, relative to the immune response (if any) before introduction of the antigen (or epitope) into the subject. An immune response to an antigen (or epitope), includes, but is not limited to, production of an antigen-specific (or epitope-specific) antibody, and production of an immune cell expressing on its surface a molecule which specifically binds to an antigen (or epitope). Methods of determining whether an immune response to a given antigen (or epitope) has been induced are well known in the art. For example, antigen specific antibody can be detected using any of a variety of immunoassays known in the art, including, but not limited to, ELISA, wherein, for example, binding of an antibody in a sample to an immobilized antigen (or epitope) is detected with a detectably-labeled second antibody (e.g., enzyme-labeled mouse anti-human Ig antibody). Immune effector cells specific for the antigen can be detected any of a variety of assays known to those skilled in the art, including, but not limited to, FACS, or, in the case of CTLs, $^{51}$CR-release assays, or $^{3}$H-thymidine uptake assays.

By substantially free of endotoxin is meant that there is less endotoxin per dose of cell fusions than is allowed by the FDA for a biologic, which is a total endotoxin of 5 EU/kg body weight per day.

By substantially free for mycoplasma and microbial contamination is meant as negative readings for the generally accepted tests know to those skilled in the art. For example, mycoplasm contamination is determined by subculturing a cell sample in broth medium and distributed over agar plates on day 1, 3, 7, and 14 at 37° C. with appropriate positive and negative controls. The product sample appearance is compared microscopically, at 100×, to that of the positive and negative control. Additionally, inoculation of an indicator cell culture is incubated for 3 and 5 days and examined at 600× for the presence of mycoplasmas by epifluorescence microscopy using a DNA-binding fluorochrome. The product is considered satisfactory if the agar and/or the broth media procedure and the indicator cell culture procedure show no evidence of mycoplasma contamination.

The sterility test to establish that the product is free of microbial contamination is based on the U.S. Pharmacopedia Direct Transfer Method. This procedure requires that a pre-harvest medium effluent and a pre-concentrated sample be inoculated into a tube containing tryptic soy broth media and fluid thioglycollate media. These tubes are observed periodically for a cloudy appearance (turpidity) for a 14 day incubation. A cloudy appearance on any day in either medium indicate contamination, with a clear appearance (no growth) testing substantially free of contamination.

EXAMPLES

Example 1

Development of Ghost Cells for Numerical and Targeted Expansion of T Cells, NK Cells, B Cells, and/or Other Immune Cells or for Infusion to Treat Cancers and Autoimmune Diseases "Ghost cells" are immortalized cell lines genetically modified to express immune co-stimulatory molecules anchored to lipid rafts via a glycosylphosphatidylinositol anchor (GPI) that is added to the protein during ER post-translational modification. The term "ghost cell" results from the preparation method to render the cell empty and non-viable. Ghost cell lines will undergo a specific hypotonic lytic procedure that will extract all intracellular components, but allows plasma membrane, GPI anchored proteins, and lipid rafts to remain intact. Hence, rendering the components "ghosts". Ghost cells are used for the numerical and targeted expansion of canine, human, feline, and equine lymphocytes through the placement of specific immunoediting genetic pressures on lymphocytes. The use of GPI anchors, use of lipid rafts, use of various species (human, canine, feline, and equine), application of immunoediting pressures for expansion, and use of a specific hypotonic lytic procedure constitute new art to which the invention pretains. Ghost cells are a human malignant cell line that have been genetically modified to express T-cell human molecules including, but not limited to, CD137L, CD86, CD64, HLA-Cw 3, and HLA-Cw 5. The co-stimulatory molecules will be attached to the ghost cell membrane using glycosylphosphatidylinositol anchors (GPI). The GPI anchoring will ensure that the transfected genes are expressed on the cell surface in close proximation inside lipid rafts, rather than expressed randomly across the cell plasma membrane. A self-inactivating transposase and transposon system or a drug selection equipped DNA printed plasmid will be used to introduce the genes of interest via lipofectamine transfection. Human cell lines, such as K562, 722.21, Jurkat or other adherent/suspended cell line will serve as the basis for the ghost cells. The term "ghost cell" results from the method of preparing the cells to stimulate NK and T cell expansion such that they are empty and non-viable. Ghost cell lines developed and tested will undergo a specific hypotonic lytic procedure that will extract the intracellular components, but will leave the cell membrane and lipid rafts intact, therefore, rendering them ghosts.

Figure 2A:
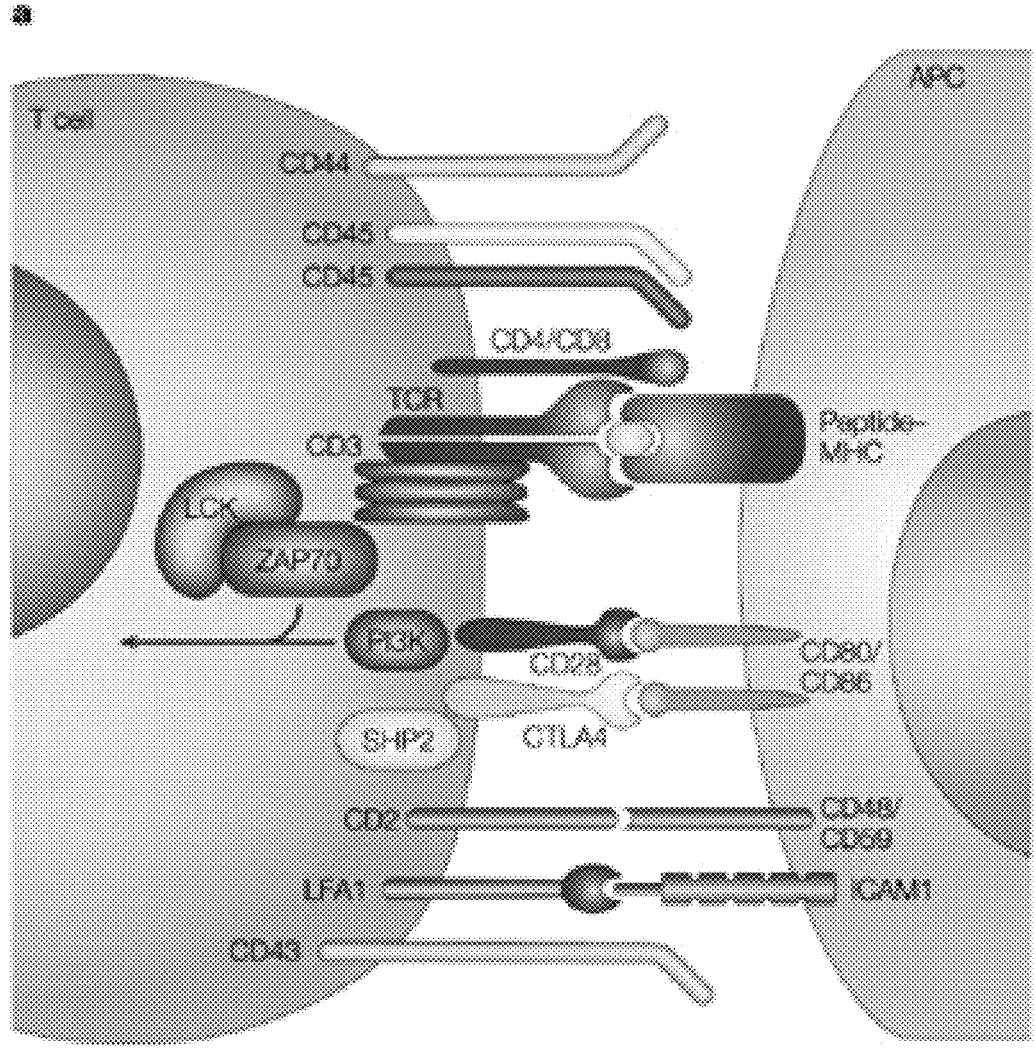
FIG. 2A shows T-cell-antigen recognition and the immunological synapse (Johannes B. Huppa & Mark M. Davis, Nature Reviews Immunology 3, 973-983 (December 2003)).
Figure 2B:
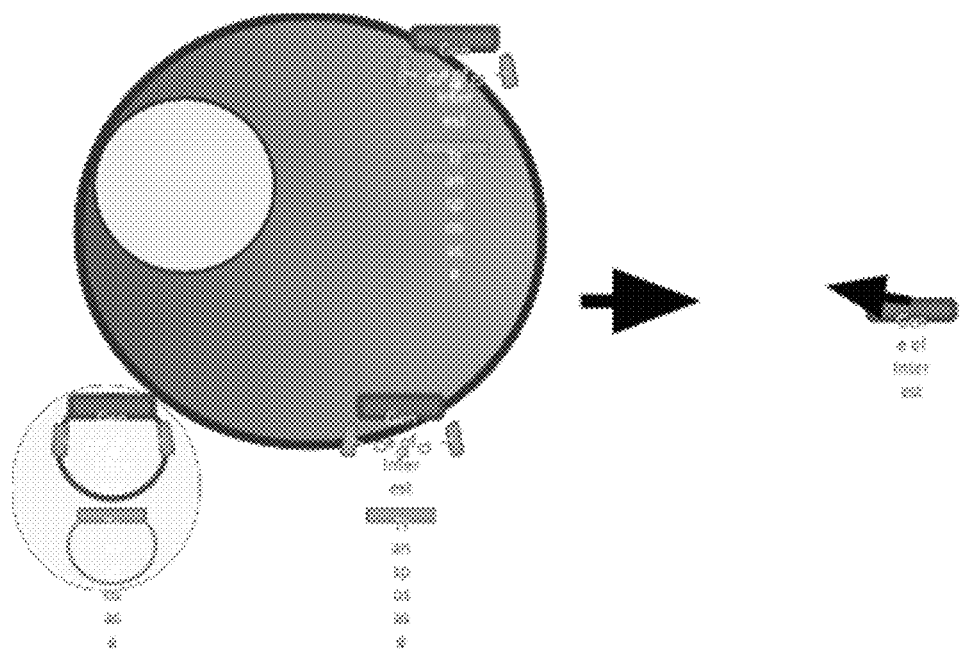
FIG. 2B shows lipofectamine vesicles containing gene of interest transposon and transposase entering the intracellular and nuclear membranes. The transposase cutting the gene of interest out of the transposon and randomly inserting it into the pre-ghost cell's DNA.
Figure 3:
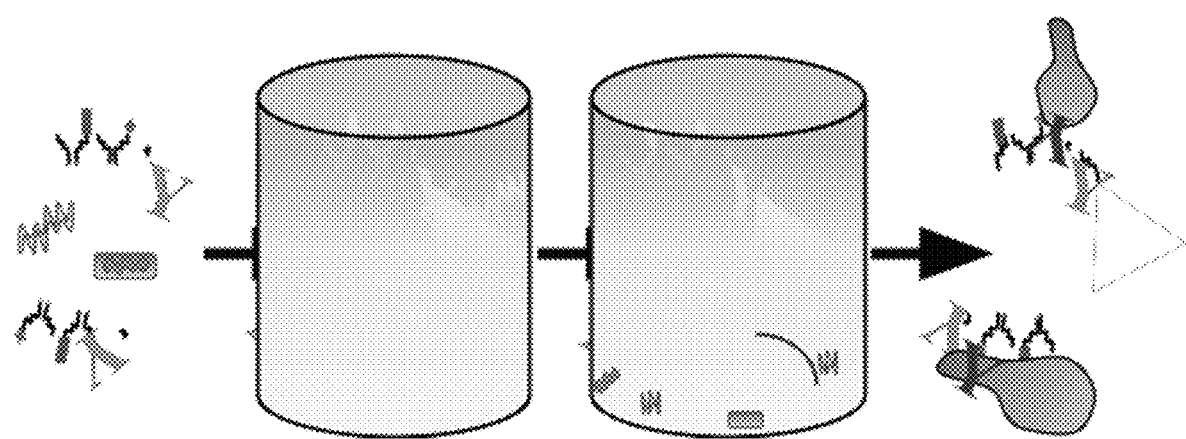
FIG. 3 shows the creation of ghost cells expressing GPI anchored proteins on cell membrane lipid rafts using hypotonic solution for acute cell lysis and immediate co-culture with mammalian lymphocytes.
Figure 4:
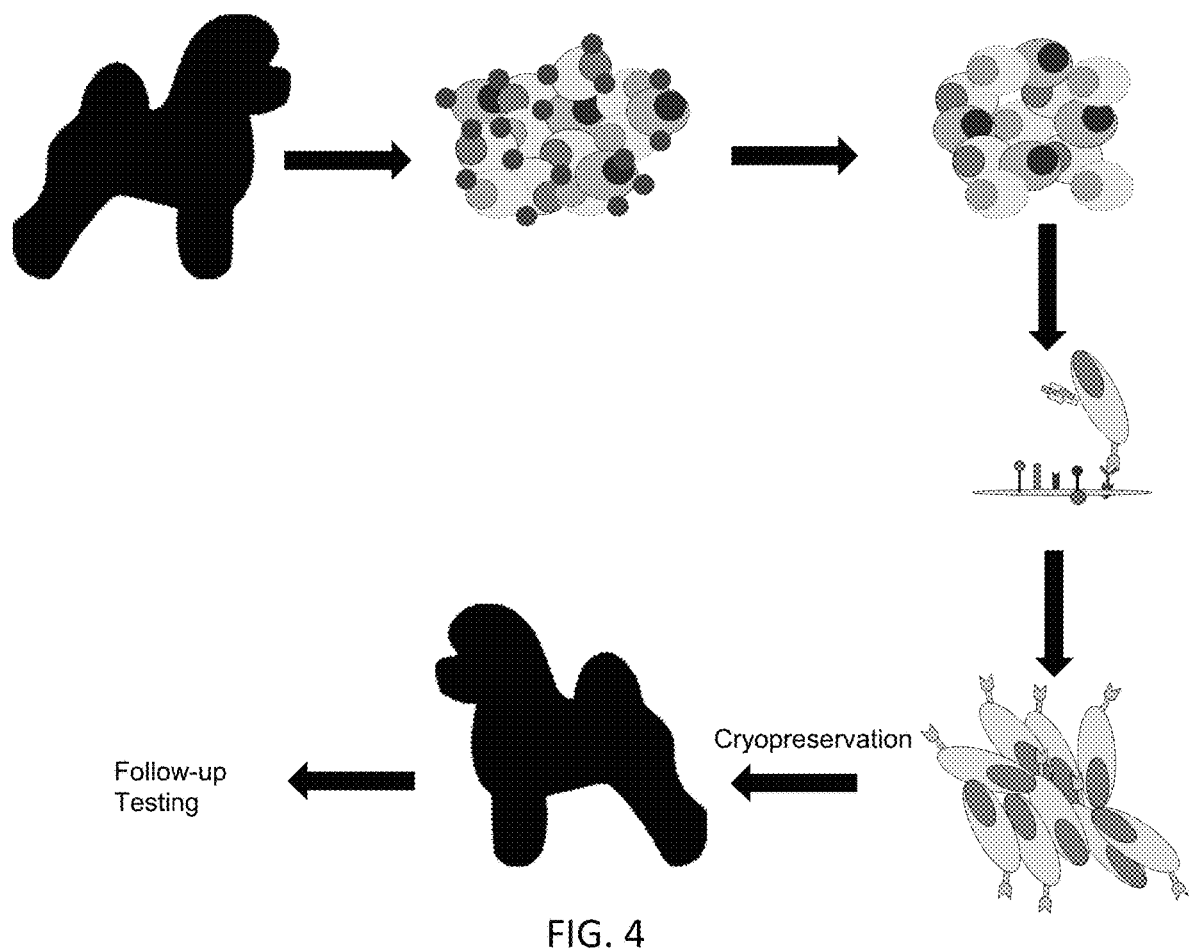
FIG. 4 shows the process of mammalian lymphocytes isolated and expanded on ghost Cells, cryopreserved and re-infused.
Figure 5:
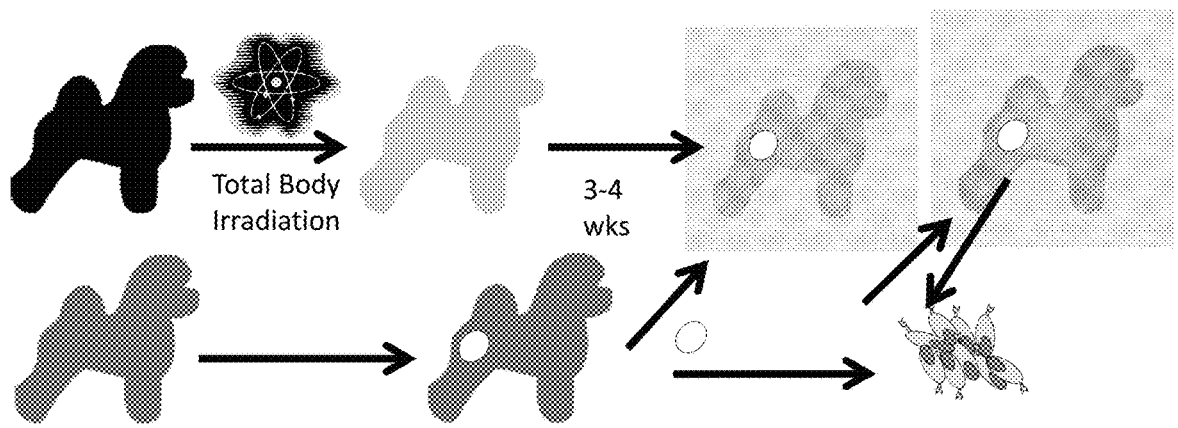
FIG. 5 shows the reconstitution of a normal, intact immune system after total body radiation and hematopoietic stem cell transplant to treat a malignancy and the associated tumor-driven dysfunctional and ablated immune system.
Figure 6:
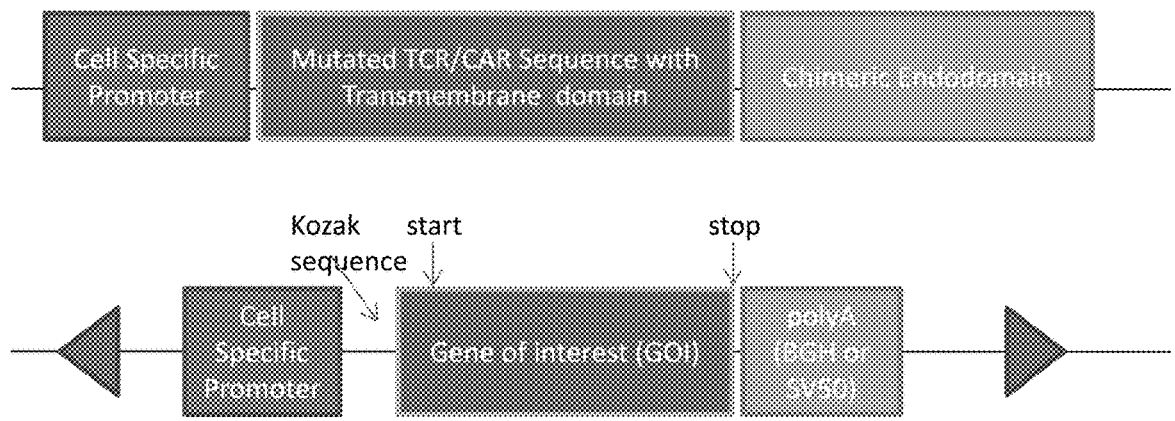
FIG. 6 is a vector map of the novel generation of TCR and CAR sequences to be expressed in primary cells. Cell Specific Promoter: CD3z, BCR, NKR (Species specific also) for added safety benefit. The CAR/TCR will only work in a specific cell type cannot be transferred. Mutated TCR/CAR Sequence of choice with transmembrane domain Chimeric Endodomain: CD3z, CD28, 41BB as possible combinations for more potent killing of tumor. Kanamycin selection for clinical vector.
Figure 7:
FIG. 7 is a vector map of co-stimulatory molecules, cytokines, and antigens to be anchored with GPI for lipid raft sequestering on the plasma membrane of a ghost cell trainer. CMV: Human CMV promoter; SP: Signaling Peptide for cellular location: Gene of Interest: Co-Stimulatory Molecule; GPI: CD55 Propeptide and Lipidation GPI Signaling Anchor. This can be interchanged with CD64, CD86, CD137L, and human IL-15. All other regions will constant regardless of the Gene of Interest. This can be used for the ghost cells for NK and T cell expansion. For NK expansion, anti-NK2GD antibody can be loaded on the CD64 receptor prior to cryopreservation and ghosting.

(I) Development of Plasmids that Contain T-Cell Co-Stimulatory Molecules and HLA-Cw*3 and 5 Molecules DNA plasmids and vectors will be created either using DNA printing, 3D printing, bacterial transformation, and/or other methods. Plasmids and vectors will be codon optimized for the mammalian cell species utilized and will incorporate species specific promoters such as, but not limited to CMV, EF 1-alpha, CD3, and KIR. Genes of interest will be printed or cloned either into (i) a transposon vector with an associated transposase to cleave the gene of interest from the transposon and insert it at specific repetitive sites into the cell's or (ii) a type of viral vector that can be used to transduce a cell randomly with the gene of interest to cause protein expression. DNA or FIG. 2B shows possible plasmid maps.

(II) Isolation of Canine Peripheral Blood Mononuclear Cells (PBMC)

Canines diagnosed with an applicable malignancy will have peripheral blood collected before SOC treatment or an apheresis collected post Neupogen dosing and prior to HSCT. The apheresis volume range for HSCT is 120 to 350 ml. The volume collected depends on size (weight) of dog and is collected on a TerumoBCT Spectra or Optia machine. If apheresis is not possible, 50 to 150 mls of peripheral blood will be drawn via intravenous catheter in an extremity chosen by the attending veterinarian into a blood bag designated for clinical use. For smaller volumes, EDTA vacutainers may be used. Some veterinarians may elect to pre-treat the patient with Neupogen prior to peripheral blood collection to increase PBMC numbers. The sample will be overnighted to a certain facility at room temperature, unless the daytime temperatures are above 85F. Then, the sample should be sent with an ice pack to maintain cell viability and status. Upon arrival at the facility, the patient sample will receive a unique number identifier that will be linked to the patient's attending veterinarian's office client number. At this time, data from the patient information sheet will be entered into the database. The sample will be decanted and diluted with Hank's Balanced Salt Solution (HBSS) at a ratio of 1:5 (sample:HBSS). Samples will be overlayed onto Ficoll at a ratio or 1:2 (Ficoll:diluted sample) in 50 ml centrifuge tubes and centrifuged for 40 minutes at 400×g with no brake. The PBMC layer will be removed using sterile, disposable transfer pipettes and diluted 1:1 with HBSS before centrifugation at 450×g for 15 minutes with medium brake. Supernatant will be discarded and the cells will be diluted again with HBSS at a 1:1 ratio before centrifugation at 400×g for 10 minutes. Fifty percent of the PBMCs will be cryopreserved as back up, 45% will be used for expansion on ghost cells, and 5% will be phenotyped by flow cytometry to provide a patient baseline and placed in their chart.

(III) Canine, Feline, Human, or Equine PMBC, T-Cell, and Infusion Sample Cryopreservation Canine, feline, human, or equine PBMCs after isolation will be cryopreserved in in-house freeze media (FM) or commercially derived FM. This media will be made in batches with accompanying recorded batch numbers, aliquoted and frozen until use, and undergo sterility testing for bacteria, fungus, mycoplasma, and endotoxin for quality control. FM may contain the following solutions: 40-70% Saline (PBS, HBSS, etc), 20-40% canine, feline, human, or equine serum, 1-10% Dimethyl sulfoxide (DMSO) and may be filtered sterilized one to three times. The serum will be heat inactivated at 65 C for 30-60 minutes to inactivate the complement proteins before aliquoting and freezing until use. The serum will be purchased from regulatory approved sources. DMSO and HBSS will be purchased commercially. After centrifugation and removal of supernatant, T cells will be resuspended in thawed (4 C temp) FM at a concentration range between $5\times10^6$ to $1\times10^8$ cells/ml. In the instances of back-up cryopreservation at isolation and after stimulations, cells will be cryopreserved in 2-10 ml cryovials using isopropanol containing canisters in −80 to −65 C for 24-72 hrs before transfer to liquid nitrogen storage for permanent storage. Samples for patient's infusions will be cryopreserved in bags with ports suitable for cryopreservation and infusion. Samples earmarked for infusion may be cryopreserved using a rate-controlled freezer for 45-52 minutes using a specific program and then will be transferred to liquid nitrogen for storage until infusion. Twenty-four hours prior to infusion, the T cells will be sent to the veterinarian on dry ice in Styrofoam and cardboard container overnight with a copy of the infusion protocol, follow-up instructions, and results of the T-cell quality control and assurance. Samples will be tested flow cytometrically for lack of B cells (less than 5%), majority T cells (greater than 50%), CD4 and CD8 percentages, viability, lack of ghost cells (less than 5%), and presence of the TCR or CAR if transfected (greater than 10% positive).

(IV) HLA-Cw*3 and/or 5 Positive Ghost Cell Transfection, Cryopreservation, and Formation Human cells lines (either adherent or in suspension) expressing HLA-C*3 and/or 5 will be transfected with genes of interest (human CD86, CD64, CD137L, and IL-15 (all extracellular domains will be expressed on GPI anchors)) embedded in a piggybac transposase/transposon system. Genes will be transfected using the DMRIE-C reagent which is commercially sold by Invitrogen. This protocol will be optimized for each cell line and gene. If the human cell line does not endogenously express the protein HLA-C*3/5, then it will be transfected into the cell line as well using the piggybac technology. Cell lines to be developed into ghost cells may include, but will not be limited too, K562, 722.21, and Jurkat. Master cell banks of each line prior and post stable transfection will be created and stored in liquid nitrogen. Prior to transfection, cell lines may undergo cell line fingerprinting to ensure the correct identity of the line. Cell lines will be expanded at 39° C. in a humidified incubator using complete media (CM: RPMI, 10% 100× glutamax, 10% fetal calf serum (FBS)). Cell lines will be cryopreseved in FM (10% DMSO, 50% HBSS, 40% FBS) at a concentration of 2 to $4\times10^7$ cells/ml in 2 ml cryovials. Transient transfection will be determine 24 hours post transfection using flow cytometry and antibodies recognizing the inserted gene's protein expression. Single color and no stained controls will be used to aid in color compensation and expression analysis. Ghost cell lines will receive 50% to 100% media changes 2 to 3 times a week to maintain the cellular concentration at $2\times10^6$ cells/ml of CM. Stable expression will be measured seven days post transfection utilizing the 24 hour measurement protocol and analysis. Positive expressing cell populations will be sorted using antibodies and magnetic columns or using Influx cell sorter. The positive fraction will be expanded as outlined previously and will be sorted weekly or bimonthly until all of the cells express all inserted genes. Quality control and assurance will be completed on all master and working ghost cell banks (Sterility, Endotoxin, Mycoplasma, Viability, Gene Expression, Fingerprinting).

Ghost cells will be formed using hypotonic lysis prior to co-culture with T-cells. The hypotonic lysis solution will contain cocktails to inhibit protein degradation (tyrosine, acid and alkaline phosphatases; serine proteases; trypsin, chymo-trypsin, plasmin, and amino-peptidases; cystein proteases; L-isozymes, and serine-threonine protein phosphatases) diluted in distilled water with a pH of 7.0. Ghost cell lines will be incubated for 5 to 14 minutes, depending on the ghost cell line.

More specifically, to create a ghost cell for immune cell activation or "ghostbusting", a ghost cell trainer (e.g., transfected cell line) are transferred to 10-250 ml centrifuge tube and centrifuged at 400G for 5 to 12 minutes. Supernatant will be removed and the ghost cell trainer cells resuspended in saline before quantification and viability measurement using AO/PI. Ghost cell trainer cells will be washed, centrifuged using the same technique and supernatant removed. Ghost cell trainers will be resuspended in the above described hypotonic solution containing a protease inhibitor for period of time (1 to 14 minutes) depending on the ghost trainer cell number (1e6 to 1e9 cells/mL of hypotonic lysing solution). Ghost cells will be centrifuged at 400 to 2500 g for 3 to 15 minutes. Supernatant will be removed and viability assessed using standard AO/PI cellometer imaging.

Viability must be less than 30% before co-culture with immune cells. Ghost cells will be resuspended in the appropriate immune cell complete media in 5 mLs.

Viability and cell size will be assessed using trypan blue as measured by a cellometer post incubation and washing with RPMI media containing protease inhibitor cocktails at 200×g for 10 minutes. Solutions with cell pellets/lysates less than 20% will immediately prepared for co-culture. Membrane integrity, protein expression and lipid raft integrity endurance will be assessed using antibodies and single quantum dots connected to a cholera toxin B subunit for microscopic visualization and quantification. Cholera toxin B subunit it a molecule that binds to ganglioside, GM1, which is a major mammalian cell lipid raft constituent. This visualization will allow optimization of the incubation period, as well as, molarity of the solution by determining the optimal number of lipid rafts necessary for canine T-cell activation. We will correlate this data with viability and include it our quality control ghost cell panel.

(V) Canine T-Cell Expansion on Ghost Cells

Canine T cells will be co-cultured with HLA-Cw*3 and 5 positive ghost cells to expand a TCR-specific oligoclonal T-cell population that recognizes HLA-Cw*3 and 5 presented antigens, such as Importin subunit alpha. Canine T cells will be expanded in a 39 C humidified incubator in CM (RPMI, 1-100% 100× glutamax, 1-100% FBS) at a concentration of 1.5 to $2 \times 10^6$ T cells/ml of CM. Exogenous human cytokines (IL-21 and IL-2) will be added to the cultures 2 to 3 times per week at a concentration of and, respectively. IL-2 will not be added for the first 7 to 10 days. T cells will be re-stimulated with ghost cells every 4 to 8 days until a clinically sufficient number of T cells has been reached for each patient. This number is based on body surface area (BSA) calculated from the weight of the dog. Ten percent of every other stimulation will be cryopreserved as back-up. Ghost cells will be added to the T-cell culture at a ratio ranging from (Ghost Cell: T-cell) 1:1 to 1:3. The exact ratio will be determine through optimization experiments as this method of stimulation vastly differs from the addition of viable, but gamma-irradiation apoptotically-induced artificial antigen presenting cells. T cells may be phenotyped flow cytometrically for CD3, CD4, CD8, CD21, CCR7, Granzyme B, Perforin, IFN-g, and CD32, among others at days 7-47 and prior to cryopreservation for infusion. Cells may be expanded 7 days or greater and we expect that not all patient samples will expand similarly or at all. All cultures may be checked weekly for mycoplamsa and endotoxin.

(VI) Infusion Protocol for Veterinarians

1.) Sterilely place intravenous catheter and T-port in patient. Have all supplies ready; 2.) Remove frozen product/unit. Seal in clean water impermeable plastic bag; 3.) Place unit/sealed bag into warm water bath or bowl of water (37° C.); 4.) Gently rock bag in warm water until fully thawed; 5.) Remove product/unit from sealable bag; 6.) With clean/dry gloves sterilely place filtered bag access spike; 7.) Gently withdraw entire contents of bag into 60 ml syringe with 18 g needle; 8.) Instill 10-20 ml sterile 0.9% NaCl+10 ml air into bag/unit from pre-drawn syringe; 9.) Gently mix bag and withdraw contents into 60 ml syringe from above; 10.) Slowly administer product over 10 minutes (5 ml/minute maximum rate); and 11.) Flush IV catheter with pre-drawn 5-10 ml of sterile 0.9% NaCl.

Check and record the following: temperature, heart rate, respiratory rate, and reactions at 5, 10, and 30 minutes post T-cell infusion, as well as, pre-infusion. This is to monitor for any immune reactions that may occur. If an adverse reaction is recorded, CAVU Biotherapies must be notified in writing and a 10 ml peripheral blood and serum sample at the time of the reaction must be collected and sent to CAVU Biotherapies for immune analysis. The following supplies are necessary for each infusion: standard intravenous catheter 20-22G, T-port, #1 60 ml leur-lok syringe, #1 30 ml leur-lok syringe, #1 10 ml leur-lok syringe, #3 18G needles, new sterile 0.9% NaCl bag, Hemo Tap Filter (Bag Access) Spike, warm clean water bath or preheated warm water in clean bowl (370 C), sealable plastic bag, Nitrile gloves, and a dedicated thermometer.

The time from start of thaw to completion of the T-cell infusion is 15 minutes (max 30 minutes). After 15 minutes, the viability of the infusion begins to diminish. Other information necessary for clinicians: pre-place needles onto syringes; pre-draw 10-20 ml 0.9% NaCl+10 ml air; volume of flush at doctor preference; pre-draw 5-10 ml sterile 0.9% NaCl for post infusion IV flush; insure bag/unit and access ports remain clean and dry at all times; and wear gloves at all times.

(VII) Osmolytic Creation of Ghost Cells

To create a ghost cell for lymphocyte expansion or "ghostbusting", a transfected cell line will be subjected to a hypotonic solution containing a protease inhibitor for an optimized period of time (1 to 5 minutes). This pore forming solution will cause the initiation of caspase 3, 8 and mitochondrial apoptotic cascade, as well as, create a large hole in the weaker side of the cell membrane to allow the entire intracellular contents to leak out. Trypan blue and the cellometer will be utilized to gauge viability every 12 to 24 hours for a period of 72 hours. During the first 6 hours, ghost cells will be monitored for lysis, membrane integrity, and apoptotic cascade initiation. Optimization of hypotonic solution recipes and incubation periods will be completed at this time. While the cell will be dead, the cell membrane with the lipid rafts will remain relatively intact to allow T-cell binding. Hence, the origination of the term "ghost cell". Hypotonic stress initiates apoptotic pathways rather than necrotic pathways, which are more advantageous for T-cell activation (Selzner 2004). Hypotonic stress causes cell death through a caspase and mitochondrial-dependent mechanism, as well as, up-regulates GPI protein and MHC expression. Volume sensitive ATP release plays a key role in the induction of apoptosis following hypotonic exposure. This is a novel way of inducing T-cell activation as current methods use more expensive and regulatory complex cesium irradiation to kill the tumor cell lines. This irradiation method allows the tumor cell lines continue to function as highly viable artificial antigen presenting cells in culture for days after irradiation. These artificial antigen presenting cells remain intact and have the capacity to proliferate, move, and secrete immunosuppressive cytokines. Ghost cells remove the immunosuppressive cytokine secretion (IL-10 and TGF-B), prohibit tumor cell line clustering to inhibit T-cell mediated lysis, prohibit T-cell tolerance to tumor antigens, and prohibit possible tumor proliferation and viability, while improving synaptic formation and strength to increase T-cell expansion.

Example 2

Antigen-Specific TCR HLA-Cw*3 and 5 Driven Autologous and Allogeneic T-Cell Expansion on Ghost Cells T cells will be co-cultured with these ghosts 1 to 3 times per week with the addition of exogenous human IL-2 and IL-21 cytokines, 2 to 4 times per week. Once clinically sufficient numbers of HLA-Cw*3 and 5 tumor targeted T cells are expanded, cells will undergo quality control and assurance after cryopreservation for infusion. TCR sequencing will be completed on optimized cultures to support oligclonal and TCR-specific T-cell growth.

By targeting HLA-Cw*3 and 5 TCR recognizing T cells, we will expand an oligoclonal TCR population recognizing TAAs, like Importin, which are presented on this specific molecule. This will differ from past methods which relied on OKT3-driven canine T-cell expansion, which drives polyclonal non-specific expansion. By targeting TAAs expressed through HLA-Cw*3 and 5, we will be expanding a TCR-specific T cells. Human HLA-Cw*3 and 5 cross reacts with several animal species, specifically porcine (cited), and there is a 91% homology between the human and canine when the sequences are BLASTed against each other.

To drive TCR-specific expansion, ghost cells will be hypotonically lysed as described above and centrifuged immediately before addition the PBMC/T cells. Ghost cells will be added at a ratio (ghost cell to T cell) from 1:2 to 1:4, once to three times per week. Exogenous human cytokines (IL-2 and IL-21) will be used to accelerate the desired CD8 or CTL T-cell expansion. Concentrations will be optimized to create optimal expansion and activation with ghost cells and lipid rafts, but will start at 2 to 3 times per week dosing. Canine T cells and Ghost cells will be grown in a humidified incubator at 39 C, which is approximately the ambient temperature of a normal dog. T cells will be weekly enumerated using trypan blue and cellometers, phenotyped (CD3, CD4, CD8, CD25, CD21, CCR7) using flow cytometery and viability analyzed to ensure clinically sufficient numbers of CTLs can be produced. Prior to cryopreservation, T cells will be tested for granzyme B and IFN-γ production.

TCR will be sequenced on 6 different expanded patient samples to show TCR oligoclonal population distribution. Canine T-cell gene specific Nanostring panels may be employed in 12 patient samples (pre and post expansion) to show that T-cell dysfunction has been overcome using ghost cell manipulation. For cryopreservation purposes, a quality control and assurance protocol will be developed that measures viability by trypan blue, phenotype (CD3, lack of ghost cells, lack of B cells), sterility (bacteria, fungal), mycoplasma, and endotoxin levels. This will be completed on all infusion samples. Infusion samples will be cryopreserved in cryopreservation bags using an in-house produced and quality tested freezing media (10% DMSO, 50% HBSS, 40% Canine Serum from Northwest Blood Bank) and frozen to −100° C. within 3 hours of final harvest. Freezing will take place using a Rate Controlled Freezer and the bags will be immediately transferred to liquid nitrogen for storage.

Example 3

TCR Sequencing on T Cells Expanded on Other Ghost Cell Lines to Identify New TCR Sequences and Targets Participating veterinarian oncologists and veterinarians will routinely test for relapse using clonality testing, pathology, and immunophenotyping of the peripheral blood and suspicious growths. Peripheral blood and fine needle aspirates of the complying canine patients will be submitted to O'Connor Immunogenetics to determine dominant TCR clone analysis using next generation sequencing.

Companion canines will be clinically for relapse by participating veterinarians and veterinarian oncologists. PCR or clonal testing on peripheral blood samples will determine B-cell lymphoma relapse. Tumor pathology or imaging may be completed to determine reoccurrence in other malignancies. Along with clonal testing and pathology, peripheral blood T-cell phenotypes (CD3 numbers, CD3CD4:CD3CD8 ratio numbers) will be routinely (monthly or every other month) monitored to determine if there are changes (decreased CD3 numbers, increased CD3CD4:CD3CD8 ratio numbers) that suggest relapse.

In those companion canines that respond spontaneously, peripheral blood or tumor infiltrating T cells at these time points will be collected through 10 ml blood draws and/or fine needle aspirates (FNA). T cells will be separated using a ficoll density centrifugation protocol established in Specific Aim #1. The PBMC will be submitted for TCR sequencing using 25-30 nucleotide primers for use on MiSeq technology.

The dominant TCR sequences observed from in-house bioinformatic analysis will determine if the infused T cells have persisted and developed into a memory state or if the tumor has antigenically mutated due to immunoediting and another tumor-targeting TCR has developed. Mass spectrometry and protein isolation techniques will be employed to discover the new TAA. Resulting data will be used for the potential development and generation of alternative TAA TCR-specific T cells that may or may not be genetically modified for relapsed canines and these data/sequences may be licensed for human use.

Example 4

HLA-Cw*3/5 Positive T Cell and NK Cell Infusion Specific Dosing Regimens

Standard of care therapies may include CHOP, abbreviated CHOP, tumor targeted gamma-irradiation, surgery, and autologous or allogeneic hematopoietic stem cell transplantation (HSCT). Pre-infusion conditioning treatments will include high dose cytoxan and possible total body irradiation (TBI) at a dose of less than 2 Gy. Immunomodulating treatments not only provide efficacious treatment while the cellular therapy is being prepared, but can provide a suitable environment for the infusion to expand, lyse targets, and engraft.

The following treatments may be used as disease-stabilizing or remission-inducing treatments while the T-cell are being manufactured: CHOP, abbreviated CHOP, MOPP, doxil, doxorubicin, tumor-targeted gamma irradiation, surgery, prednisone and autologous or allogeneic hematopoietic stem cell transplantation (HSCT) or donor lymphocyte infusions (DLI).

Pre-infusion conditioning treatments will include high dose cytoxan and possible total body irradiation at a dose of less than 2 Gy. Immunomodulating treatments not only provide efficacious treatment while the cellular therapy is being prepared, but can provide a suitable environment for the infusion product to expand, lysed targets, and engraft. Pre-conditioning treatments remove immunosuppressive cells and cytokines, modulate the tumor and its microenvironment, removes single cell metastases, and creates space in the lymphoid compartment for the ex vivo expanded HLA-Cw*3 and 5 TAA recognizing T cells.

In companion canines diagnosed with OS, tumors will be treated with 2 fractionated doses of 8 Gy to equal a total dose of 16 Gy over 48 to 72 hours. Forty-eight hours post the final dose of radiation, the first T-cell dose of $5\times10^8$ cells/m$^2$ will infused intravenously. The patient will be monitored for 1.5 to 3 hours post infusion for any adverse reactions. Seven days post the first infusion another T-cell sample of $5\times10^8$ cells/m$^2$ will be administered intravenously. A total of two to three T-cell infusions may be given. Swelling at the primary and metastatic sites may occur, as well as, in the draining lymph nodes. Imaging (may include X-ray, Ultrasound, CT scan, MRI scan) may be completed prior to therapy and at all follow-up appointments as deemed necessary by the veterinarian. This data will be collected.

In companion canines diagnosed with B-cell LSA, the disease may be treated with SOC therapy. A minimum of 10 to 14 days post SOC must pass before pre-conditioning with high dose cytoxan occurs. Seven to ten days post pre-conditioning treatments, B-cell LSA diagnosed canines will be infused intravenously with one dose of $5\times10^8$ cells/m$^2$. Fourteen days later the patient will be infused intravenously with a second dose of $5\times10^8$ cells/m$^2$. B-cell LSA patients will receive 2 T-cell doses after the initial SOC treatment. The patient will be monitored for 1.5 to 3 hours post each infusion for any adverse reactions.

Companion canines diagnosed with AML have an extremely short time before blast crises develops. Current SOC is autologous or allogeneic HSCT with high dose cytoxan treatment at relapse. Fourteen days post the last dose of cyclosporine after the HSCT or 7 to 10 days post high dose cytoxan treatment (if relapse occurs), the first T-cell infusion will occur intravenously at a dose of $2\times10^8$ cells/m$^2$. Dogs with AML will receive a T-cell dose of $3\times10^8$ cells/m$^2$, then $4\times10^8$ cells/m$^2$, and then at a maximum dose of $5\times10^8$ cells/m$^2$ every 7 to 10 days post the prior infusion for a total number of infusions of up to 8 infusions depending on the patient's response and toleration of side effects. Blasts will be monitored 1 to 2 times per week to monitor efficacy and immune activation against the tumors.

In companion canines diagnosed with HS, SOC therapy will be initiated while T-cells are being manufactured. Seven to ten days post pre-conditioning high dose cytoxan treatment, the first T-cell infusion will occur intravenously at a dose of $2\times10^8$ cells/m$^2$. Dogs with HS will receive a T-cell dose of $3\times10^8$ cells/m$^2$, then $4\times10^8$ cells/m$^2$, and then at a maximum dose of $5\times10^8$ cells/m$^2$ every 7 to 10 days post the prior infusion for a total number of infusions of up to 4 infusions depending on the patient's response and toleration of side effects.

Allogeneic T-cell infusions will only in occur in a setting post allogeneic HSCT or DLI. Allogeneic T-cell infusions will not occur alone with any other type of SOC treatments or treatments of experimental nature for safety reasons to prevent lethal graft versus host disease (GVHD).

Example 5

Biomarkers Panels and Immunoscores to Identify Relapses, Anti-Tumor Immune Response, and Immune Status These panels may include sequencing analysis, cytokine secretion, PCR, and flow cytometric analysis, which can be combined to predict future responses using machine learning models and subsequent, algorithms, bioinformatics, and scripts. Machine learning based predictive computer modeling scripts will be generated and optimized on free statistical programs like "R", or through python or artificial intelligence-based system. Patient gene and protein data will be parsed into a computer model training set that will be used to train the computer to predict immune responses, potential efficacy, and adverse events. These data will be transferred by a bioinformatic specialist into an accessible format that can be used by clinicians to improve patient quality of life and outcomes, while personalizing the patient's treatment protocol.

These panels may include sequencing analysis, cytokine secretion, PCR, and flow cytometric analysis, which can be combined to predict future responses using machine learning models and subsequent, algorithms, bioinformatics, and scripts.

(I) Healthy Baseline Determination and development of Immune System Panel

Serum and peripheral blood (5 ml and 10 ml, respectively) will be collected from 100 normal/healthy companion canines (all breeds, ages 2 to 5 years) at their yearly wellness exams across the United States to provide a necessary cross-section and baseline of canine immune status. Cytokine serum levels (IL-6, TGF-B, IL-10, IL-2, IFN-y, etc) will be tested via ELISA or Luminex technologies. Peripheral blood will be analyzed using flow cytometry to determine CD3 T-cell numbers, CD3CD4 T-cell numbers, CD3CD8 T-cell numbers, CD4CD25 T-cell numbers, CD20/21/19 B-cell numbers, Granzyme B, perforin, and ratios. Copies of the CBCs from the primary veterinarian will also be collected to determine the absolute T cell counts and neutrophil to lymphocyte ratios, as well as, other data necessary to derive a complete picture of the canine's normal immune system. Canine-specific Nanostring panels or PCRs may be employed to determine intracellular protein expressions and signaling pathway activations. Testing will include ZAP70, CD3-zeta, and expression. TCR sequencing may be completed on 5 to 10 healthy canines to determine TCR repertoire changes and how these relate to the immune health of the canine before diagnosis of cancer. These protocols will be developed to include quality control and assurance necessary for clinical use. Data will be analyzed using the R statistical program with a script that will outline ranges, medians, means, and standard deviations. By combining all facets of this data using modeling (Section B.5.4.), an "Immunoscore" will be created. This number will give clinicians a numerical value that is representative of overall immune health.

(II) HSCT Transplant Immune Reconstitution

Serum and peripheral blood (5 ml and 10 ml, respectively) will be collected from 10 companion canines who have underwent a HSCT (autologous or allogeneic) across the United States to provide a necessary cross-section and baseline of canine immune reconstitution pre and post transplant. This will allow one to fine tune adoptive cellular strategies in these cases by understanding how the canine immune system reacts to transplantation procedures in the private practice settings. Canine must have a diagnosis of B-cell LSA or AML and must be treated by licensed veterinarians. Serum, CBCs and peripheral blood samples will be collected pre-transplant, 14 days post transplant. 28 days post transplant, 42 days post transplant, 70 days post transplant and 108 days post transplant. Data will be collected and analyzed as outlined above.

(III) Adoptive T-cell Transfer Reconstitution

Serum and peripheral blood (5 ml and 10 ml, respectively) will be collected from companion canines which have had a diagnosis of B-cell LSA, AML, OS, or HS across the United States to provide a necessary cross-section and baseline of canine immune reconstitution pre and post adoptive therapy. This will allow one to fine tune adoptive cellular treatment strategies in these cases by understanding how the canine immune system reacts to cellular infusions procedures in the private practice settings. Serum, CBCs, PCR and peripheral blood samples will be collected at diagnosis, 7 days post SOC therapy, 7 days post conditioning treatment (pre-T cell infusion), 7 days post each adoptive T-cell infusion, and then at monthly rechecks as recommended by the oncologist. Data will be collected and analyzed as outlined above.

(IV) Machine Learning to Predict Immune System Behavior in Canines (and Humans) and Immunoscore Development The increase of computer integration into patient's health has allowed the collection of data which assists in patient treatment plans. However, medicine is still, in many ways, practicing reactive medicine rather than proactive medicine, i.e. anticipating the patient's medical needs. Evolutionary learning combines aspects of machine learning with biological processes or natural evolution that are in constant flux. With dramatic interest in oncological immunotherapies, a looming, ever-present need is to predict how a vaccine or adoptive cellular therapy using TCRs will influence the patient's systemic immunity and reactions. The immune system and its landscape evolves continuously and learns based on endogenous and exogenous pressures similar to natural selection. Here we show that a combination of statistical analysis and machine learning of T cell gene signatures in companion canines diagnosed with B-cell lymphoma can predict with accuracy immune states related to remission, relapse, and homeostasis. These data will allow scientists and clinicians a like to determine which patients will benefit most from adoptive cellular therapy, when to infuse, dosing schemes, adverse events, predictions, and personalized treatments to bolster or dampened the resulting immune response. Metazoans develop functionally distinct cell types using essentially the same genomic blueprint. Over its life cycle, each cell transitions through distinct states (e.g. quiescence, differentiation, proliferation, senescence, etc) which are associated with manifestly distinct gene expression profiles (again, importantly transcribed from essentially the same genomic content). Mammalian genomes, carrying approximately 25,000 genes, impart an astronomical total possible combination of expression patterns and cell states. While molecular pathways, typically schematized as arrow-to-arrow diagrams (X→Y→Z), are useful representations of simple biochemical cascades, they lose clarity and simplicity to embody the high complexity and density of genome-wide expression data ("omics" data). Even by linking multiple pathways into circuit architectures of gene regulatory networks (GRNs), the need for integrative approaches stands. Not with-standing the complexity of underlying molecular interactions, integrative systems biology are realized by applying predictive models (Huang 2012). The scripts developed for the Immunoscore gene expression prediction profiles are based.

A website would be created so that clinicians and scientists could upload their data on the cloud and patient information. Alternatively, patient samples would be sent to a validated wet lab for processing. The Company would then be able to directly access the data once the patient and clinician signed waivers to release the information. Clinicians could choose the type of analysis needed. For a fee, we would analyze the data using a cloud and specific programming scripts. The scripts would encode analysis for Z scores, ANOVA, Pearson Correlation, PCA eigenvectors, and HMM or GLM analysis. This could be done HIPPA compliant and would set the standard for analysis. The analysis would be provided in an email or they could log on to the website. The Immunoscore could predict prognosis and diagnosis using gene expression data, phenotype data, blood and serum protein levels, and imaging results. The Immunoscore would be further broken down to include specific genes or factors using PCA that contributed the greatest influence on the score. This information would supply clinical decision support. Validation and calibration of the scripts and computer will be routinely completed as a part of quality control.

Example 6

Tumor Antigen-Specific TCR and CAR Portfolios

New scFv sequences will be generated against canine tumor targets. The stalk, hinge, transmembrane domain, and endodomains will be optimized for canine use. T cells will be transfected using a self-inactivating transposon and Transposase system.

The premise for this protocol is to exploit the SHM and AID in a contrived setting that would mutate the TCR within 24 hours and correctly identify tumor antigen and mutated TCR pairings. The TCR or scFv CAR would be sequenced and transfected into patient's T cells for expansion and subsequent more efficacious infusions.

(I) Mechanisms of SHM

The dog and human Activation-Induced Deaminase (AID) nucleotide sequence homology is 95% after BLAST-comparing. This supports the translational capabilities of the SHM method to develop new TCR and CAR tumor-antigen epitope recognizing sequences. Somatic hypermutation (SHM) is a cellular mechanism by which the iimmune system adapts to new foreign elements that confront it, as observed during class switching. SHM specifically diversifies B-cell receptor (BCR) but, we believe can be harnessed in manipulated setting to diversify the TCR as well. SHM involves a programmed process of mutations affecting the variable regions of immunoglobulin genes. Unlike germ line mutations, SHM affects only an organism's immune cells and these mutations are not passed on to the offspring. The BCR locus undergoes an extremely high rate of somatic mutations that is at least $10^5$ to $10^6$ fold greater than normal mutation rates that occur in the genome. Variations are mainly in the form of single base substitutions in "hotspots" or hypervariable regions. These sites involved in antigen recognition on the immunoglobulin.

(II) Mechanisms of AID

Experimental evidence supports the view that the mechanism of SHM involves deamination of cytosine to uracil in DNA by AID. A cytosine:guanine pair is thus directly mutated to a uracil:guanine mismatch. Uracil residues are not normally found in DNA, therefore, to maintain the integrity of the genome, most of these mutations must be repaired by high-fidelity DNA mismatch repair enzymes. The uracil bases are removed by the repair enzyme uracil-DNA glycosylase. Error-prone DNA polymerase are then recruited to fill in the gap and create mutations. The synthesis of this new DNA involves error-prone DNA polymerase, which after introducing mutations either at the positions of deaminated cytosine itself or neighboring base pairs. During B-cell division and activation, the immunoglobulin variable regions is transcribed and translated. The introduction of mutations in the rapid proliferating population of B cells ultimately culminates in the production of thousands of B cells, possessing slightly different receptors or varying specificities for the antigen, from which the BCR with the highest affinities for the antigen can be selected (Li, Wool et al. 2004; Janeway, Travers et al. 2005; Odegard and Schatz 2006; Teng and Papavasiliou 2007; Liu and Schatz 2009).

(III) Fast-Track TCR/CAR Portfolio Development

To build the TCR and CAR portfolios in a fast-tracked manner, autologous or allogeneic activated T fcells will be transfected with a 3D-printed linearized DNA plasmid of AID using lipofectamine. These cells will be incubated briefly in a fluorescent dye that will emit light when the mutated TCR/CAR binds to a tumor antigen. The AID+ve T cells will be co-cultured with ghost cell lines, autologous tumor or other cell lines. Three to 24 hours post co-culture at a 1:1 to a 1:4 ratio, fluorescent T cells will be harvested, sorted by fluorescence, and the positive TCRs/CARs will be sequenced using a commercially available MiSeq technology. Due to the large number of data collected per sample, sequence analysis will be carried out through rental of cloud space and time on the AWS server. The analyzed sequences will be then added to into a DNA plasmid that can be readily transfected into human and canine T cells. The mutated TCRs/CARs will be tested to ensure target-specific killing by granzyme B, perforin, CD107a and IFN-y production; and fluorescent killing assays with cell lines that are target antigen negative and positive. Data will also be collected on expansion rates and weekly phenotype expressions. Genotype data will also be collected for mRNA expression analysis to determine correct T-cell function.

(IV) Patient Treatment with Mutated TCR/CAR

T cells from an oncology patient will be collected from aphaeresis or peripheral blood as described previously. The T cells will be activated on ghost cells with IL-2 or IL-21 that have been transfected with the mutated TCR or mutated CAR. Once the number of T cells reaches a clinical number, the T cells will be harvested and cryopreserved for in-process testing and infusion as previously described.

Example 7

Immunostimulation or Depression Through the Infusion of Ghost Cells

In both cancer and autoimmune diseases, a systemic immunological dysfunction has occurred. Previous T-cell therapies for lymphoma and leukemia in humans have shown the varying degrees of infused CAR/TCR positive T-cell persistence which correlate with overall survival. Also, the infusion of T cells with persistence can produce long-lasting effects and correct the immunodysfunction in dogs with cancer.

Using the immunoscore (a combination of ANOVA, Pearcon Correlations, Z-scores, 3D PCA, and Hidden Markov Model), it is evident that immumodulation occurs. Therefore, I propose creating ghost trainer cells that only express on the cell surface a combination of GPI-linked cytokines and 1 type of MHC molecule. The trainers may express a combination of IL-10, TGFbeta, TNF-alpha, IFN-gamma, IL-21, IL-15, IL-2, IL-4, IL-12, IL-18, IL-6. The MHC will present a known auto-antigen in the case of the autoimmune diseases. Pro-inflammatory "Uppers" and anti-inflammatory "Downers" cytokine ghost trainers would be created as previously described. The cytokines and MHC (for autoimmune only) would be expressed in lipid rafts. Cells would be ghosted as earlier described and infused intravenously into human, feline, canine, or equine patients suffering from cancer, GVHD, or an autoimmune disease. The infused ghost cells would act as an adjuvant to suppress or activate systemic immunity via T-cell, NK cells, and B-cells. For autoimmune diseases, the MHC would express a known auto-antigen that would attract the dysfunctional T cells to the raft where it would bind and undergo suppression or apoptosis from the cytokine signaling. For cancer, the pro-inflammatory ghost would create a systemic immune activation in response to neo-antigens expressed after chemo or radio therapy. Dosing would be based on body surface area and weight. Infusions would take place during an active cycle of the autoimmune disease or GVHD, while for cancer the ghosts would be infused 24 hours to 7 days post chemo or radio therapy or at the first sign of immunosuppression. Dosing would start at 1e7 cells/m$^2$ to 5e9cells/m$^2$. Patients would receive unlimited doses, depending on tolerance, efficacy, and clinician's opinion.

Example 8

Exemplary Sequences Useful in the Production of Ghost Cell Trainers or Car Cells CMV promoter (www.algosome.com/resources/common-sequences.html#cmv) as shown below:

```
                                         (SEQ ID NO: 1)
TAGTAATCAATTACGGGGTCATTAGTTCATAGCCCATATATGGAGTTC

CGCGTTACATAACTTACGGTAAATGGCCCGCCTGGCTGACCGCCCAAC

GACCCCCGCCCATTGACGTCAATAATGACGTATGTTCCCATAGTAACG

CCAATAGGGACTTTCCATTGACGTCAATGGGTGGAGTATTTACGGTAA

ACTGCCCACTTGGCAGTACATCAAGTGTATCATATGCCAAGTACGCCC

CCTATTGACGTCAATGACGGTAAATGGCCCGCCTGGCATTATGCCCAG

TACATGACCTTATGGGACTTTCCTACTTGGCAGTACATCTACGTATTA

GTCATCGCTATTACCATGGTGATGCGGTTTTGGCAGTACATCAATGGG

CGTGGATAGCGGTTTGACTCACGGGGATTTCCAAGTCTCCACCCCATT

GACGTCAATGGGAGTTTGTTTTGGCACCAAAATCAACGGGACTTTCCA

AAATGTCGTAACAACTCCGCCCCATTGACGCAAATGGGCGGTAGGCGT

GTACGGTGGGAGGTCTATATAAGCAGAGCTGGTTTAGTGAACCGTCAG.
```

Kozack consensus sequence: GCCGCCGCCATGG (SEQ ID NO: 2).

CD64 (NM_000566.3, P12314): signaling peptide: 1-15; extracellular: 16-292 as shown below:

```
                                         (SEQ ID NO: 3)
QVDTTKAVITLQPPWVSVFQEETVTLHCEVLHLPGSSSTQWFLNGTAT

QTSTPSYRITSASVNDSGEYRCQRGLSGRSDPIQLEIHRGWLLLQVSS

RVFTEGEPLALRCHAWKDKLVYNVLYYRNGKAFKFFHWNSNLTILKTN

ISHNGTYHCSGMGKHRYTSAGISVTVKELFPAPVLNASVTSPLLEGNL

VTLSCETKLLLQRPGLQLYFSFYNIGSKTLRGRNTSSEYQILTARRED

SGLYWCEAATEDGNVLKRSPELELQVLGLQLPTPVWFH.
```

CD86 (NM_175862.4 variant 1, isoform 1, P42081): signaling peptide: 1-23; helical TM: 248-268; cytoplasmic: 269-329; extracellular peptides: 24-247 as shown below:

(SEQ ID NO: 4)
APLKIQAYFNETADLPCQFANSQNQSLSELVVFWQDQENLVLNEVYLG

KEKFDSVHSKYMGRTSFDSDSWTLRLHNLQIKDKGLYQCIIHHKKPTG

MIRIHQMNSELSVLANFSQPEIVPISNITENVYINLTCSSIHGYPEPK

KMSVLLRTKNSTIEYDGVMQKSQDNVTELYDVSISLSVSFPDVTSNMT

IFCILETDKTRLLSSPFSIELEDPQPPPDHIP.

CD137L (NM_003811.3, P41273): cytoplasmic domain: 1-28; helical, signal anchor for type II membrane protein TM: 29-41; extracellular domain: 50-254 as shown below:

(SEQ ID NO: 5)
ACPWAVSGARASPGSAASPRLREGPELSPDDPAGLLDLRQGMFAQLVA

QNVLLIDGPLSWYSDPGLAGVSLTGGLSYKEDTKELVVAKAGVYYVFF

QLELRRVVAGEGSGSVSLALHLQPLRSAAGAAALALTVDLPPASSEAR

NSAFGFQGRLLHLSAGQRLGVHLHTEARARHAWQLTQGATVLGLFRVT

PEIPAGLPSPRSE.

HUMAN IL-15 (P40933) as shown below: signal peptide: 1-29; propeptide: 30-48; chain: 49-162

(SEQ ID NO: 6)
MRISKPHLRSISIQCYLCLLLNSHFLTEAGIHVFILGCFSAGLPKTEA

NWVNVISDLKKIEDLIQSMHIDATLYTESDVHPSCKVTAMKCFLLELQ

VISLESGDASIHDTVENLIILANNSLSSNGNVTESGCKECEELEEKNI

KEFLQSFVHIVQMFINTS.

CD55 PROPEPTIDE AND LIPIDATION GPI SIGNALING ANCHOR, PROPEPTIDE: 353-381 as shown below: TTSGTTRLLSGHTCFTLTGLLGTLVTMGLLT (SEQ ID NO: 7).

NM_000574.4, Sig_peptide: 295-396 as underlined; Mat_peptide: 397-1353 as italicized:

(SEQ ID NO: 8)
```
   1  agcgagctcc tcctccttcc cctccccact ctccccgagt ctagggcccc cggggcgtat
  61  gacgccggag ccctctgacc gcacctctga ccacaacaaa ccctactcc acccgtcttg
 121  tttgtcccac ccttggtgac gcagagcccc agcccagacc ccgcccaaag cactcattta
 181  actggtattg cggagccacg aggcttctgc ttactgcaac tcgctccggc cgctgggcgt
 241  agctgcgact cggcggagtc ccggcggcgc gtccttgttc taacccggcg cgccatgacc
 301  gtcgcgcggc cgagcgtgcc cgcggcgctg cccctcctcg gggagctgcc ccggctgctg
 361  ctgctggtgc tgtttgtgcct gccggccgtg tggggtgact gtggccttcc cccagatgta
 421  cctaatgccc agccagcttt ggaaggccgt acaagttttc ccgaggatac tgtaataacg
 481  tacaaatgtg aagaaagctt tgtgaaaatt cctggcgaga aggactcagt gatctgcctt
 541  aagggcagtc aatggtcaga tattgaagag ttctgcaatc gtagctgcga ggtgccaaca
 601  aggctaaatt ctgcatccct caaacagcct tatatcactc agaattattt tccagtcggt
 661  actgttgtgg aatatgagtg ccgtccaggt tacagaagag aaccttctct atcaccaaaa
 721  ctaacttgcc ttcagaattt aaaatggtcc acagcagtcg aattttgtaa aagaaatca
 781  tgccctaatc cggagaaat acgaaatggt cagattgatg taccaggtgg catattattt
 841  ggtgcaacca tctccttctc atgtaacaca gggtacaaat tatttggctc gacttctagt
 901  ttttgtctta tttcaggcag ctctgtccag tggagtgacc cgttgccaga gtgcagagaa
 961  atttattgtc cagcaccacc acaaattgac aatggaataa ttcaagggga acgtgaccat
1021  tatggatata gacagtctgt aacgtatgca tgtaataaag gattcaccat gattggagag
1081  cactctattt attgtactgt gaataatgat gaaggagagt ggagtggccc accacctgaa
1141  tgcagaggaa aatctctaac ttccaaggtc ccaccaacag ttcagaaacc taccacagta
1201  aatgttccaa ctacagaagt ctcaccaact tctcagaaaa ccaccacaaa aaccaccaca
1261  ccaaatgctc aagcaacacg gagtacacct gtttccagga caaccaagca ttttcatgaa
1321  acaaccccaa ataaggaag tggaaccact tcaggtacta cccgtcttct atctgggcac
1381  acgtgtttca cgttgacagg tttgcttggg acgctagtaa ccatgggctt gctgacttag
1441  ccaaagaaga gttaagaaga aaatacacac aagtatacag actgttccta gtttcttaga.
```

Example 9

Exemplary HLA-Cw*3 and 5 Sequences

One or more of the following sequence may be used to identify and/or identify immune cells express TCR sequences specific for HLA-Cw*3 and 5.

| Epitope ID | Sequence | SEQ ID NO: |
|---|---|---|
| 515 | AAYAAAAAL | 9 |
| 5714 | AYAAQGYKVL | 10 |
| 15298 | FAVPNLQSL | 11 |
| 17619 | FRNLAYGRTCVLGK | 12 |
| 17892 | FSYMDDVVL | 13 |
| 18044 | FTPPHGGLL | 14 |
| 18328 | FVYGGSKTSL | 15 |
| 33104 | KQYLNLYPV | 16 |
| 42946 | MVHQAISPR | 17 |
| 50089 | PYFVRAQGLI | 18 |
| 51649 | QMVHQAISPR | 19 |
| 69922 | VMAPRTLVL | 20 |
| 70932 | VSFIEFVGW | 21 |
| 78969 | FAYDGKDYI | 22 |
| 78970 | FAYDGKDYL | 23 |
| 114817 | FAMPNFQTL | 24 |
| 141601 | AAADAAAAL | 25 |
| 141649 | GAVDPLLAL | 26 |
| 141650 | GAVDPLLKL | 27 |
| 141651 | GAVDPLLSL | 28 |
| 141652 | GAVDPLLVL | 29 |
| 141653 | GAVDPLLYL | 30 |
| 141727 | QAISPRTL | 31 |
| 141759 | TAMDVVYAL | 32 |
| 144186 | AAMPNFQTA | 33 |
| 144187 | AAMPNFQTL | 34 |
| 144209 | AQAISPRTL | 35 |
| 144259 | FAAISPRTL | 36 |
| 144260 | FAAPNFQTA | 37 |
| 144261 | FAAPNFQTL | 38 |
| 144262 | FAGISPRTL | 39 |
| 144263 | FAMANFQTA | 40 |
| 144264 | FAMANFQTL | 41 |
| 144265 | FAMPAFQTA | 42 |
| 144266 | FAMPAFQTL | 43 |
| 144267 | FAMPNAQTA | 44 |
| 144268 | FAMPNAQTL | 45 |
| 144269 | FAMPNFATA | 46 |
| 144270 | FAMPNFATL | 47 |
| 144271 | FAMPNFQAA | 48 |
| 144272 | FAMPNFQAL | 49 |
| 144273 | FAMPNFQTA | 50 |
| 144274 | FAMPNLQTA | 51 |
| 144275 | FAMPNLQTL | 52 |
| 144283 | FGMPNFQTA | 53 |
| 144284 | FGMPNFQTL | 54 |
| 144285 | FGMPNFQTM | 55 |
| 144291 | FQAISPRTL | 56 |
| 144295 | FVMPNFQTA | 57 |
| 144296 | FVMPNFQTL | 58 |
| 144313 | GQMVHQAI | 59 |
| 144314 | GQMVHQAIS | 60 |
| 144315 | GQMVHQAISPRT | 61 |
| 144316 | GQMVHQAISPRTL | 62 |
| 144327 | HAAISPRTL | 63 |
| 144328 | HAGISPRTL | 64 |
| 144329 | HAMPNFQTA | 65 |
| 144330 | HAMPNFQTL | 66 |
| 144332 | HQAASPRTL | 67 |
| 144333 | HQAIGPRTL | 68 |
| 144334 | HQAISARTL | 69 |
| 144335 | HQAISPATL | 70 |
| 144336 | HQAISPRAL | 71 |
| 144337 | HQAISPRT | 72 |
| 144338 | HQAISPRTA | 73 |
| 144339 | HQAISPRTD | 74 |
| 144340 | HQAISPRTF | 75 |
| 144341 | HQAISPRTK | 76 |
| 144342 | HQAISPRTL | 77 |
| 144343 | HQAISPRTM | 78 |
| 144344 | HQDISPRTL | 79 |
| 144345 | HQGISPRTL | 80 |

| Epitope ID | Sequence | SEQ ID NO: |
|---|---|---|
| 144346 | HQKISPRTL | 81 |
| 144347 | HQLISPRTL | 82 |
| 144348 | HQPISPRTL | 83 |
| 144349 | HQSISPRTL | 84 |
| 144389 | LAMPNFQTA | 85 |
| 144390 | LAMPNFQTL | 86 |
| 144416 | MVHQAISPRT | 87 |
| 144447 | QMVHQAIS | 88 |
| 144521 | VHQAISPR | 89 |
| 144522 | VHQAISPRT | 90 |
| 144523 | VHQAISPRTL | 91 |
| 156625 | AQFEHTILL | 92 |
| 162246 | FQNPFRSEL | 93 |
| 162775 | KSMETKVQF | 94 |
| 163272 | RLYPEGLAQL | 95 |
| 163894 | YAYDGKDYIAL | 96 |
| 190418 | FSSAGPCAL | 97 |
| 190421 | FTGLYSSTV | 98 |
| 190422 | FTQCGYPAL | 99 |
| 190423 | FTSAICSVV | 100 |
| 190438 | GTFVSPLPI | 101 |
| 190457 | KSVQHLESL | 102 |
| 190477 | LQDPRVRAL | 103 |
| 190480 | LSLDVSAAF | 104 |
| 190481 | LSPTVWLSV | 105 |
| 190485 | LSYQHFRKL | 106 |
| 190492 | MAARLCCQL | 107 |
| 190497 | MMWFWGPSL | 108 |
| 190526 | RAFPHCLAF | 109 |
| 190536 | SAAFYHLPL | 110 |
| 190581 | VSIPWTHKV | 111 |
| 190592 | YAAVTNFLL | 112 |
| 191716 | RVAPEEHPVL | 113 |
| 193448 | FVYGJSKTSL + MCM(X5) | 114 |
| 193682 | ALRDVSEEL | 115 |
| 193740 | FLAEHPNVTL | 116 |
| 193751 | FLDKNDHSL | 117 |
| 193814 | FLSEHPNVTL | 118 |
| 194187 | LLYQGPHNTL | 119 |
| 194188 | LMAEMGVHSV | 120 |
| 194305 | RMLDSVEKL | 121 |
| 194312 | RVPPPPQSV | 122 |
| 194557 | YAYEKPHVV | 123 |
| 194656 | YMYEKESEL | 124 |
| 195533 | ISLEGKPL | 125 |
| 196459 | FIAPTGHSL | 126 |
| 196711 | NTIDPSHPM | 127 |
| 208210 | FAHPYQYEL | 128 |
| 220053 | TGYIKTEL | 129 |
| 220571 | VATEGSREL | 130 |
| 221631 | YGFEKPSAI | 131 |
| 221641 | YGNPRTNGM | 132 |
| 224734 | FTDEESRVF | 133 |
| 224793 | IPNEIIHAL | 134 |
| 229882 | AAVDAGMAM | 135 |
| 229895 | FAYDGKDYLTL | 136 |
| 229910 | LAVHPSGVAL | 137 |
| 420580 | AAAAAAAAL | 138 |
| 420581 | AAYDAAAAA | 139 |
| 420582 | AAYDAAAAAAAL | 140 |
| 420583 | AAYDAAAAAAL | 141 |
| 420584 | AAYDAAAAAL | 142 |
| 420585 | AAYDAAAAL | 143 |
| 420586 | AAYDAAAL | 144 |
| 420595 | FAYDGKDYIAL | 145 |
| 420597 | GAVDPLKAL | 146 |
| 420615 | IAAGIFNDL | 147 |
| 420616 | IAIDPSKKL | 148 |
| 420617 | IAIIPSKAL | 149 |
| 420618 | IAIIPSKKL | 150 |
| 420651 | PAAAAFDL | 151 |
| 420660 | TAMDVVYKL | 152 |
| 420665 | VAYEAPSL | 153 |
| 433086 | VTDSGPTFNYL | 154 |
| 436040 | AAAYPHTSL | 155 |
| 436053 | AAMKALQAL | 156 |

-continued

| Epitope ID | Sequence | SEQ ID NO: |
|---|---|---|
| 436062 | AAVDRTTEL | 157 |
| 436063 | AAVPRAAFL | 158 |
| 436324 | ALAPGVRAV | 159 |
| 436332 | ALFQHITAL | 160 |
| 436362 | ALNPVANFHL | 161 |
| 436704 | AVMLHSFTL | 162 |
| 437182 | FAALHGPAL | 163 |
| 437183 | FADGHVLEL | 164 |
| 437185 | FADPHGKVF | 165 |
| 437186 | FAEDSLRVI | 166 |
| 437187 | FAEGFVRAL | 167 |
| 437188 | FAEGQGRAL | 168 |
| 437190 | FAGPHSTL | 169 |
| 437191 | FAGWGRAL | 170 |
| 437192 | FAIDPHLLL | 171 |
| 437195 | FAMIPAKEA | 172 |
| 437200 | FASELSRSL | 173 |
| 437204 | FAVIAHVGM | 174 |
| 437205 | FAVISRHSL | 175 |
| 437206 | FAYEGTRDSGM | 176 |
| 437258 | FGIDRPAEL | 177 |
| 437268 | FGQLGREL | 178 |
| 437272 | FIEDAVHVL | 179 |
| 437303 | FLADNHHQV | 180 |
| 437309 | FLDEKTHEL | 181 |
| 437349 | FNDPNAKEM | 182 |
| 437350 | FNFVGKIL | 183 |
| 437421 | FQHVGQTL | 184 |
| 437446 | FSHPREPAL | 185 |
| 437447 | FSKIGGIL | 186 |
| 437451 | FSSANSPFL | 187 |
| 437463 | FTVPHTHVF | 188 |
| 437472 | FVIETARQL | 189 |
| 437478 | FVNPHVSSF | 190 |
| 437629 | GIHETTFNSIM | 191 |
| 437771 | GQYPRALEL | 192 |
| 437882 | HAFLKTEF | 193 |
| 437893 | HAYLSKNSL | 194 |

-continued

| Epitope ID | Sequence | SEQ ID NO: |
|---|---|---|
| 438072 | IAAPFTSKL | 195 |
| 438083 | IAQPVRSFL | 196 |
| 438087 | IATYRTLL | 197 |
| 438206 | ILQPHVIAL | 198 |
| 438212 | IMNDIPIRL | 199 |
| 438292 | IQDDMHLVI | 200 |
| 438328 | ISEENFRVM | 201 |
| 438377 | IVIDPKNPL | 202 |
| 438413 | KAFDYPSRF | 203 |
| 438418 | KAHLGTAL | 204 |
| 438426 | KAWENSPNV | 205 |
| 438602 | KIAPNTPQL | 206 |
| 438718 | KMWENRQNL | 207 |
| 438791 | KQMEQISQFL | 208 |
| 438850 | KVAPAPAVV | 209 |
| 438868 | KVIDGLETL | 210 |
| 438900 | KVYERAVEF | 211 |
| 438922 | LADPVFRTL | 212 |
| 438928 | LALTRSSSL | 213 |
| 438930 | LAMRPLASL | 214 |
| 438934 | LAVDKSASL | 215 |
| 438936 | LAYPARPAQL | 216 |
| 439019 | LIVEPSREL | 217 |
| 439272 | MADPNIRFL | 218 |
| 439413 | MVIVPTREL | 219 |
| 439545 | NQYAYDGKDYIALN | 220 |
| 439773 | RAFPYGNVAF | 221 |
| 440002 | RLFESSQYL | 222 |
| 440047 | RLYQGINQL | 223 |
| 440302 | RVWDAEHPGL | 224 |
| 440326 | SAFDHFASV | 225 |
| 440334 | SAIGRAMEL | 226 |
| 440335 | SAIGYIHSL | 227 |
| 440336 | SAIPHPLIM | 228 |
| 440346 | SAYERSMM | 229 |
| 441161 | TQLGPPYHIL | 230 |
| 441233 | VADTVARVL | 231 |
| 441235 | VAEESRQVL | 232 |

| Epitope ID | Sequence | SEQ ID NO: |
|---|---|---|
| 441246 | VAMGYSHSL | 233 |
| 441253 | VAYLQAHAL | 234 |
| 441346 | VGDPSVHLL | 235 |
| 441385 | VIYPARISL | 236 |
| 441552 | VSQVGKEL | 237 |
| 441562 | VTDPTGFLRM | 238 |
| 441593 | VTVRPGLAM | 239 |
| 441621 | VVMNVVHQL | 240 |
| 441622 | VVMPIAHEF | 241 |
| 441635 | VVVAVGRAL | 242 |
| 441687 | YADPTKRLEL | 243 |
| 441689 | YAEVGRVL | 244 |
| 441694 | YAMDYSNKAL | 245 |
| 441702 | YAYDGKDYLAL | 246 |
| 441812 | YGTRYGASL | 247 |
| 441815 | YGYGHESEL | 248 |
| 441949 | YQMEKDIAM | 249 |
| 441976 | YSDDIPHAL | 250 |
| 441980 | YSHDGAFL | 251 |
| 441987 | YSLDHISSL | 252 |
| 441989 | YSNRVVDL | 253 |
| 442007 | YTYTSKAL | 254 |
| 461955 | AVRDLERAM | 255 |
| 474614 | AATATFAAA | 256 |
| 478229 | FSIDSPDSL | 257 |
| 488584 | VVPEPGQPL | 258 |

REFERENCES

Grinshtein, N., B. Bridle, et al. (2009). "Neoadjuvant vaccination provides superior protection against tumor relapse following surgery compared with adjuvant vaccination." Cancer Res 69(9): 3979-85.

Grinshtein, N., M. Ventresca, et al. (2009). "High-dose chemotherapy augments the efficacy of recombinant adenovirus vaccines and improves the therapeutic outcome." Cancer Gene Ther 16(4): 338-50.

Janeway, C. A., P. Travers, et al. (2005). Immunobiology (6th ed), Garland Science.

Jarnicki, A. G., J. Lysaght, et al. (2006). "Suppression of antitumor immunity by IL-10 and TGF-beta-producing T cells infiltrating the growing tumor: influence of tumor environment on the induction of CD4+ and CD8+ regulatory T cells." J Immunol 177: 896-904.

Li, Z., C. J. Wool, et al. (2004). "The generation of antibody diversity through somatic hypermutation and class switch recombination." Gene and Development 18(1): 1-11.

Liu, M. and D. G. Schatz (2009). "Balancing AID and DNA repair during somatic hypermutation. Trends in Immunology." Trends in Immunology 30(4): 173-181.

Michishita, M., T. Uto, et al. (2013). "Antitumor effect of bevacizumab in a xenograft model of canine hemangiopericytoma." J Pharmacol Sci 121(4): 339-42.

O'Connor, C. M., S. Sheppard, et al. (2012). "Adoptive T-cell Therapy Improves Treatment of Canine Non-Hodgkin Lymphoma Post Chemotherapy." Scientific Reports.

Odegard, V. H. and D. G. Schatz (2006). "Targeting of somatic hypermutation." Nat Rev Immunol 6(8): 573-583.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method of treating a subject having cancer, the method comprising:
   a. transfecting a cell expressing a major histocompatibility complex (MHC) molecule with a plurality of vectors each comprising a gene encoding a protein of interest and a glycosylphosphatidylinositol (GPI) signaling anchor, or a vector comprising a fusion gene encoding a plurality of proteins of interest and GPI signaling anchors, such that the proteins of interest are expressed and anchored to the cell surface via the GPI signaling anchors, wherein the proteins of interest include IL-15, IL-21, IL-2, CD86, CD64, and CD137L;
   b. lysing the cell of step (a) by hypotonic means to form a ghost cell (GHC) that is substantially free of all intracellular components;
   c. co-culturing the GHC with an immune cell isolated from the subject to expand and activate the immune cell, wherein the immune cell is a T cell or an NK cell; and
   d. infusing the activated immune cell into the subject.

2. The method of claim 1, wherein the GPI anchored proteins of interest are within a lipid raft.

3. The method of claim 1, wherein the MHC molecule is HLA-Cw*3 and/or HLA-Cw*5.

4. The method of claim 1, wherein said GHC is of human, canine, feline, murine, or equine origin.

5. The method of claim 1, wherein said GHC is derived from a primary cell culture or an immortalized cell line.

6. The method of claim 5, wherein the immortalized cell line is K562 or Jurkat.

7. The method of claim 1, wherein the cancer is a hematologic cancer or a solid cancer.

8. The method of claim 7, wherein the hematologic cancer is leukemia or lymphoma.

9. The method of claim 7, wherein the solid cancer is osteosarcoma, hemangiosarcoma, transitional cell carcinoma, melanoma, glioblastoma, neuroblastoma, mammary carcinoma, or a sarcoma or carcinoma of the gastrointestinal system.

10. The method of claim 1, wherein the subject is a companion animal or a human.

11. The method of claim 10, wherein the companion animal is a canine, feline, or equine.

12. A method of treating a subject having cancer, the method comprising:
    a. transfecting a cell with
       i. a vector encoding a major histocompatibility complex (MHC) molecule and a glycosylphosphatidylinositol (GPI) signaling anchor; and
       ii. a plurality of vectors each comprising a gene encoding a protein of interest and a GPI signaling anchor, or a vector comprising a fusion gene encoding a plurality of proteins of interest and GPI signaling anchors, such that the MHC molecule and the proteins of interest are expressed and anchored to the cell surface via the GPI signaling anchors, wherein the proteins of interest include IL-15, IL-21, IL-2, CD86, CD64, and CD137L;
    b. lysing the cell of step (a) by hypotonic means to form a ghost cell (GHC) that is substantially free of all intracellular components;
    c. co-culturing the GHC with an immune cell isolated from the subject to expand and activate the immune cell, wherein the immune cell is a T cell or an NK cell; and
    d. infusing the activated immune cell into the subject.

13. The method of claim 12, wherein said GHC is of human, canine, feline, murine, or equine origin.

14. The method of claim 12, wherein the proteins of interest are within a lipid raft.

15. The method of claim 12, wherein the MHC molecules are GPI anchored on the cell surface within a lipid raft.

16. The method of claim 12, wherein the MHC molecules are HLA-Cw*3 and/or HLA-Cw*5.

17. The method of claim 12, wherein said GHC is derived from a primary cell culture or an immortalized cell line.

18. The method of claim 17, wherein the immortalized cell line is K562 or Jurkat.

19. The method of claim 12, wherein the cancer is a hematologic cancer or a solid cancer.

20. The method of claim 19, wherein the hematologic cancer is leukemia or lymphoma.

21. The method of claim 19, wherein the solid cancer is osteosarcoma, hemangiosarcoma, transitional cell carcinoma, melanoma, glioblastoma, neuroblastoma, mammary carcinoma, or a sarcoma or carcinoma of the gastrointestinal system.

22. The method of claim 12, wherein the subject is a companion animal or a human.

23. The method of claim 22, wherein the companion animal is a canine, feline, or equine.

* * * * *